US009446062B2

(12) United States Patent
Feinstein et al.

(10) Patent No.: US 9,446,062 B2
(45) Date of Patent: *Sep. 20, 2016

(54) METHODS OF TREATING ISCHEMIA-REPERFUSION INJURY WITH SIRNAS

(71) Applicant: QUARK PHARMACEUTICALS, INC., Fremont, CA (US)

(72) Inventors: Elena Feinstein, Rehovot (IL); Hagar Kalinski, Rishon-le-Zion (IL)

(73) Assignee: Quark Pharmaceuticals, Inc., Fremont, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/592,386

(22) Filed: Jan. 8, 2015

(65) Prior Publication Data

US 2015/0329866 A1 Nov. 19, 2015

Related U.S. Application Data

(63) Continuation of application No. 11/978,089, filed on Oct. 25, 2007, now abandoned.

(60) Provisional application No. 60/854,503, filed on Oct. 25, 2006, provisional application No. 60/930,493, filed on May 15, 2007.

(51) Int. Cl.
| | | |
|---|---|---|
| *C12N 15/11* | (2006.01) | |
| *A61K 31/70* | (2006.01) | |
| *C12N 15/113* | (2010.01) | |

(52) U.S. Cl.
CPC ............. *A61K 31/70* (2013.01); *C12N 15/113* (2013.01); *C12N 15/1136* (2013.01); *C12N 15/1137* (2013.01); *C12N 2310/11* (2013.01); *C12N 2310/14* (2013.01); *C12N 2310/315* (2013.01); *C12N 2310/321* (2013.01); *C12N 2310/343* (2013.01)

(58) Field of Classification Search
None
See application file for complete search history.

(56) References Cited

U.S. PATENT DOCUMENTS

| | | | |
|---|---|---|---|
| 5,898,031 | A | 4/1999 | Crooke |
| 5,929,042 | A | 7/1999 | Troy |
| 6,107,094 | A | 8/2000 | Crooke |
| 6,372,249 | B1 | 4/2002 | Smith et al. |
| 6,506,559 | B1 | 1/2003 | Fire et al. |
| 7,452,987 | B2 | 11/2008 | Giese et al. |
| 2005/0080246 | A1 | 4/2005 | Allerson et al. |
| 2006/0069056 | A1 | 3/2006 | Feinstein et al. |
| 2006/0217329 | A1 | 9/2006 | Feinstein |
| 2008/0311051 | A1 | 12/2008 | Chauvier et al. |

FOREIGN PATENT DOCUMENTS

| | | |
|---|---|---|
| WO | WO 00/44895 | 8/2000 |
| WO | WO 01/36646 | 5/2001 |
| WO | WO 01/75164 | 10/2001 |
| WO | WO 02/24720 | 3/2002 |
| WO | WO 02/44321 | 6/2002 |
| WO | WO 02/055693 | 7/2002 |
| WO | WO 03/070918 | 8/2003 |
| WO | WO 03/074654 | 9/2003 |
| WO | WO 2004/006513 | 1/2004 |
| WO | WO 2004/009797 | 1/2004 |
| WO | WO 2004/015107 | 2/2004 |
| WO | WO 2004/053068 | 6/2004 |
| WO | WO 2004/065613 | 8/2004 |
| WO | WO 2004/103389 | 12/2004 |
| WO | WO 2005/013886 | 2/2005 |
| WO | WO 2007/110210 | 10/2007 |

OTHER PUBLICATIONS

Barik, Sailen (2005). "Silence of the Transcripts; RNA Interference in Medicine," J. Mol. Med. 83:764-773.
Bartel, David P. et al. (2004). "MircroRNAs: Genomics Biogenesis, Mechanism, and Function," Cell, 116:281-297.
Bass BL et al., ( 2001) . "The Short Answer," Nature 411:428-429.
Bernstein, Emily et al. (2001). "Role for a Bidentate Ribonuclease in the Initiation Step of RNA Interference," Nature, 409:363-366.
Bitko, Vira et al. (2004) "Inhibition of Respiratory Viruses by Nasally Administered siRNA," Nature Medicine, 11(1):50-55.
Brummelkamp, Thijn R. et al. (2002). "A System for Stable Expression of Short Interfering RNAs in Mammalian Cells," Science, 296-550-553.
Caplen, Natasha J. et al. (2001). "Specific Inhibition of Gene Expression by Small Double-Stranded RNAs in Invertebrate Vertebrate Systems," PNAS, 98(17):9742-9747.
Chakraborty, Chiranjib (2007} "Potentially of Small Interfering RNAs (siRNA} as Recent Therapeutic Targets for Gene-Silencing," Current Drug Targets, 8:469-482.
Chalk, Alistair M. et al., (2004). "Improved and Autonated Prediction of Effective siRNA," Biochemical and Biophysical Research Communications, 319:264-274.
Elbashir SM, et al. (2001) "Functional anatomy of siRNAs for mediating efficient RNAi in Drosophila melanogaster embryo lysate," EMBO J. 20(23):6877-88.
Elbashir, Sayda M. et al. (2000). "RNA Interference is Mediated by 21- and 22-nucleotide RNAs," Genes & Development, 15: 188-200.
Elbashir, Sayda M_et al. (2001 ). "Duplexes of 21-nucleotide RNAs mediated RNA interference in cultured mammalian cells," Nature, 411 :494-498.

(Continued)

*Primary Examiner* — Dana Shin
(74) *Attorney, Agent, or Firm* — Fish & Richardson P.C.

(57) ABSTRACT

The invention relates to compounds, in particular siRNAs, which inhibit the expression of specific human genes. The invention also relates to pharmaceutical compositions comprising such compounds and a pharmaceutically acceptable carrier. The present invention also provides a method of treating and/or preventing the incidence or severity of various diseases or conditions associated with the genes and/or symptoms associated with such diseases or conditions comprising administering to a subject in need of treatment for such disease or condition and/or symptom the compound or the pharmaceutical composition in a therapeutically effective dose so as to thereby treat the subject. The invention also provides antibodies which inhibit specified human polypeptides and pharmaceutical compositions comprising one or more such antibodies.

14 Claims, No Drawings

(56) References Cited

OTHER PUBLICATIONS

Far et al., The activity of siRNA in mammalian cells is related to structural target accessibility: a comparison with antisense oligonucleotides, 2003, Nucleic Acids Research, vol. 31, pp. 4417-4424.
Fire, Andrew et al., (1998). "Potent and Specific Genetic Interference by Double-stranded RNA in Caenorhabditis Elegans," Nature, 391:806-811.
Hitti M, "Laser Best for Diabetic Macular Edema," Published online Aug. 6, 2008, http://diabetes.webmd.com/news/20080806/laser-best-for-diabetictmacular-edema.
Lee, Youngtae et al., (2003). "The nuclear RNase III Drosha initiates mircoRNA processing," Nature, 425:415-419.
Levenkova, Natasha et al., (2004). "Gene specific siRNA selector," Bioinformatics, 20(3)430-432.
McManus, Michael T. and Sharp, Phillip A., (2002). "Gene Silencing in Mammals by Small Interfering RNAs," Genetics, 3:737-747.
Miyagishi et al., Comparison of the suppressive effects of antisense oligonucleotides and siRNAs directed against the same targets in mammalian cells, 2003, Antisense and Nucleic Acid Drug Development, vol. 13, pp. 1-7.
Pille J.-Y. et al. I (2005). "Anti-RHOA and anti-RHOC siRNAs Inhibit the Proliferation and Invasiveness of MDA-MB-231 Breast Cancer Cells in Vitro and In Vivo," Mol. Ther., 11 (2):267-274.
Sioud, Moudly and Leirdal, Marianne, (2004). "Potential Design Rules and Enzymatic Synthesis of siRNAs," Methods in Molecular Biology, 252:457-468.
Tolentino, Michael J. et al., (2004). "Intravitreal Injection of Vascular Endothelial Growth Factor . . . ," Retina, The Journal of Retinal and Vitreous Diseases, 24(1):132-138.
Ui-Tei, Kumiko et al., (2004). "Guidelines for the selection of highly effective siRNA sequences for mammalian and chick RNA . . . ," Nucleic Acids Research, 32(3):936-948.
Vickers et al., Efficient reduction of target RNAs by small interfering RNA and RNase H/dependent antisense agents, 2003, The Journal of Biological Chemistry, vol. 278, pp. 7108-7118.
Wang W. et al., Endotoxemic acute renal failure is attenuated in caspase/1/deficient mice, (2005) AJP:Renal Physiology, vol. 288, No. 5, pp. F997-F1004.
International Search Report issued by the International Searching Authority (ISA/US) on Oct. 7, 2008 in connection with International Application No. PCT/IL07/01278.
Written Opinion issued by the International Searching Authority (ISA/US) on Oct. 7, 2008 in connection with International Application No. PCT/IL07/01278.
International Preliminary Report on Patentability issued by the International Searching Authority (ISA/US) on May 7, 2009 in connection with International Application No. PCT/IL07/01278.
Extended European search report and European search opinion, issued on Sep. 1, 2011, in connection with European Application No. 11709127.

US 9,446,062 B2

METHODS OF TREATING ISCHEMIA-REPERFUSION INJURY WITH SIRNAS

CROSS REFERENCE TO RELATED APPLICATIONS

This application is a continuation of U.S. patent application Ser. No. 11/978,089 filed Oct. 25, 2007, which claims the benefit of US Provisional patent application No. 60/854,503 filed Oct. 25, 2006, and of U.S. Provisional patent application No. 60/930,493 filed May 15, 2007, both of which are hereby incorporated by reference in their entirety.

Throughout this application various patents and publications are cited. The disclosures of these documents in their entireties are hereby incorporated by reference into this application to more fully describe the state of the art to which this invention pertains.

FIELD OF THE INVENTION

The present invention relates to compounds, pharmaceutical compositions comprising same and methods of use thereof for the inhibition of certain genes, including pro-apoptotic genes. The compounds and compositions are thus useful in the treatment of subjects suffering from diseases or conditions and or symptoms associated with such diseases or conditions in which gene expression has adverse consequences. In particular embodiments, the invention provides siRNA oligonucleotides, compositions comprising same and methods of use thereof in the treatment of hearing loss including acoustic trauma and presbycusis; acute renal failure (ARF); glaucoma; acute respiratory distress syndrome (ARDS) and other acute lung and respiratory injuries; ischemia-reperfusion (I/R) injury following lung transplantation, organ transplantation including lung, liver, heart, pancreas, and kidney transplantation; nephro- and neurotoxicity; spinal cord injury; pressure sores; age-related macular degeneration (AMD); dry eye syndrome; oral mucositis, and chronic obstructive pulmonary disease (COPD).

BACKGROUND OF THE INVENTION siRNAs and RNA Interference

RNA interference (RNAi) is a phenomenon involving double-stranded (ds) RNA-dependent gene-specific post-transcriptional silencing. Initial attempts to study this phenomenon and to manipulate mammalian cells experimentally were frustrated by an active, non-specific antiviral defense mechanism which was activated in response to long dsRNA molecules (Gil et al., Apoptosis, 2000, 53:107-114). Later, it was discovered that synthetic duplexes of 21 nucleotide RNAs could mediate gene specific RNAi in mammalian cells, without stimulating the generic antiviral defense mechanisms Elbashir et al. Nature 2001, 411:494-498 and Caplen et al. PNAS 2001, 98:9742-9747). As a result, small interfering RNAs (siRNAs), which are short double-stranded RNAs, have been widely used to inhibit gene expression and understand gene function.

RNA interference (RNAi) is mediated by small interfering RNAs (siRNAs) (Fire et al, Nature 1998, 391:806) or microRNAs (miRNAs) (Ambros V. Nature 2004, 431:350-355); and Bartel D P. Cell. 2004 116(2):281-97). The corresponding process is commonly referred to as specific post-transcriptional gene silencing when observed in plants and as quelling when observed in fungi.

An siRNA is a double-stranded RNA which down-regulates or silences (i.e. fully or partially inhibits) the expression of an endogenous or exogenous gene/mRNA. RNA interference is based on the ability of certain dsRNA species to enter a specific protein complex, where they are then targeted to complementary cellular RNAs and specifically degrades them. Thus, the RNA interference response features an endonuclease complex containing an siRNA, commonly referred to as an RNA-induced silencing complex (RISC), which mediates cleavage of single-stranded RNA having a sequence complementary to the antisense strand of the siRNA duplex. Cleavage of the target RNA may take place in the middle of the region complementary to the antisense strand of the siRNA duplex (Elbashir, et al. Genes Dev., 2001, 15:188). In more detail, longer dsRNAs are digested into short (17-29 bp) dsRNA fragments (also referred to as short inhibitory RNAs or "siRNAs") by type III RNAses (DICER, DROSHA, etc., (see Benstein et al., Nature, 2001, 409:363-6 and Lee et al., Nature, 2003, 425:415-9). The RISC protein complex recognizes these fragments and complementary mRNA. The whole process is culminated by endonuclease cleavage of target mRNA (McManus and Sharp, Nature Rev Genet, 2002, 3:737-47; Paddison and Hannon, Curr Opin Mol Ther. 2003, 5(3): 217-24). (For additional information on these terms and proposed mechanisms, see for example, Bernstein, et al., RNA. 2001, 7(11):1509-21; Nishikura, Cell. 2001, 107(4): 415-8 and PCT Publication No. WO 01/36646).

Studies have revealed that siRNA can be effective in vivo in both mammals and humans. Specifically, Bitko et al., showed that specific siRNAs directed against the respiratory syncytial virus (RSV) nucleocapsid N gene are effective in treating mice when administered intranasally (Bitko et al., Nat. Med. 2005, 11(1):50-55). For reviews of therapeutic applications of siRNAs see Batik (Mol. Med 2005, 83: 764-773) and Chakraborty (Current Drug Targets 2007 8(3):469-82). In addition, clinical studies with short siRNAs that target the VEGFR1 receptor in order to treat age-related macular degeneration (AMD) have been conducted in human patients. In studies such siRNA administered by intravitreal (intraocular) injection was found effective and safe in 14 patients tested (Kaiser, Am J Ophthalmol. 2006 142(4):660-8).

Pro-Apoptotic Genes

Pro-apoptotic genes are generally defined as genes that play a role in apoptotic cell death. A non-limiting list of pro-apoptotic genes, useful in the present invention is as follows: tumor protein p53 binding protein 2 (TP53BP2); leucine-rich repeats and death domain containing (LRDD); cytochrome b-245, alpha polypeptide (CYBA, p22phox): activating transcription factor 3 (ATF3); caspase 2, apoptosis-related cysteine peptidase (CASP2); NADPH oxidase 3 (NOX3); harakiri, BCL2 interacting protein (HRK, BID3); complement component 1, q subcomponent binding protein (C1QBP); BCL2/adenovirus E1B 19 kDa interacting protein 3 (BNIP3); mitogen-activated protein kinase 8 (MAPK8, JNK1); mitogen-activated protein kinase 14 (MAPK14, p38) ras-related C3 botulinum toxin substrate 1 (rho family, small GTP binding protein RAC1): glycogen synthase kinase 3 beta (GSK3B); purinergic receptor P2X, ligand-gated ion channel. 7 (P2RX7); transient receptor potential cation channel, subfamily M, member 2 (TRPM2); poly (ADP-ribose) glycohydrolase (PARG); CD38 molecule (CD38); STEAP family member 4 (STEAP4); bone morphogenetic protein 2 (BMP2); gap junction protein, alpha 1, 43 kDa (connexin 43, GJA1); TYRO protein tyrosine kinase binding protein (TYROBP); connective tissue growth factor (CTGF); secreted phosphoprotein 1 (osteopontin, SPP1); reticulon 4 receptor (RTN4R); annexin A2 (ANXA2): ras homolog gene family, member A (RHOA); and dual oxidase 1 (DUOX1).

Hearing Loss

Chemical-Induced Ototoxicity

The ototoxic effects of various therapeutic drugs on auditory cells and spiral ganglion neurons are often the factor limiting their therapeutic usefulness. Commonly used ototoxic drugs include the widely used chemotherapeutic agent cisplatin and its analogs, aminoglycoside antibiotics, e.g. gentamycin, quinine and its analogs, salicylate and its analogs, and loop-diuretics.

For example, antibacterial aminoglycosides such as gentamycin, streptomycin, kanamycin, tobramycin, and the like are known to have serious toxic side effects, particularly ototoxicity and nephrotoxicity, which reduce their value as therapeutic agents (see Goodman and Gilman's The Pharmacological Basis of Therapeutics. 6th ed., A. Goodman Gilman et al., eds. Macmillan Publishing Co., Inc., 1980. NY, pp. 1169-71). Thus, ototoxicity is a recognized dose-limiting side-effect of antibiotic administration. Studies have shown that from 4 to 15% of patients receiving one gram per day for greater than one week develop measurable hearing loss, which gradually worsens and can lead to permanent deafness if treatment continues.

Ototoxicity is also a serious dose-limiting side-effect for cisplatin, a platinum coordination complex, that has proven effective on a variety of human cancers including testicular, ovarian, bladder, and head and neck cancer. Cisplatin (Platinol®) damages auditory and vestibular systems. Salicylates, such as aspirin, are the drugs most commonly used because of their anti-inflammatory, analgesic, anti-pyretic and anti-thrombotic effects. Unfortunately, they too have ototoxic side effects including tinnitus ("ringing in the ears") and temporary hearing loss. Moreover, if the drug is used at high doses for a prolonged time, hearing impairment can become persistent and irreversible.

Without being bound by theory, it is believed that cisplatin drugs and other potentially ototoxic drugs induce the ototoxic effects via apoptosis in inner ear tissue, particularly inner ear hair cells (Zhang et al., Neuroscience 2003, 120 (1):191-205; Wang et al., J. Neuroscience, 2003, 23(24): 8596-8607). In mammals, auditory hair cells are produced only during embryonic development and do not regenerate if lost during postnatal life. Therefore. a loss of hair cells will result in profound and irreversible deafness. Unfortunately, there are presently no effective therapies to treat the cochlea and reverse this condition. Thus, an effective therapy to prevent cell death of auditory hair cells would be of great therapeutic value. U.S. patent application Ser. No. 11/655,610, assigned to the applicant of the present invention relates to methods for treating hearing impairment in a subject comprising administering to the subject a composition comprising an effective amount of a p53 polynucleotide inhibitor, and optionally an inhibitor of a pro-apoptotic gene.

Presbycusis

Another type of hearing loss is presbycusis, which is hearing loss that gradually occurs in most individuals as they age. About 30-35 percent of adults between the ages of 65 and 75 years and 40-50 percent of people 75 and older experience hearing loss. Accordingly, there exists a need for means to prevent, reduce or treat the incidence and/or severity of inner car disorders and hearing impairments involving inner ear tissue, particularly inner ear hair cells.

Acoustic Trauma

Acoustic trauma is a type of hearing loss that is caused by prolonged exposure to loud noises. Without wishing to be bound to theory, exposure to loud noise causes the hair cells on the cochlea to become less sensitive. With more severe exposure, injury can proceed from a loss of adjacent supporting cells to complete disruption of the organ of Corti. Death of the sensory cell can lead to progressive Wallerian degeneration and loss of primary auditory nerve fibers.

Of particular interest are those adverse conditions arising as a side-effect of therapeutic drugs including cisplatin and its analogs, aminoglycoside antibiotics, salicylate and its analogs, or loop diuretics. Thus, there exits a need for treatment methods which will allow higher and thus more effective dosing, while preventing or reducing ototoxic effects caused by these drugs. Thus, compositions and methods are needed that provide a safe, effective, and prolonged means for prophylactic or curative treatment of hearing impairments related to inner car tissue damage, loss, or degeneration, particularly ototoxin-induced and particularly involving inner ear hair cells. In mammals, auditory hair cells are produced only during embryonic development and do not regenerate if lost during postnatal life, therefore, a loss of hair cells will result in profound and irreversible deafness. Unfortunately, at present, there are no effective therapies to treat the cochlea and reverse this condition. Thus, an effective therapy to prevent cell death of auditory hair cells would be of great therapeutic value.

Acute Renal Failure

Acute renal failure (ARF) is a clinical syndrome characterized by rapid deterioration of renal function that occurs within days. The principal feature of ARF is an abrupt decline in glomerular filtration rate (GFR), resulting in the retention of nitrogenous wastes (urea, creatinine). World-wide, severe ARF occurs in about 170-200 persons per million of population annually. Today, there is no specific treatment for established ARF. Several drugs have been found to ameliorate toxic and ischemic experimental ARF, as manifested by lower serum creatnine levels, reduced histological damage and faster recovery of renal function in animal models. These include anti-oxidants, calcium channel blockers, diuretics, vasoactive substances, growth factors, anti-inflammatory agents and more. However, when these drugs were tested in clinical trials no benefit was shown and their use for treating ARF has not been approved.

In the majority of hospitalized ARF patients, ARF is caused by acute tubular necrosis (ATN), which results from ischemic and/or nephrotoxic insults. Renal hypoperfusion is caused by hypovolemic. cardiogenic and septic shock, by administration of vasoconstrictive drugs or renovascular injury. Nephrotoxins include exogenous toxins such as contrast media and antinoglycosides as well as endogenous toxin such as myoglobin. Recent studies suggest that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum. It has been suggested that apoptotic tubule cell death may be more predictive of functional changes than necrotic cell death (Komarov et al. Science. 1999, 285(5434):1733-7); Supavekin et al. Kidney Int. 2003, 63(5):1714-24). In conclusion, there are no currently satisfactory modes of therapy for the prevention and/or treatment of acute renal failure, and there is a clear need to develop novel compounds for this purpose.

Renal Transplant

Delayed Graft Function

Delayed graft function (DGF) is the most common complication of the immediate postoperative period in renal transplantation and results in poor graft outcome (Moreso et al. 1999. Nephrol. Dial. Transplant. 14(4):930-35). Although the incidence and definition of DGF vary among transplant centers, the consequences are invariable: prolonged hospital stay, additional invasive procedures, and additional cost to the patient and health-care system.

Acute Transplant Rejection

Graft rejection has been categorized into three subsets depending on the onset of graft destruction: Hyperacute rejection is the term applied to very early graft destruction, usually within the first 48 hours. Acute rejection has an onset of several days days to months or even years after transplantation and can involve humoral and/or cellular mechanisms. Chronic rejection relates to chronic alloreactive immune response.

Glaucoma

Glaucoma is one of the leading causes of blindness in the world. It affects approximately 66.8 million people worldwide. At least 12,000 Americans are blinded by this disease each year (Kahn and Milton, Am J Epidemiol. 1980, 111 (6):769-76). Glaucoma is characterized by the degeneration of axons in the optic nerve head, primarily due to elevated intraocular pressure (IOP). One of the most common forms of glaucoma, known as primary open-angle glaucoma (POAG), results from the increased resistance of aqueous humor outflow in the trabecular meshwork (TM), causing IOP elevation and eventual optic nerve damage. Mucke (IDrugs 2007, 10(1):37-41) reviews current therapeutics, including siRNA to various targets for the treatment of ocular diseases, for example, age-related macular degeneration (AMD) and glaucoma.

Acute Respiratory Distress Syndrome

Acute respiratory distress syndrome (ARDS), also known as respiratory distress syndrome (RDS) or adult respiratory distress syndrome (in contrast with infant respiratory distress syndrome, IRDS) is a serious reaction to various forms of injuries to the lung. This is the most important disorder resulting in increased permeability pulmonary edema.

ARDS is a severe lung disease caused by a variety of direct and indirect insults. It is characterized by inflammation of the lung parenchyma leading to impaired gas exchange with concomitant systemic release of inflammatory mediators which cause inflammation, hypoxemia and frequently result in failure of multiple organs. This condition is life threatening and often lethal, usually requiring mechanical ventilation and admission to an intensive care unit. A less severe form is called acute lung injury (ALI).

Acute Lung Transplant Rejection

Acute allograft rejection remains a significant problem in lung transplantation despite advances in immunosuppressive medication. Rejection, and ultimately early morbidity and mortality may result from ischemia-reperfusion (I/R) injury and hypoxic injury.

Spinal Cord Injury

Spinal cord injury or myelopathy, is a disturbance of the spinal cord that results in loss of sensation and/or mobility. The two most common types of spinal cord injury are due to trauma and disease. Traumatic injuries are often due to automobile accidents, falls, gunshots diving accidents, and the like. Diseases which can affect the spinal cord include polio, spina bifida, tumors, and Friedreich's ataxia.

Ischemia-Reperfasion Injury Following Organ Transplantation

Ischemia reperfusion injury (IRI) is one of the leading causes of death in organ allograft recipients. Significant IRI occurs in every organ transplant from a deceased donor and in some from live donors. It contributes to increased acute rejection and impaired long-term allograft function. Lung transplantation, the only definitive therapy for many patients with end stage lung disease, has poor survival rates in all solid allograft recipients.

Pressure Sores

Pressure sores, often known as bedsores or pressure ulcers, are areas of damaged skin and tissue. With unrelieved pressure, tissue ischemia can develop resulting in the accumulation of metabolic waste in the interstitial tissue, resulting in anoxia and cellular death. This pressure-induced ischemia also leads to excessive tissue hypoxia, further promoting bacterial proliferation and tissue destruction.

Age-Related Macular Degeneration

The most common cause of decreased best-corrected, vision in individuals over 65 years of age in the United States is the retinal disorder known as age-related macular degeneration (AMD). The area of the eye affected by AMD is the macula, a small area in the center of the retina, composed primarily of photoreceptor cells. As AMD progresses, the disease is characterized by loss of sharp, central vision. So-called "dry" AMD accounts for about 85% -90% of AMD patients and involves alterations in eye pigment distribution, loss of photoreceptors and diminished retinal function. due to overall atrophy of cells. "Wet" AMD involves proliferation of abnormal choroidal vessels leading to clots or scars in the sub-retinal space. Thus, the onset of "wet" AMD occurs because of the formation of an abnormal choroidal neovascular network (choroidal neovascularization, CNV) beneath the neural retina. The newly formed blood vessels are excessively leaky. This leads to accumulation of subretinal fluid and blood leading to loss of visual acuity. Eventually, there is total loss of functional retina in the involved region, as a large disciform scar involving choroids and retina forms. While dry AMD patients may retain vision of decreased quality, wet AMD often results in blindness. (Hamdi & Kenney, Frontiers in Bioscience, e305-314. May 2003).

Diabetic Retinopathy

Diabetic retinopathy (DR) is recognized as a retinal vascular disorder exhibiting excess capillary permeability, vascular closure, and proliferation of new vessels. DR occurs in two stages: nonproliferative and proliferative, in the nonproliferative stage the disease is characterized by a loss of retinal capillary pericytes, thickening of the basement membrane and development of microaneurysms, dot-blot hemorrhages, and hard exudates. In the proliferative stage the disease is characterized by extensive neovascularization, vessel intrusion into the vitreous, bleeding and fibrosis with subsequent retinal traction, which leads to severe vision impairment. U.S. Pat. No. 6,740,738 and related patents and applications to the assignee of the present invention are directed to inhibition of RTP801 gene and protein, involved in retinopathy.

Oral Mucositis

Oral mucositis, also referred to as a stomatitis, is a common and debilitating side effect of chemotherapy and radiotherapy regimens, which manifests itself as erythema and painful ulcerative lesions of the mouth and throat, Routine activities such as eating, drinking, swallowing, and talking may be difficult or impossible for subjects with severe oral mucositis. Palliative therapy includes administration of analgesics and topical rinses.

Dry-Eye Syndrome

Dry eye syndrome is a common problem usually resulting from a decrease in the production of tear film that lubricates the eyes. Most patients with dry eye experience discomfort, and no vision loss; although in severe cases, the cornea may become damaged or infected. Wetting drops (artificial tears) may be used for treatment while lubricating ointments may help more severe cases.

More effective therapies to treat the above mentioned diseases and disorders would be of great therapeutic value.

SUMMARY OF THE INVENTION

The present invention provides inhibitors of a pro-apoptotic gene selected from the group consisting of TP53BP2, LRDD, CYBA, ATF3, CASP2, NOX3, HRK, CIQBP, BNIP3, MAPK8, MAPK14, RAC1, GSK3B, P2RX7, TRPM2, PARG, CD38, STEAP4, BMP2, CX43, TYROBP, CTGF, SPP1, RTN4R, ANXA2, RHOA, and DUOX1 (See Table A, infra, for genes' details). In various embodiments the inhibitor is selected from the group consisting of siRNA, shRNA, an aptamer, an antisense molecule, miRNA, a ribozyme, and an antibody. In the presently preferred embodiments the inhibitor is siRNA.

Accordingly, in one aspect the present invention provides novel double stranded oligoribonucleotides that inhibit expression of a pro-apoptotic gene selected from the group consisting of TP53BP2, LRDD, CYBA, ATF3, CASP2, NOX3, HRK, CIQBP, BNIP3, MAPK8, MAPK14, RAC1, GSK3B, P2RX7, TRPM2, PARG, CD38, STEAP4, BMP2, CX43, TYROBP, CTGF, SPP1. RHOA, and DUOX1. In some embodiments the gene is one of TPS3BP2, CASP2, NOX3, RAC1, RHOA, or DUOX1. In other embodiments the gene is one of LRDD, CYBA, HRK, BNIP3, CD38, BMP2, or SPP1. The invention also provides pharmaceutical compositions comprising one or more such oligoribonucleotides or a vector capable of expressing the oligoribonucleotide. The present invention further relates to methods for treating or preventing the incidence or severity of various diseases or conditions in a subject in need thereof wherein the disease or condition and/or symptoms associated therewith is selected from the group consisting of hearing loss, acute renal failure (ARF). glaucoma, acute respiratory distress syndrome (ARDS) and other acute lung and respiratory injuries, ischemia-reperfusion injury following lung transplantation, organ transplantation including lung, liver, heart, pancreas, and kidney transplantation, nephro- and neurotoxicity, spinal cord injury, pressure sores, age-related macular degeneration (AMD). dry eye syndrome, oral mucositis and chronic obstructive pulmonary disease (COPD). Such methods involve administering to a mammal in need of such treatment a prophylactically or therapeutically effective amount of one or more such compounds which inhibit or reduce expression or activity of at least one such gene.

In one aspect the present invention provides a compound having the structure:

5' $(N)_x$— Z 3' (antisense strand)
3' Z'—$(N')_y$ 5' (sense strand)

wherein each of N and N' is a nucleotide which may be modified or unmodified in its sugar residue;

wherein each of $(N)_x$ and $(N')_y$ is an oligonucleotide in which each consecutive N or N' is joined to the next N or N' by a covalent bond;

wherein each of x and y is an integer between 18 and 40:

wherein each of Z and Z' may be present or absent, but if present is 1-5 consecutive nucleotides covalently attached at the 3' terminus of the strand in which it is present; and wherein the sequence of $(N')_y$ is present within a mRNA whose sequence is set forth in any one of SEQ ID NOS:1-48. In one embodiment, the sequence of $(N')_y$ is present within a mRNA whose sequence is set forth in one of SEQ ID NO:1-41 or SEQ ID NO:46-48. The presently preferred genes are mammalian genes selected from the group consisting of TP53BP2 (SEQ ID NOS:1-2), LRDD (SEQ ID NOS:3-5), CYBA (SEQ ID NO:6), CASP2 (SEQ ID NOS:10-11), NOX3 (SEQ ID NO:12), HRK (SEQ ID NO:13), BNIP3 (SEQ ID NO:15), RAC1 (SEQ ID NOS:24-26), CD38 (SEQ ID NO:32), BMP2 (SEQ ID NO:34), SPP1 (SEQ ID NOS:39-41), RHOA (SEQ ID NO:46), and DUOX1 (SEQ ID NOS:47-48), SEQ ID NOS represent the mRNA sequences of the listed genes.

In some embodiments the covalent bond joining each consecutive N or N' is a phosphodiester bond. In various embodiments all the covalent bonds are phosphodiester bonds.

In various embodiments the compound comprises ribonucleotides wherein x=y and each of x and y is 19, 20, 21, 22 or 23. In some embodiments x=y=23. In other embodiments x=y=19.

In some embodiments the compound is blunt ended, for example wherein both Z and Z' are absent. In an alternative embodiment, the compound comprises at least one 3' overhang. wherein at least one of Z or Z' is present. Z and Z' can independently comprise one or more covalently linked modified or non-modified nucleotides, for example inverted dT or dA; dT, LNA, mirror nucleotide and the like. In some embodiments each of Z and Z' are independently selected from dT and dTdT.

In some embodiments N or N' comprises a modification in the sugar residue of one or more ribonucleotides. In other embodiments the compound comprises at least one ribonucleotide modified in the sugar residue. In some embodiments the compound comprises a modification at the 2' position of the sugar residue. In some embodiments the modification in the 2' position comprises the presence of an amino, a fluoro, an alkoxy or an alkyl moiety. In certain embodiments the 2' modification comprises methoxy moiety. A presently preferred modification is a 2' methoxy of the sugar residue (2'-O-methyl; 2'-O-Me: 2'-O—$CH_3$).

In some embodiments the compound comprises modified alternating ribonucleotides in one or both of the antisense and the sense strands. In certain embodiments the compound comprises modified alternating ribonucleotides in the antisense and the sense strands, in other embodiments the compound comprises modified alternating ribonucleotides in the antisense strand only. In certain embodiments the middle ribonucleotide of the antisense strand is not modified; e.g. ribonucleotide in position 10 in a 19-mer strand or position 12 in a 23-mer strand.

In additional embodiments the compound comprises modified ribonucleotides in alternating positions wherein each N at the 5' and 3' termini of $(N)_x$ are modified in their sugar residues. and each N' at the 5' and 3' termini of $(N')_y$ are unmodified in their sugar residues. In some embodiments, neither $(N)_x$ nor $(N')_y$ are phosphorylated at the 3' and 5' termini. In other embodiments either or both $(N)_x$ and $(N')_y$ are phosphorylated at the 3' termini.

In various embodiments the compound comprises an antisense sequence present in Tables B1-B76 (SEQ ID NOS:277 to 50970 and 50993-68654). In other embodiments the present invention provides a mammalian expression vector comprising an antisense sequence present in Tables B1-B76 (SEQ ID NOS:277 to 50970 and 50993-68654). In certain embodiments N and N' are selected from the oligomers set forth in any one of Tables C1, C2 or C3 (SEQ ID NOS: 97-276 and SEQ ID NOS: 50971-50992).

In certain embodiments the present invention provides a compound having the structure:
5' $(N)_x$—Z 3' (antisense strand)
3 Z'—$(N')_y$ 5' (sense strand)
wherein each of N and N' is a ribonucleotide which may be modified or unmodified in its sugar residue;
wherein each of $(N)_x$ and $(N')_y$ is an oligomer in which each consecutive N or N' is joined to the next N or N' by a covalent bond;
wherein each of x and y is an integer between 19 and 40:
wherein each of Z and Z' may be present or absent, but if present is 1-5 consecutive nucleotides covalently attached at the 3' terminus of the strand in which it is present; and
wherein the sequence of $(N')_y$ is present within an mRNA whose sequence is set forth in one of SEQ ID NO:46, SEQ ID NO:1-41 or SEQ ID NO:47-48.

In certain embodiments the present invention provides a compound having the structure:
5' $(N)_x$—Z 3' (antisense strand)
3' Z'—$(N')_y$ 5' (sense strand)
wherein each of N and N' is a ribonucleotide which may be modified or unmodified in its sugar residue;
wherein each of $(N)_x$ and $(N')_y$ is an oligomer in which each consecutive N or N' is joined to the next N or N' by a covalent bond;
wherein each of x and y is an integer between 19 and 40;
wherein each of Z and Z' may be present or absent, but if present is 1-5 consecutive nucleotides covalently attached at the 3' terminus of the strand in which it is present: and
wherein the sequence of $(N)_x$ and $(N')_y$ is set forth in any one of SEQ ID NOS: 277 to 50970 and 50993-68654.

In certain preferred embodiments, each of $(N)_x$ and $(N')_y$ is set forth in any one of SEQ ID NOS: 97-276 (Tables C1, C2) and SEQ ID NOS: 50971-50992 (Table C3).

In certain embodiments the present invention provides a compound having the structure:
5' $(N)_k$ 3' antisense strand
3' $(N')_y$ 5' sense strand
wherein each of N and N' is a nucleotide which may be modified or unmodified in its sugar residue;
wherein x=y=19 and the sequence of $(N)_x$ and $(N')_y$ are fully complementary;
wherein alternating ribonucleotides in $(N)_x$ and $(N')_y$ are modified to result in a 2'-O-methyl modification in the sugar residue of the ribonucleotides; wherein the ribonucleotides at the 5' and 3' termini of $(N)_x$ are modified;
wherein the ribonucleotides at the 5' and 3' termini of $(N')_y$ are unmodified;
wherein $(N)_x$ and $(N')_y$ are phosphorylated or non-phosphorylated at the 3' and 5' termini; and
wherein each of N and N' is selected from the group of oligomers set forth in Tables B1-B25 or B76 (SEQ ID NOS:277 to 15114 and SEQ ID NOS 68647-68654). In certain embodiments the N and N' are selected from the oligomers set forth in any one of Tables C1 and C3 (SEQ ID NOS: 97-266 (Table C1) and SEQ ID NOS: 50971-50992 (Table C3)).

In certain embodiments the present invention provides a compound having the structure
5' (N)x 3' antisense strand
3' (N')y 5' sense strand
wherein x=y=23 and the sequence of $(N)_x$ and $(N')_y$ are fully complementary;
wherein alternating ribonucleotides in $(N)_x$ and $(N')_y$ are modified to result in a 2'-O-methyl modification in the sugar residue of the ribonucleotides; wherein the ribonucleotides at the 5' and 3' termini of (N) are modified;
wherein the ribonucleotides at the 5' and 3' termini of $(N')_y$ are unmodified;
wherein $(N)_x$ and $(N')_y$ are phosphorylated or non-phosphorylated at the 3' and 5' termini; and
wherein each of N and N' is selected from the group of oligomers set forth in Tables B51-B75 (SEQ ID NOS: 30939 to 68646). In certain embodiments the N and N' are selected from the oligomers set forth in Table C2 (SEQ ID NOS: 267-276).

In a second aspect the present invention provides a pharmaceutical composition comprising one or more compounds of the present invention, in an amount effective to inhibit human gene expression wherein the gene is selected from the group consisting of TP53BP2, LRDD, CYBA, ATF3, CASP2, NOX3, HRK, CIQBP, BNIP3, MAPK, 8MAPK14, RAC1, GSK3B, P2RX7, TRPM2, PARG, CD38, STEAP4, BMP2, CX43, TYROBP, CTGF, SPP1, RTN4R, ANXA2 RHOA, and DUOX1; and a pharmaceutically acceptable carrier.

In another aspect, the present invention relates to a method for the treatment of a subject in need of treatment for a disease or disorder or symptoms associated with the disease or disorder, associated with the expression of a gene selected from TP53BP2, LRDD, CYBA, ATF3, CASP2, NOX3, HRK, CIQBP. BNIP3, MAPK5, MAPK14, RAC1, GSK3B, P2RX7, TRPM2, PARG, CD38. STEAP4. BMP2, CX43, TYROBP. CTGF, SPP1, RTN4R, ANXA2. RHOA, and DUOX1. comprising administering to the subject an amount of an siRNA which reduces or inhibits expression of at least one of those pro-apoptotic genes.

More specifically, the present invention provides methods and compositions useful in treating a subject suffering from acute renal failure (ARF), hearing loss, glaucoma, acute respiratory distress syndrome (ARDS) and other acute lung and respiratory injuries, injury (e.g. ischemia-reperfusion injury) in organ transplant including lung, kidney, bone marrow, heart, pancreas, cornea or liver transplantation, nephrotoxicity, spinal cord injury, pressure sores, dry eye syndrome, oral mucositis and chronic obstructive pulmonary disease (COPD). The methods of the invention comprise administering to the subject one or more inhibitory compounds which reduces, inhibits or down-regulate expression of a gene selected from the group consisting of TP53BP2, LRDD, CYBA, ATF3, CASP2, NOX3, HRK, CIQBP, BNIP3, MAPK8, MAPK14, RAC1, GSK3B, P2RX7, TRPM2, PARG, CD38, STEAP4, BMP2, CX43, TYROBP, CTGF, SPP1, RTN4R, ANXA2, RHOA, and DUOX1; and in particular siRNA in a therapeutically effective dose so as to thereby treat the patient.

In one embodiment, the present invention provides methods of treating a disease or condition selected from hearing loss, acute renal failure, glaucoma, acute respiratory distress syndrome, an acute lung injury, organ transplantation rejection, ischemia-reperfusion injury, nephrotoxicity, neurotoxicity, spinal cord injury, pressure sores, osteoarthritis, dry eye syndrome and chronic obstructive pulmonary disease (COPD), in a subject in need thereof, comprising administering to the subject an oligonucleotide which inhibits expression of a gene whose mRNA sequence is set forth in any one of SEQ ID NOS:1-41 or 46-48, in an amount effective to treat the disease or condition.

In one embodiment, the present invention provides methods of treating acute renal failure in a subject in need thereof, comprising administering to the subject an oligonucleotide which inhibits expression of any one of TP53BP (whose mRNA sequence is set forth in SEQ ID NOS:1-2); LRDD (whose mRNA sequence is set forth in SEQ ID NO:3-5); CYBA (whose mRNA sequence is set forth in SEQ ID NO:6), CASP2 (whose mRNA sequence is set forth in SEQ ID NO:10-11). BNIP3 (whose mRNA sequence is set forth in SEQ ID NO:15), or RAC1 (whose mRNA sequence is set forth in SEQ ID NO:24-26) in an amount effective to treat the acute renal failure.

In one embodiment, the present invention provides methods of treating spinal-cord injury in a subject in need thereof, comprising administering to the subject an oligonucleotide which inhibits expression of any one of RHOA (whose mRNA sequence is set forth in SEQ ID NO:46); TP53BP (whose mRNA sequence is set forth in SEQ ID NOS:1-2); LRDD (whose mRNA sequence is set forth in SEQ ID NO:3-5); CYBA (whose mRNA sequence is set forth in SEQ ID NO:6), CASP2 (whose mRNA sequence is set forth in SEQ ID NO:10-11), BNIP3 (whose mRNA sequence is set forth in SEQ ID NO:15), RAC1 (whose mRNA sequence is set forth in SEQ ID NO:24-26), CD38 (whose mRNA sequence is set forth in SEQ ID NO:32) or BMP2 (whose mRNA sequence is set forth in SEQ ID NO:34) in an amount effective to treat the spinal cord injury.

In one embodiment, the present invention provides methods of treating hearing loss in a subject in need thereof, comprising administering to the subject an oligonucleotide which inhibits expression of any one of TP53BP (whose mRNA sequence is set forth in SEQ ID NOS; 1-2); LRDD (whose mRNA sequence is set forth in SEQ ID NO:3-5); CYBA (whose mRNA sequence is set forth in SEQ ID NO:6). CASP2 (whose mRNA sequence is set forth in SEQ ID NO:10-1), NOX3 (whose mRNA sequence is set forth in SEQ ID NO:12), BNIP3 (whose mRNA sequence is set forth in SEQ ID NO:15), RAC1 (whose mRNA sequence is set forth in SEQ ID NO:24-26), CD38 (whose mRNA sequence is set forth in SEQ ID NO:32) or BMP2 (whose mRNA sequence is set forth in SEQ ID NO:34) in an amount effective to treat the hearing loss.

In one embodiment, the present invention provides methods of treating a disease or condition selected from chronic obstructive pulmonary disease, acute respiratory distress syndrome and acute lung injury in a subject in need thereof, comprising administering to the subject an oligonucleotide which inhibits expression of any one of LRDD (whose mRNA sequence is set forth in SEQ ID NO:3-5); CYBA (whose mRNA sequence is set forth in SEQ ID NO:6). CASP2 (whose mRNA sequence is set forth in SEQ ID NO:10-11), BNIP3 (whose mRNA sequence is set forth in SEQ ID NO: 15), RAC1 (whose mRNA sequence is set forth in SEQ ID NO:24-26). CD38 (whose mRNA sequence is set forth in SEQ IUD NO:32), BMP2 (whose mRNA sequence is set forth in SEQ ID NO:34), SPP1 (whose mRNA sequence is set forth in SEQ ID NOS:39-41) or DUOX (whose mRNA sequence is set forth in SEQ ID NOS:47-48) in an amount effective to treat the disease or condition.

In one embodiment, the present invention provides methods of treating a subject who is an organ transplant recipient or organ transplant donor comprising administering to the subject an oligonucleotide which inhibits expression of any one of TPS3BP (whose mRNA sequence is set forth in SEQ ID NOS:1-2); LRDD (whose mRNA sequence is set forth in SEQ ID NO:3-5); CYBA (whose mRNA sequence is set forth in SEQ ID NO:6), CASP2 (whose mRNA sequence is set forth in SEQ ID NO:10-11). BNIP3 (whose mRNA sequence is set forth in SEQ ID NO:15), RAC1 (whose mRNA sequence is set forth in SEQ ID NO:24-26). GSK3B (whose mRNA sequence is set forth in SEQ ID NO:27), P2RX7 (whose mRNA sequence is set forth in SEQ ID NO:28), TRPM2 (whose mRNA sequence is set forth in SEQ ID NO:30) or PARG (whose mRNA sequence is set forth in SEQ ID NO:31), in an amount effective to prevent rejection of the transplant.

In one embodiment, the present invention provides methods of treating glaucoma in a subject in need thereof, comprising administering to the subject an oligonucleotide which inhibits expression of any one of TP53BP (whose mRNA sequence is set forth in SEQ ID NOS:1-2); LRDD (whose mRNA sequence is set forth in SEQ ID NO:3-5); CYBA (whose mRNA sequence is set forth in SEQ ID NO:6), CASP2 (whose mRNA sequence is set forth in SEQ ID NO:10-11), BNIP3 (whose mRNA sequence is set forth in SEQ ID NO:15), RAC1 (whose mRNA sequence is set forth in SEQ ID NO:24-26), SPP1 (whose mRNA sequence is set forth in SEQ ID NOS:39-41), or RHOA (whose mRNA sequence is set forth in SEQ ID NO:46) in an amount effective to treat glaucoma.

In one embodiment, the present invention provides methods of treating oral mucositis in a subject in need thereof, comprising administering to the subject an oligonucleotide which inhibits expression of any one of TP538P (whose mRNA sequence is set forth in SEQ ID NOS:1-2); LRDD (whose mRNA sequence is set forth in SEQ ID NOS:3-5); CASP2 (whose mRNA sequence is set forth in SEQ ID NOS:10-11) or ATF3 (whose mRNA sequence is set forth in SEQ ID NOS:7-9) in an amount effective to treat oral mucositis.

In one embodiment, the present invention provides methods of treating osteoarthritis in a subject in need thereof, comprising administering to the subject an oligonucleotide which inhibits expression of SPP1 (whose mRNA sequence is set forth in SEQ ID NOS:39-41), in an amount effective to treat osteoarthritis.

In one embodiment, the present invention provides methods of treating dry eye syndrome in a subject in need thereof, comprising administering to the subject an oligonucleotide which inhibits expression of any one of TPS3BP (whose mRNA sequence is set forth in SEQ ID NOS:1-2); LRDD (whose mRNA sequence is set forth in SEQ ID NO:3-5); CYBA (whose mRNA sequence is set forth in SEQ ID NO:6). CASP2 (whose mRNA sequence is set forth in SEQ ID NO:10-11), BNIP3 (whose mRNA sequence is set forth in SEQ ID NO:15), or RAC1 (whose mRNA sequence is set forth in SEQ ID NO:24-26) in an amount effective to treat the syndrome.

In one embodiment, the present invention provides methods of treating a pressure sore in a subject in need thereof, comprising administering to the subject an oligonucleotide which inhibits expression of any one of CIQBP (whose mRNA sequence is set forth in SEQ ID NO:14). RAC1 (whose mRNA sequence is set forth in SEQ ID NOS:24-26), GSK3B (whose mRNA sequence is set forth in SEQ ID NO:27), P2RX7 (whose mRNA sequence is set forth in SEQ ID NO:28), TRPM2 (whose mRNA sequence is set forth in SEQ ID NO:30), PARG (whose mRNA sequence is set forth in SEQ ID NO:31), CD38 (whose mRNA sequence is set forth in SEQ ID NO:32). STEAP4 (whose mRNA sequence is set forth in SEQ ID NO:33), BMP2 (whose mRNA sequence is set forth in SEQ ID NO:34), GJA1 (whose mRNA sequence is set forth in SEQ ID NO:35), or TYROBP (whose mRNA sequence is set forth in SEQ ID NOS:36-37) in an amount effective to treat the pressure sore.

Lists of 19-mer, 21-met and 23-met sense and corresponding antisense sequences useful in preparation of siRNA compounds are set forth in SEQ ID NOS:277 to 50970 and 50993-68654, shown as sequence pairs in Table B, Tables B1-B76.

In one embodiment, the present invention provides methods of treating a disease or condition selected from hearing loss, acute renal failure, glaucoma, acute respiratory distress syndrome, an acute lung injury, organ transplantation rejection, ischemia-reperfusion injury, nephrotoxicity, neurotoxicity, spinal cord injury, pressure sores, osteoarthritis and chronic obstructive pulmonary disease (COPD), in a subject in need thereof, comprising administering to the subject an antibody which inhibits a polypeptide whose sequence is set forth in any one of SEQ ID NOS: 90-93 in an amount effective to treat the disease or condition.

In one embodiment, the present invention provides a pharmaceutical composition comprising an antibody which inhibits a polypeptide whose sequence is set forth in any one of SEQ ID NOS: 90-93, in an amount effective to inhibit the polypeptide, and a pharmaceutically acceptable carrier.

In one embodiment, the present invention relates to the use of a therapeutically effective dose of an oligonucleotide for the preparation of a composition for treating a subject suffering from a disease or condition selected from hearing loss, acute renal failure. glaucoma, acute respiratory distress syndrome, an acute lung injury, organ transplantation rejection, ischemia-reperfusion injury, nephrotoxicity, neurotoxicity, spinal cord injury, pressure sores, osteoarthritis and chronic obstructive pulmonary disease (COPD), wherein the oligonucleotide inhibits expression of a gene whose mRNA sequence is set forth in any one of SEQ ID NOS:1-41 or 46-48.

In one embodiment, the present invention relates to the use of a therapeutically effective dose of an antibody for the preparation of a composition for treating a subject suffering from a disease or condition selected from hearing loss, acute renal failure, glaucoma, acute respiratory distress syndrome, an acute lung injury, organ transplantation rejection, ischemia-reperfusion injury, nephrotoxicity, neurotoxicity, spinal cord injury, pressure sores, osteoarthritis and chronic obstructive pulmonary disease (COPD), wherein the antibody inhibits a polypeptide whose sequence is set forth in any one of SEQ ID NOS: 90-93.

DETAILED DESCRIPTION OF THE INVENTION

The present invention relates generally to compounds which down-regulate expression of various genes including pro-apoptotic genes, particularly to novel small interfering RNAs (siRNAs), and to the use of these novel siRNAs in the treatment of various diseases and medical conditions. Particular diseases and conditions to be treated are hearing loss, acute renal failure (ARF), glaucoma, acute respiratory distress syndrome (ARDS) and other acute lung and respiratory injuries, ischemia-reperfusion injury following lung transplantation. organ transplantation including lung, liver, heart, bone marrow, pancreas, cornea and kidney transplantation, spinal cord injury, pressure sores, age-related macular degeneration (AMD), dry eye syndrome, oral mucositis and chronic obstructive pulmonary disease (COPD). Other indications include chemical-induced nephrotoxicity and chemical-induced neurotoxicity, for example toxicity induced by cisplatin and cisplatin-like compounds, by aminoglycosides, by loop diuretics, and by hydroquinone and their analogs.

Lists of preferred siRNA to be used in the present invention are provided in Table B, SEQ ID NOS:277 to 50970 and 50993-68654. For each gene there is a separate list of 19-mer. 21-mer and 23-mer sequences, which are prioritized based on their score in the proprietary algorithm as the best sequences for targeting the human gene expression. 21- or 23-mer siRNA sequences can also be generated by 5' and/or 3' extension of the 19-mer sequences disclosed herein. Such extension is preferably complementary to the corresponding mRNA sequence. Certain 23-mer oligomers were devised by this method where the order of the prioritization is the order of the corresponding 19-mer.

Methods, molecules and compositions which inhibit the pro-apoptotic genes of the invention are discussed herein at length, and any of said molecules and/or compositions may be beneficially employed in the treatment of a subject suffering from any of said conditions.

Where aspects or embodiments of the invention are described in terms of Markush groups or other grouping of alternatives, those skilled in the an will recognize that the invention is also thereby described in terms of any individual member or subgroup of members of the group.

Prospoptotic Genes

A "pro-apoptotic gene" is generally defined as a gene that plays a positive role in apoptotic cell death. For the purposes of this application, preferred pro-apoptotic genes and the preferred uses of siRNA or other inhibitors of these pro-apoptotic genes are listed in Table A below. It should be noted that whereas the compounds of the present invention are useful in treating the listed indications, certain compounds may be more effective in a particular tissue than in another. Those preferred indications are listed in Table A, hereinbelow.

TABLE A

Preferred genes of the present invention

| No. | Gene | Full name and Human Gene ID | Preferred diseases/conditions |
|---|---|---|---|
| 1 | TP53BP2 | tumor protein p53 binding protein, 2<br>gi\|112799848\|ref\|NM_001031685.2 (SEQ ID NO: 1)<br>gi\|112799845\|ref\|NM_005426.2 (SEQ ID NO: 2): | ARF, nephrotoxicity, glaucoma, dry eye, kidney transplantation hearing loss, acoustic trauma, oral mucositis |
| 2 | LRDD | leucine-rich repeats and death domain containing<br>gi\|61742781\|ref\|NM_018494.3 (SEQ ID NO: 3)<br>gi\|61742783\|ref\|NM_145886.2 (SEQ ID NO: 4)<br>gi\|61742785\|ref\|NM_145887.2 (SEQ ID NO: 5) | ARF, glaucoma, hearing loss, spinal-cord injury, oral mucositis; kidney or lung transplantation, and ischemic-reperfusion lung injury, dry eye |
| 3 | CYBA | cytochrome b-245, alpha polypeptide<br>gi\|68509913\|ref\|NM_000101.2\|(SEQ ID NO: 6) | ARF, ARDS, hearing loss, spinal-cord injury, glaucoma, kidney transplantation, lung transplantation and ischemic-reperfusion lung injury |
| 4 | ATF3 | activating transcription factor 3<br>gi\|95102484\|ref\|NM_001030287.2\| (SEQ ID NO: 7)<br>gi\|71902534\|ref\|NM_001674.2\|(SEQ ID NO: 8)<br>gi\|95102480\|ref\|NM_004024.4\|(SEQ ID NO: 9) | ARF, glaucoma, hearing loss, spinal-cord injury, oral mucositis |
| 5 | CASP2 | caspase 2, apoptosis-related cysteine peptidase<br>gi\|39995058\|ref\|NM_032982.2 (SEQ ID NO: 10)<br>gi\|39995060\|ref\|NM_032983.2 (SEQ ID NO: 11) | ARF, glaucoma, hearing loss, spinal-cord injury, kidney transplantation, lung transplantation and ischemic-reperfusion lung injury, oral mucositis, dry eye |
| 6 | NOX3 | NADPH oxidase 3<br>gi\|11136625\|ref\|NM_015718.1 gi\| (SEQ ID NO: 12) | Hearing loss, acoustic trauma |
| 7 | HRK | harakiri, BCL2 interacting protein (contains only BH3 domain)<br>gi\|4504492\|ref\|NM_003806.1 (SEQ ID NO: 13) | ARF, glaucoma, hearing loss, spinal-cord injury, ARDS |
| 8 | C1QBP | complement component 1, q subcomponent binding protein<br>gi\|28872801\|ref\|NM_001212.3 (SEQ ID NO: 14) | ARF, COPD, hearing loss, spinal-cord injury, pressure sores |
| 9 | BNIP3 | BCL2/adenovirus E1B 19 kDa interacting protein 3<br>gi\|7669480\|ref\|NM_004052.2 (SEQ ID NO: 15) | ARF, glaucoma, hearing loss, acoustic trauma, spinal-cord injury, ARDS, COPD, lung transplantation and ischemic-reperfusion lung injury |
| 10 | MAPK8 | mitogen-activated protein kinase 8<br>gi\|20986493\|ref\|NM_002750.2(SEQ ID NO: 16)<br>gi\|20986522\|ref\|NM_139049.1(SEQ ID NO: 17)<br>gi\|20986518\|ref\|NM_139046.1(SEQ ID NO: 18)<br>gi\|20986520\|ref\|NM_139047.1\| (SEQ ID NO: 19) | ARF, glaucoma, hearing loss, spinal-cord injury, ARDS |
| 11 | MAPK14 | mitogen-activated protein kinase 14<br>gi\|20986511\|ref\|NM_139012.1(SEQ ID NO: 20)<br>gi\|20986515\|ref\|NM_139014.1(SEQ ID NO: 21)<br>gi\|4503068\|ref\|NM_001315.1(SEQ ID NO: 22)<br>gi\|20986513\|ref\|NM_139013.1(SEQ ID NO: 23) | ARF, glaucoma, hearing loss, spinal-cord injury, ARDS |
| 12 | Rac1 | ras-related C3 botulinum toxin substrate 1 (rho family, small GTP binding protein)<br>gi\|38505164\|ref\|NM_198829.1(SEQ ID NO: 24)<br>gi\|156071511\|ref\|NM_018890.3(SEQ ID NO: 25)<br>gi\|156071503\|ref\|NM_006908.4(SEQ ID NO: 26) | ARF, glaucoma, hearing loss, acoustic trauma, spinal-cord injury, ARDS, lung transplantation and ischemic-reperfusion lung injury, AMD, pressure sores |
| 13 | GSK3B | glycogen synthase kinase 3 beta<br>gi\|21361339\|ref\|NM_002093.2(SEQ ID NO: 27) | ARF, hearing loss, spinal-cord injury, COPD, pressure sores, ARDS, transplantation |
| 14 | P2RX7 | purinergic receptor P2X, ligand-gated ion channel, 7<br>gi\|34335273\|ref\|NM_002562.4 (SEQ ID NO: 28) | ARF, hearing loss, spinal-cord injury, COPD, pressure sores, ARDS, transplantation |
| 15 | TRPM2 | transient receptor potential cation channel, subfamily M, member 2<br>gi\|67906811\|ref\|NM_001001188.3 (SEQ ID NO: 29)<br>gi\|67906812\|ref\|NM_003307.3 (SEQ ID NO: 30) | ARF, hearing loss, spinal-cord injury, COPD, pressure sores, ARDS, transplantation |

TABLE A-continued

Preferred genes of the present invention

| No. | Gene | Full name and Human Gene ID | Preferred diseases/conditions |
|---|---|---|---|
| 16 | PARG | poly (ADP-ribose) glycohydrolase<br>gi\|70610135\|ref\|NM_003631.2 (SEQ ID NO: 31) | ARF, hearing loss, spinal-cord injury, COPD, pressure sores, ARDS, transplantation |
| 17 | CD38 | CD38 molecule<br>gi\|38454325\|ref\|NM_001775.2 (SEQ ID NO: 32) | ARF, hearing loss, spinal-cord injury, COPD, pressure sores |
| 18 | STEAP4 | STEAP family member 4<br>gi\|13375867\|ref\|NM_024636.1 (SEQ ID NO: 33) | ARF, hearing loss, spinal-cord injury, COPD, pressure sores |
| 19 | BMP2 | bone morphogenetic protein 2<br>gi\|80861484\|ref\|NM_001200.2(SEQ ID NO: 34) | ARF, hearing loss, spinal-cord injury, COPD, pressure sores |
| 20 | GJA1 | gap junction protein, alpha 1, 43 kDa<br>gi\|4755136\|ref\|NM_000165.2(SEQ ID NO: 35) | ARF, hearing loss, spinal-cord injury, COPD, pressure sores |
| 21 | TYROBP | TYRO protein tyrosine kinase binding protein<br>gi\|38157998\|ref\|NM_003332.2(SEQ ID NO: 36)<br>gi\|38158004\|ref\|NM_198125.1 (SEQ ID NO: 37) | ARF, hearing loss, spinal-cord injury, COPD, pressure sores |
| 22 | CTGF | connective tissue growth factor<br>gi\|4503122\|ref\|NM_001901.1(SEQ ID NO: 38) | ARF, hearing loss, spinal-cord injury, COPD |
| 23 | SPP1 | secreted phosphoprotein 1<br>gi\|91206461\|ref\|NM_001040058.1 SEQ ID NO: 39)<br>gi\|38146097\|ref\|NM_000582.2 (SEQ ID NO: 40)<br>gi\|91598938\|ref\|NM_001040060.1 (SEQ ID NO: 41) | ARF, glaucoma, ARDS, osteoarthritis |
| 24 | RTN4R | reticulon 4 receptor<br>gi\|47519383\|ref\|NM_023004.5 (SEQ ID NO: 42) | spinal-cord injury |
| 25 | ANXA2 | annexin A2<br>gi\|50845387\|ref\|NM_001002858.1\| (SEQ ID NO: 43) gi\|50845389\|ref\|NM_004039.2\| (SEQ ID NO: 44) gi\|4757756\|ref\|NP_004030.1 (SEQ ID NO: 45) | ARF, hearing loss, spinal-cord injury, COPD |
| 26 | RHOA | ras homolog gene family member A<br>gi\|50593005\|ref\|NM_001664.2(SEQ ID NO: 46)\| | spinal-cord injury, glaucoma |
| 27 | DUOX1 | dual oxidase 1<br>gi\|28872749\|ref\|NM_017434.3(SEQ ID NO: 47)<br>gi\|28872750\|ref\|NM_175940.1(SEQ ID NO: 48) | Acute Respiratory Distress Syndrome, COPD |

ARDS: acute respiratory distress syndrome;
AMD: age-related macular degeneration;
COPD: Chronic obstructive pulmonary disease;
ARF: acute renal failure Table A comprises the polynucleotide SEQ ID NOS of the mRNA of the genes targeted by the compounds of the present invention (set forth as SEQ ID NOS:1-48). The corresponding polypeptides are set forth in SEQ ID NOS: 49-96. The genes listed in Table A, supra, are described in more detail as follows:

(1) Tumor Protein p53 Binding Protein, 2 (TP53BP2):

Gene Aliases: BBP; 53BP2; ASPP2; p53BP2; PPP1R13A, A1746547, X98550

This gene encodes a member of the ASPP (apoptosis-stimulating protein of p53) family of p53 interacting proteins. The corresponding protein contains four ankyrin repeats and an SH3 domain involved in protein-protein interactions. It is localized to the perinuclear region of the cytoplasm, and regulates apoptosis and cell growth through interactions with other regulatory molecules including members of the p53 family. Multiple transcript variants encoding different isoforms have been found for this gene. The polynucleotide sequences of human TP53BP2 mRNA transcriptional variants 1 and 2 are SEQ ID NOS:1 and 2, respectively, and the corresponding polypeptide sequence are set forth in SEQ ID NOS:49-50, respectively.

(2) Leucine-Rich Repeats and Death Domain Containing (LRDD)

Gene aliases: PIDD; MGC16925; DKFZp434D229, 1200011D09Rik, AU042446

The protein encoded by this gene contains a leucine-rich repeat and a death domain. This protein has been shown to interact with other death domain proteins, such as Fas (TNFRSF6)-associated via death domain (FADD) and MAP-kinase activating death domain-containing protein (MADD), and thus may function as an adaptor protein in cell death-related signaling processes. The expression of the mouse counterpart of this gene has been found to be positively regulated by the tumor suppressor p53 and to induce cell apoptosis in response to DNA damage, which suggests a role for this gene as an effector of p53-dependent apoptosis. Three alternatively spliced transcript variants encoding distinct isoforms have been reported. The polynucleotide sequence of human LRDD transcriptional variants 2, 1 and 3 are set forth in SEQ ID NOS: 3-5, respectively, and the corresponding polypeptide sequence are set forth in SEQ ID NOS:51-53, respectively.

International Patent Publication WO 01/18037 discloses the LRDD polynucleotide and polypeptide sequences. International Patent Publication WO 03/087368 teaches compositions and methods for inhibiting genes.

(3) Cytochrome b-245, Alpha Polypeptide (CYBA)

Gene aliases: cytochrome b light chain; cytochrome b(558) alpha-subunit; cytochrome b. alpha polypeptide; flavocytochrome b-558 alpha polypeptide; p22-phox.

Cytochrome b is comprised of a light chain (alpha) and a heavy chain (beta). This gene encodes the light, alpha subunit which has been proposed as a primary component of the microbicidal oxidase system of phagocytes. Mutations in this gene are associated with autosomal recessive chronic granulomatous disease (CGD), that is characterized by the failure of activated phagocytes to generate superoxide, which is important for the microbicidal activity of these cells. The polynucleotide sequence of human CYBA mRNA is depicted as SEQ ID NO:6, and the corresponding polypeptide sequence is set forth in SEQ ID NO:54.

International Patent Publication WO 2005/103297 teaches modulation of p22phox activity.

(4) Activating Transcription Factor 3 (ATF3)

Gene aliases: ATF3deltaZip2; ATF3deltaZip2c; ATF3deltaZip3. LRG-21, LRF-1

ATF3 is a member of the mammalian activation transcription factor/cAMP responsive element-binding (CREB) protein family of transcription factors. Multiple transcript variants encoding two different isoforms have been found for this gene. The longer isoform represses rather than activates transcription from promoters with ATF binding elements. The shorter isoform (deltaZip2) lacks the leucine zipper protein-dimerization motif and does not bind to DNA, and it stimulates transcription presumably by sequestering inhibitory co-factors away from the promoter. It is possible that alternative splicing of the ATF3 gene may be physiologically important in the regulation of target genes. The polynucleotide sequences of human ATF3 transcriptional variants 3, 1 and 2 are set forth in SEQ ID NOS: 7-9, respectively, and the corresponding polypeptide sequences are set forth in SEQ ID NOS:55-57, respectively.

US Patent Publication 2003/0125277 teaches antisense to ATF3. International Patent Publication WO 2005/103297 relates to the methods of treating neuronal disease.

(5) Caspase 2, Apoptosis-Related Cysteine Peptidase (Neural Precursor Cell Expressed, Developmentally Down-Regulated 2 (CASP2)

Gene aliases: CASP-2, ICH-1L, ICH-1L/1S, ICH1, NEDD2; ICH-1 protease; NEDD2 apoptosis regulatory gene; caspase 2, apoptosis-related cysteine protease.

This gene encodes a protein, which is a member of the cysteine-aspartic acid protease (caspase) family. Sequential activation of caspases plays a central role in the execution-phase of cell apoptosis. Caspases exist as inactive proenzymes, which undergo proteolytic processing at conserved aspartic residues to produce two subunits, large and small, that dimerize to form the active enzyme. The proteolytic cleavage of this protein is induced by a variety of apoptotic stimuli. Alternative splicing of this gene results in multiple transcript variants that encode different isoforms. The polynucleotide sequences of human CASP2 transcriptional variants 1 and 3 are set forth in SEQ ID NOS:10-11, respectively, and the corresponding polypeptide sequences are set forth in SEQ U) NOS:58-59, respectively.

U.S. Pat. No. 6,083,735 relates to the alternative splicing products of Casp2. U.S. Pat. Nos. 5,929,042 and 7,223,856 disclose specific Casp2 antisense compounds for the treatment of neurodegenerative disorders. International Patent Publication WO 02/024720 teaches Casp2 antisense. International Patent Publication WO 02/034201 discloses methods of treating diabetic retinopathy; WO 03/05821 relates to the inhibition of apoptosis related genes; WO 2004/009797 teaches Casp2 antisense; and WO 20041103389 relates to methods for preventing cell death.

(6) NADPH Oxidase 3 (NOX3)

Gene aliases: GP91-3, MGC124289, Het, Nmf250; NADPH oxidase catalytic subunit-like 3. NADPH oxidase 1; head-tilt NADPH oxidases, such as NOX3, are plasma membrane-associated enzymes found in many cell types. They catalyze the production of superoxide by a 1-electron reduction of oxygen, using NADPH as the electron donor. The polynucleotide sequence of human NOX3 mRNA is set forth in SEQ ID NO: 12, and the corresponding polypeptide sequence is set forth in SEQ ID NO:60.

International Patent Publication WO 2005/119251 relates to a method of treating hearing loss.

(7) Harakiri, BCL2 Interacting Protein (Contains Only BH3 Domain) (HRK)

Gene aliases: DP5, Bid3; BCL2-interacting protein; activator of apoptosis Hrk; BH3 interacting (with BCL2 family) domain, apoptosis agonist.

As an activator of apoptosis, Hrk regulates apoptosis through interaction with death-repressor proteins Bcl-2 and Bcl-X(L). The HRK protein lacks significant homology to other BCL2 family members except for an 8-amino acid region that was similar to the BCL2 homology domain-3 (BH3) motif of BIK. HRK interacts with BCL2 and BCLXL via the BH3 domain, but not with the death-promoting BCL2-related proteins BAX, BAK, or BCLXS. HRK localizes to membranes of intracellular organelles in a pattern similar to that previously reported for BCL2 and BCLXL. The polynucleotide sequence of human HRK mRNA is set forth in SEQ ID NO: 13 and the corresponding polypeptide sequence is set forth in SEQ ID NO.61.

(8) Complement Component 1, q Subcomponent Binding Protein (C1QBP)

Gene aliases: GC1QBP, HABP1, SF2p32, gC1Q-R, gC1qR, p32, RP23-83I13.1, AA407365, AA986492, D11Wsu182e, MGC91723; C1q globular domain-binding protein; hyaluronan-binding protein 1; splicing factor SF2-associated protein.

The human complement subcomponent C1q associates with C1r and C1s in order to yield the first component of the serum complement system. The protein encoded by this gene is known to bind to the globular heads of C1q molecules and inhibit C1 activation. This protein has also been identified as the p32 subunit of pre-mRNA splicing factor SF2, as well as a hyaluronic acid-binding protein. The polynucleotide sequence of human CIQBP mRNA is set forth in SEQ ID NO: 14 and the corresponding polypeptide sequence is set forth in SEQ ID NO:62.

(9) BCL2/Adenovirus E1B 19 kDa Interacting Protein 3 (BNIP3)

Gene aliases: NIP3, MGC93043; BCL2/adenovirus E1B 19kD-interacting protein 3, BCL2/adenovirus E1B 19 kDa-interacting protein 3 nuclear gene for mitochondrial product.

This gene is a member of the BCL2/adenovirus E1B 19 kd-interacting protein (BNIP) family. It interacts with the E1B 19 kDa protein, which is responsible for the protection of virally-induced cell death, as well as E18 19 kDa-like sequences of BCL2, also an apoptotic protector. This gene contains a BH3 domain and a transmembrane domain, which have been associated with pro-apoptotic function. The dimeric mitochondrial protein encoded by this gene is known to induce apoptosis, even in the presence of BCL2. The polynucleotide sequence of human BNIP3 mRNA is set forth in SEQ ID NO:15and the corresponding polypeptide sequence is set forth in SEQ ID NO:63.

U.S. Pat. No. 5,858,678 relates to the BNIP3 polynucleotide and polypeptide sequences. International Patent Publication WO 2004/009780 discloses methods of preventing ischemia induced cell damage.

(10) Mitogen-Activated Protein Kinase 8 (MAPK8)

Gene aliases: JNK; JNK1; PRKM8; SAPK1; JNK1A2; JNK21B1/2; JNK1 alpha protein kinase, JNK1 beta protein kinase; c-Jun N-terminal kinase 1; mitogen-activated protein kinase 8 transcript variant 2; protein kinase JNK1; stress-activated protein kinase JNK1.

The protein encoded by this gene is a member of the MAP kinase family. MAP kinases act as an integration point for multiple biochemical signals, and are involved in a wide variety of cellular processes such as proliferation, differentiation, transcription regulation and development. This kinase is activated by various cell stimuli, and targets specific transcription factors, and thus mediates immediate-early gene expression in response to cell stimuli. The activation of this kinase by tumor-necrosis factor alpha (TNF-α) is found to be required for TNF-α induced apoptosis. This kinase is also involved in UV radiation induced apoptosis, which is thought to be related to cytochrome c-mediated cell death pathway. Studies of the mouse counterpart of this gene suggested its role in T cell proliferation, apoptosis and differentiation. Four alternatively spliced transcript variants encoding distinct isoforms have been reported. The polynucleotide sequence of MAPK8 transcriptional variants 2, 1, 3 and 4 are set forth in SEQ ID NOS:16-19 respectively and the corresponding polypeptide sequences are set forth in SEQ ID NO:64-67.

International Patent Publication WO 99/09214 and U.S. Pat. No. 5,877,309 disclose antisense to INK family members.

(11) Mitogen-Activated Protein Kinase 14 (MAPK14)

Gene aliases: CSBP1; CSBP2; CSPB1; EXIP; Mxi2; PRKM14; PRKM15; RK; SAPK2A; p38; p38ALPHA; MGC102436; p38MAPK; CSBP; Exip; Hog; MGC105413; p38Hog: Csaids binding protein; MAP kinase Mxi2; MAX-interacting protein 2; cytokine suppressive anti-inflammatory drug binding protein; p38 MAP kinase: p38 mitogen activated protein kinase; p38alpha Exip; stress-activated protein kinase 2A, trna synthetase cofactor p38.

The protein encoded by this gene is a member of the MAP kinase family, which act as an integration point for multiple biochemical signals, and are involved in a wide variety of cellular processes such as proliferation, differentiation, transcription regulation and development. This kinase is activated by various environmental stresses and proinflammatory cytokines. The activation requires its phosphorylation by MAP kinase kinases (MKKs), or its autophosphorylation triggered by its interaction with MAP3K7IP1/TAB1 protein. The substrates of this kinase include transcription regulator ATF2, MEF2C, and MAX, cell cycle regulator CDC25B, and tumor suppressor p53, which suggest its role in stress related transcription and cell cycle regulation, as well as in genotoxic stress response. Four alternatively spliced transcript variants of this gene encoding distinct isoforms have been reported. The polynucleotide sequence of human MAPK14 transcriptional variants 2, 4, 1 and 3 are set forth in SEQ ID NOS:20-23, respectively and the corresponding polypeptide sequences are set forth in SEQ ID NO:68-71.

International Patent Publications WO 2000/59919 and WO 2005/016947 and U.S. Pat. Nos. 6,140,124 and 6,448,079 teach antisense inhibition of p38.

(12) Ras-Related C3 Botulinum Toxin Substrate 1 (Rho Family, Small GTP Blading Protein Rac1; RAC1)

Gene aliases: MGC111543, MIG5, TC-25, p21-Rac1; migration-inducing gene 5: migration-inducing protein 5; ras-related C3 botulinum toxin substrate 1; rho family, small GTP binding protein Rac1, ms-related C3 botulinum toxin substrate 1 (rho family small GTP binding protein Rac1)

The protein encoded by this gene is a GTPase, which belongs to the RAS superfamily of small GTP-binding proteins. Members of this superfamily regulate a diverse array of cellular events, including the control of cell growth, cytoskeletal reorganization, and the activation of protein kinases. Several alternatively spliced transcript variants of this gene have been described, but the full-length nature of some of these variants has not been determined. The polynucleotide sequences of human RAC1 transcriptional variants 1c, 1b and 1 are set forth in SEQ ID NOS:24-26, respectively and the corresponding polypeptide sequences are set forth in SEQ ID NO:72-74.

U.S. Pat. No. 6,180,597 relates to rho GTPase inhibitors that increase endothelial cell nitric oxide synthase levels. International Patent Publication WO 01/15739 teaches antisense modulation of Rho family members. International Patent Publication WO 2004/042052 teaches methods of suppressing TNF-α secretion.

(13) Glycogen Synthase Kinase 3 Beta (GSK3B)

Gene aliases: 7330414F15Rik, 8430431H08Rik, C86142, GSK-3, GSK-3beta, GSK3

Glycogen synthase kinase-3 (GSK3) is a proline-directed serine-threonine kinase that was initially identified as a phosphorylating and inactivating glycogen synthase. Two isoforms, alpha (GSK3A; MIM 606784) and beta, show a high degree of amino acid homology (Stambolic and Woodgett, Biochem J. 1994 303(Pt 3):701-4). GSK3B is involved in energy metabolism, neuronal cell development, and body pattern formation (Plyte et al., Biochim Biophys Acta. 1992, 1114(2-3):147-62). The polynucleotide sequence of human GSK3B mRNA is set forth in SEQ ID NO:27, and the corresponding polypeptide sequence is set forth in SEQ ID NO:75.

U.S. Pat. No. 6,323,029 relates to antisense inhibition of GSK3B.

(14) Purinergic Receptor P2X, Ligand-Gated Ion Channel, 7 (P2RX7)

Gene aliases: MGC20089, P2X7, A1467586; ATP receptor; P2X purinoceptor 7; P2X7 receptor; P2Z receptor, purinergic receptor P2X7.

The product of this gene belongs to the family of purinoceptors for ATP. This receptor functions as a ligand-gated ion channel and is responsible for ATP-dependent lysis of macrophages through the formation of membrane pores permeable to large molecules. Activation of this nuclear receptor by ATP in the cytoplasm may be a mechanism by which cellular activity can be coupled to changes in gene expression. Multiple alternatively spliced variants which would encode different isoforms have been identified although some fit nonsense-mediated decay (NMD) criteria. The polynucleotide sequence of human P2RX7 mRNA is set forth in SEQ ID NO:28 and the corresponding polypeptide sequence is set forth in SEQ ID NO:76.

(15) Transient Receptor Potential Cation Channel, Subfamily M, Member 2 (TRPM2)

Gene aliases: EREG1, KNP3, LTRPC2, MGC133383, NUDT9H, NUDT9L1, TRPC7, 9830168K16Rik, C79133, Trp7, Trrp7; estrogen responsive element associated gene 1; long transient receptor potential channel 2; transient receptor potential channel 7, transient receptor potential cation channel, subfamily M, member 2 (Trpm2): transient receptor potential channel 7; transient receptor protein 7.

The protein encoded by this gene is a calcium-permeable cation channel that is regulated by free intracellular ADP-ribose. The encoded protein is activated by oxidative stress and confers susceptibility to cell death. The polynucleotide sequences of the human TRPM2 is set forth in SEQ ID NO:29 and the corresponding polypeptide sequences is set forth in SEQ ID NO:77. (Two transcript variants encoding different isoforms S and L had been found for this gene. The S variant was removed by NCBI since it contains a sequencing error and does not exist).

(16) Poly (ADP-Ribose) Glycohydrolase (PARG)

Gene aliases: PARG99; poly(ADP-ribose) glycohydrolase

Poly(ADP-ribose) glycohydrolase (PARG) is the major enzyme responsible for the catabolism of poly(ADP-ribose), a reversible covalent-modifier of chromosomal proteins. The protein is found in many tissues and may be subject to proteolysis generating smaller, active products. The polynucleotide sequence of human PARG mRNA is set forth in SEQ ID NO:31, and the corresponding polypeptide sequence is set forth in SEQ ID NO:79.

(17) CD38 Molecule (CD38)

Gene aliases: T10, Cd38-Rs1; ADP-ribosyl cyclase/cyclic ADP-ribose hydrolase; CD38 antigen; CD38 antigen (p45): cyclic ADP-ribose hydrolase.

CD38 is a novel multifunctional ectoenzyme widely expressed in cells and tissues: especially in leukocytes. CD38 also functions in cell adhesion, signal transduction and calcium signaling. The polynucleotide sequence of human CD38 mRNA is set forth in SEQ ID NO: 32, and the corresponding polypeptide sequences are set forth in SEQ ID NO:80.

(18) STEAP Family Member 4 (STEAP4)

Gene aliases: DKFZp666D049, FL123153, STAMP2, TIARP, TNFAIP9, 1110021O17Rik, AI481214, dudulin 4; six transmembrane prostate protein 2; tumor necrosis factor, alpha-induced protein 9: tumor necrosis-alpha-induced adipose-related protein, m TNFa-induced adipose-related protein; tumor necrosis factor, alpha-induced protein 9.

A membrane protein induced by TNF-α and IL-6 in adipose tissues. Both IL-6 and TNF-α were shown to be unregulated in a spinal cord injury model (Ahn, et al., BBRC 2006 348(2):560-70) and are thought to promote apoptotic events. The polynucleotide sequence of human STEAP4 mRNA is set forth in SEQ ID NO:33, and the corresponding polypeptide sequence is set forth in SEQ ID NO:81.

(19) Bone Morphogenetic Protein 2 (BMP2)

Gene aliases: BMP2A, A1467020, BC069214CR618407, M22489

The protein encoded by this gene belongs to the transforming growth factor-beta (TGFB) superfamily. The encoded protein acts as a disulfide-linked homodimer and induces bone and cartilage formation. The polynucleotide sequence of human BMP2 mRNA is set forth in SEQ ID NO:34, and the corresponding polypeptide sequence is set forth in SEQ ID NO:82.

International Patent publication WO 2005/041857, coassigned to the assignee of the present application, relates to BMP inhibition for the treatment of ischemia and neurological disease.

(20) Gap Junction Protein, Alpha 1, 43 kDa (Connexin 43, GJA1)

Gene aliases: CX43, DFNB38, GJAL, ODD, ODDD, ODOD, SDTY3, MGC93610, AU042049, AW546267, Cnx43, Cx43alpha1, Gja-1, Npm1, gap junction protein, alpha-like; oculodentodigital dysplasia (syndactyly type III), gap junction protein alpha 1 43 kD; gap junction protein, alpha 1, 43 kD, alpha 1 connexin.

Gap junction protein, alpha 1 is a member of the connexin gene family of proteins and is a component of gap junctions in the heart, and is believed to have a crucial role in the synchronized contraction of the heart and in embryonic development. Connexin 43 is targeted by several protein kinases that regulate myocardial cell-cell coupling. A related intron-less connexin 43 pseudogene, GJA1P, has been mapped to chromosome 5. The polynucleotide sequence of human GJA1 mRNA is set forth in SEQ ID NO:35, and the corresponding polypeptide sequence is set forth in SEQ ID NO:83. U.S. Pat. No. 7,098,190 teaches antisense compounds for treating, inter alia, wounds and spinal cord injury.

(21) TYRO Protein Tyrosine Kinase Binding Protein (TYROBP)

Gene Aliases: DAP12, KARAP, PLOSL, Ly83; DNAX-activation protein 12; killer activating receptor associated protein.

This gene encodes a transmembrane signaling polypeptide that contains an immunoreceptor tyrosine-based activation motif (ITAM) in its cytoplasmic domain. The protein may associate with the killer-cell inhibitory receptor (KIR) family of membrane glycoproteins and may act as an activating signal transduction element. This protein may bind zeta-chain (TCR) associated protein kinase 70 kDa (ZAP-70) and spleen tyrosine kinase (SYK) and play a role in signal transduction, bone modeling, brain myelination, and inflammation. Mutations within the gene have been associated with polycystic lipomembranous osteodysplasia with sclerosing leukoencephalopathy (PLOSL), also known as Nasu-Hakola disease. Its putative receptor, triggering receptor expressed on myeloid cells 2 (TREM2), also causes PLOSL. Two alternative transcript variants encoding distinct isoforms have been identified for this gene. Other alternative splice variants have been described, but their full-length nature has not been determined. The polynucleotide sequences of human TYROBP transcriptional variants 1 and 2 are set forth in SEQ ID NO:36-37, respectively, and the corresponding polypeptide sequences are set forth in SEQ ID NO:84-85.

(22) Connective tissue growth factor (CTGF)

Gene aliases: CCN2, HCS24, IGFBP8, MGC102839, NOV2, CTGRP, Fisp12, Hcs24, Fisp-12; hypertrophic chondrocyte-specific protein 24; insulin-like growth factor-binding protein 8, FISP-12 protein; fibroblast inducible secreted protein; fibroblast inducible secreted Protein; hypertrophic chondrocyte-specific gene product 24.

A major connective tissue mitoattractant secreted by vascular endothelial cells. Promotes proliferation and differentiation of chondrocytes. The polynucleotide sequence of human CTGF mRNA is set forth in SEQ ID NO:38 and the corresponding polypeptide sequence is set forth in SEQ ID NO:86.

(23) Secreted Phosphoprotein 1 (SPP1)

Gene aliases: AA960535, AI790405, Apl-1, BNSP, BSPI, Bsp, ETA-1, Eta, OP, Opn, Opnl, Ric, Spp-1, minopontin, OSP; 44 kDa bone phosphoprotein; 44 kDa bone phosphoprotein; bone sialoprotein I; osteopontin, early T-lymphocyte activation 1.

SSP1 is a secreted protein which acts as a cytokine involved in enhancing production of interferon-gamma and interleukin-12 and reducing production of interleukin-10 and which is essential in the pathway that leads to type I immunity. The polynucleotide sequences of human SPP1 transcritional variants 1, 2 and 3 are set forth in SEQ ID NOS:39-41, and the corresponding polypeptide sequences are set forth in SEQ ID NOS:87-89.

U.S. Pat. No. 6,458,590 and US Patent Publications 2004/0142865 and 2006/0252684 relate to inhibition of osteopontin.

(24) Reticulon 4 Receptor (RTN4R)

Gene aliases: NGR, NOGOR, NgR1; Nogo-66 receptor; UNQ330/PRO526; nogo receptor; reticulon 4 receptor precursor.

This gene encodes the receptor for reticulon 4, oligodendrocyte myelin glycoprotein and myelin-associated glycoprotein. This receptor mediates axonal growth inhibition and may play a role in regulating axonal regeneration and plasticity in the adult central nervous system. The polynucleotide sequence of human RTN4R mRNA is set forth in SEQ ID NO:42 and the corresponding polypeptide sequence is set forth in SEQ ID NO:90.

(25) Annexin A2 (ANXA2)

Gene aliases: ANX2, ANX2L4, CAL1H, LIP2, LPC2, LPC2D, P36, PAP-IV; annexin II; calpactin I heavy polypeptide; chromobindin 8; lipocortin II; placental anticoagulant protein IV.

This gene encodes a member of the annexin family. Members of this calcium-dependent phospholipid-binding protein family play a role in the regulation of cellular growth and in signal transduction pathways. This protein functions as an autocrine factor, which heightens osteoclast formation and bone resorption. This gene has three pseudogenes located on chromosomes 4, 9 and 10, respectively. Multiple alternatively spliced transcript variants encoding different isoforms have been found for this gene. The polynucleotide sequences of human ANXA2 transcriptional variants 1, 3 and 2 are set forth in SEQ ID NOS:43-45 and the corresponding polypeptide sequences are set forth in SEQ ID NOS:91-93.

(26) Ras Homolog Gene Family, Member a (RHOA)

Gene Aliases: ARH12, ARHA, RHO12. RHOH12, Aplysia ras-related homolog 12; oncogene RHO H12; small GTP binding protein RhoA.

RHOA is a small GTPase protein known to regulate the actin cytoskeleton in the formation of stress fibers. It acts upon the effector proteins: Rho kinase (ROCK) culminating in the inhibition of axonal regeneration. In vitro studies using the Rho-A antagonist C3 transferase enhances axonal growth on myclin substrates while in vivo studies have not been effective. The polynucleotide sequence of human RHOA mRNA is set forth in SEQ ID NO:46 and the corresponding polypeptide sequence is set forth in SEQ ID NO:94.

(27) Dual oxidase 1 (DUOX1)

Gene Aliases: LNOX1, MGC138840. MGC138841, NOXEF1, THOX1, NADPH thyroid oxidase 1; flavoprotein NADPH oxidase; nicotinamide adenine dinucleotide phosphate oxidase.

The protein encoded by this gene is a glycoprotein and a member of the NADPH oxidase family. The synthesis of thyroid hormone is catalyzed by a protein complex located at the apical membrane of thyroid follicular cells. This complex contains an iodide transporter, thyroperoxidase, and a peroxide generating system that includes this encoded protein and DUOX2. This protein has both a peroxidase homology domain and a gp91phox domain. Two alternatively spliced transcript variants encoding the same protein have been described for this gene. The polynucleotide sequence of human DUOX1 transcriptional variants 1 and 2 are set forth in SEQ ID NOS:47-48 and the corresponding polypeptide sequences are set forth in SEQ ID NOS:95-96.

A "pro-apoptotic polypeptide" refers to a polypeptide encoded by any of the above listed genes, including splice variants, isoforms, orthologs, or paralogs and the like.

An "inhibitor" is a compound which is capable of inhibiting the expression of a gene or the activity of the product of such gene to an extent sufficient to achieve a desired biological or physiological effect. The term "inhibitor" as used herein refers to one or more of an oligonucleotide inhibitor, including siRNA, shRNA, aptamers, antisense molecules, miRNA and ribozymes, as well as antibodies The inhibitor may cause complete or partial inhibition.

The term "inhibit" as used herein refers to reducing the expression of a gene or the activity of the product of such gene to an extent sufficient to achieve a desired biological or physiological effect. Inhibition may be complete or partial.

As used herein, the terms "polynucleotide" and "nucleic acid" may be used interchangeably and refer to nucleotide sequences comprising deoxyribonucleic acid (DNA), and ribonucleic acid (RNA). The terms should also be understood to include, as equivalents, analogs of either RNA or DNA made from nucleotide analogs. Throughout this application, mRNA sequences are set forth as representing the corresponding genes.

"Oligonucleotide" refers to a compound comprising deoxyribonucleotides and/or ribonucleotides from about 2 to about 50 nucleotides. Each DNA or RNA nucleotide may be independently natural or synthetic, and or modified or unmodified. Modifications include changes to the sugar moiety, the base moiety and or the linkages between nucleotides in the oligonucleotide.

The present invention provides methods and compositions for inhibiting expression of a target pro-apoptotic gene in vivo. In general, the method includes administering oligoribonucleotides, in particular small interfering RNAs (i.e., siRNAs) or a nucleic acid material that can produce siRNA in a cell, that target an mRNA transcribed from a pro-apoptotic gene in an amount sufficient to down-regulate expression of a target gene by an RNA interference mechanism. In particular, the subject method can be used to inhibit expression of the pro-apoptotic gene for treatment of a disease.

In accordance with the present invention, the siRNA molecules or inhibitors of the pro-apoptotic gene are used as drugs to treat various pathologies.

siRNA Oligoribonucleotides

Table 8 (B1-B76) comprises nucleic acid sequences of sense and corresponding antisense oligomers, useful in preparing corresponding siRNA compounds. Tables C1, C2 and C3 comprise certain currently preferred nucleic acid sequences of sense and corresponding antisense oligomers, useful in preparing the corresponding siRNA compounds.

The selection and synthesis of siRNA corresponding to known genes has been widely reported; see for example Ui-Tei et al., J Biomed Biotechnol. 2006; 65052; Chalk et al., BBRC. 2004, 319(1):264-74; Sioud and Leirdal, Met. Mol Biol.; 2004, 252:457-69; Levenkova et al., Bioinform. 2004, 20(3):430-2; Ui-Tei et al., NAR 2004, 32(3):936-48. For examples of the use of, and production of, modified siRNA see Braasch et al., Biochem., 2003, 42(26):7967-75; Chiu et al., RNA, 2003, 9(9):1034-48; PCT publications WO 2004/015107 (atugen); WO 02/44321 (Tuschl et al), and U.S. Pat. Nos. 5,898,031 and 6,107,094.

Several groups have described the development of DNA-based vectors capable of generating siRNA within cells. The method generally involves transcription of short hairpin RNAs that are efficiently processed to form siRNAs within cells (Paddison et al. PNAS USA 2002, 99:1443-1448;

Paddison et al. Genes & Dev 2002, 16:948-958; Sui et al. PNAS USA 2002, 8:5515-5520; and Brummelkamp et al. Science 2002, 296:550-553). These reports describe methods of generating siRNAs capable of specifically targeting numerous endogenously and exogenously expressed genes.

The present invention provides double-stranded oligoribonucleotides (e.g., siRNAs), which down-regulate the expression of the pro-apoptotic gene according to the present invention. An siRNA of the invention is, a duplex oligoribonucleotide in which the sense strand is derived from the mRNA sequence of the pro-apoptotic gene, and the antisense strand is complementary to the sense strand. In general, some deviation from the target mRNA sequence is tolerated without compromising the siRNA activity (see e.g. Czauderna et al., 2003, NAR 31(11), 2705-2716). An siRNA of the invention inhibits gene expression on a post-transcriptional level with or without destroying the mRNA. Without being bound by theory, siRNA may target the mRNA for specific cleavage, and degradation and/or may inhibit translation from the targeted message.

As used herein, the term "ribonucleotide" encompasses natural and synthetic, unmodified and modified ribonucleotides. Modifications include changes to the sugar moiety, to the base moiety and/or to the linkages between ribonucleotides in the oligonucleotide.

In some embodiments the oligoribonucleotide according to the present invention comprises modified siRNA. In various embodiments the siRNA comprises an RNA duplex comprising a first strand and a second strand, whereby the first strand comprises a ribonucleotide sequence at least partially complementary to about 18 to about 40 consecutive nucleotides of a target nucleic acid, and the second strand comprises ribonucleotide sequence at least partially complementary to the first strand and wherein said first strand and/or said second strand comprises a plurality of groups of modified ribonucleotides having a modification at the 2'-position of the sugar moiety whereby within each strand each group of modified ribonucleotides is flanked on one or both sides by a group of flanking ribonucleotides whereby each ribonucleotide forming the group of flanking ribonucleotides is selected from an unmodified ribonucleotide or a ribonucleotide having a modification different from the modification of the groups of modified ribonucleotides.

In one embodiment, the group of modified ribonucleotides and/or the group of flanking ribonucleotides comprise a number of ribonucleotides selected from the group consisting of an integer from 1 to 12. Accordingly, the group thus comprises one nucleotide, two nucleotides, three nucleotides, four nucleotides, five nucleotides, six nucleotides, seven nucleotides, eight nucleotides, nine nucleotides, ten nucleotides, eleven nucleotides or twelve nucleotides.

The groups of modified nucleotides and flanking nucleotides may be organized in a pattern on at least one of the strands. In some embodiments the first and second strands comprise a pattern of modified nucleotides. In another embodiment, only one strand comprises a pattern of modified nucleotides. In various embodiments the pattern of modified nucleotides of said first strand is identical relative to the pattern of modified nucleotides of the second strand.

In other embodiments the pattern of modified nucleotides of said first strand is shifted by one or more nucleotides relative to the pattern of modified nucleotides of the second strand.

In some preferred embodiments the middle ribonucleotide in the antisense strand is an unmodified nucleotide. For example, in a 19-oligomer antisense strand, ribonucleotide number 10 is unmodified; in a 21-oligomer antisense strand, ribonucleotide number 11 is unmodified; and in a 23-oligomer antisense strand, ribonucleotide number 12 is unmodified. The modifications or pattern of modification, if any, of the siRNA must be planned to allow for this.

The modifications on the 2' moiety of the sugar residue include amino, fluoro, alkoxy e.g. methoxy, alkyl, amino, fluoro, chloro, bromo, CN, CF, imidazole, caboxylate, thioate, Ct to $C_{10}$ lower alkyl, substituted lower alkyl, alkaryl or aralkyl, $OCF_3$, OCN, O—, S—, or N-alkyl; O—, S, or N-alkenyl; $SOCH_3$; $SO_2CH_3$; $ONO_2$: $NO_2$, $N_3$; heterocycloalkyl; heterozycloalkaryl; aminoalkylamino; polyalkylamino or substituted silyl, as, among others, described in European patents EP 0 586 520 B1 or EP 0 618 925 B1.

In some embodiments the siRNA is blunt ended, at one or both ends. More specifically, the siRNA may be blunt ended on the end defined by the 5'-terminus of the first strand and the 3'-terminus of the second strand, or the end defined by the 3'-terminus of the first strand and the 5'-terminus of the second strand. In other embodiments at least one of the two strands may have an overhang of at least one nucleotide at the 5'-terminus. At least one of the strands may also optionally have an overhang of at least one nucleotide at the 3'-terminus. The overhang may consist of from about 1 to about 5 consecutive nucleotides. A nucleotide of the overhang may be a modified or unmodified ribonucleotide or deoxyribonucleotide.

The length of RNA duplex is from about 18 to about 40 ribonucleotides, preferably 19, 21 or 23 ribonucleotides. Further, the length of each strand may independently have a length selected from the group consisting of about 15 to about 40 bases, preferably 18 to 23 bases and more preferably 19, 21 or 23 ribonucleotides.

Additionally, the complementarity between said first strand and the target nucleic acid may be perfect. In some embodiments, the strands are substantially complementary, i.e. having one, two or up to three mismatches between said first strand and the target nucleic acid. Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

In certain embodiments the first strand and the second strand each comprise at least one group of modified ribonucleotides and at least one group of flanking ribonucleotides. whereby each group of modified ribonucleotides comprises at least one ribonucleotide and whereby each group of flanking ribonucleotides comprises at least one ribonucleotide, wherein each group of modified ribonucleotides of the first strand is aligned with a group of flanking ribonucleotides on the second strand, and wherein the 5' most terminal ribonucleotide is selected from a group of modified ribonucleotides, and the 3' most terminal ribonucleotide of the second strand is a selected from the group of flanking ribonucleotide. In some embodiments each group of modified ribonucleotides consists of a single ribonucleotide and each group of flanking ribonucleotides consists of a single nucleotide.

In yet other embodiments the ribonucleotide forming the group of flanking ribonucleotides on the first strand is an unmodified ribonucleotide arranged in a 3' direction relative to the ribonucleotide forming the group of modified ribonucleotides, and the ribonucleotide forming the group of modified ribonucleotides on the second strand is a modified ribonucleotide which is arranged in 5' direction relative to the ribonucleotide forming the group of flanking ribonucleotides. In some embodiments the first strand of the siRNA comprises five to about twenty, eight to twelve, preferably nine to twelve, groups of modified ribonucleotides, and the second strand comprises seven to eleven, preferably eight to eleven, groups of modified ribonucleotides.

The first strand and the second strand may be linked by a loop structure, which may be comprised of a non-nucleic acid polymer such as, inter alia, polyethylene glycol. Alternatively, the loop structure may be comprised of a nucleic acid, including modified and non-modified ribonucleotides and modified and non-modified deoxyribonucleotides.

Further, the 5'-terminus of the first strand of the siRNA may be linked to the 3'-terminus of the second strand, or the 3'-terminus of the first strand may be linked to the 5'-terminus of the second strand, said linkage being via a nucleic acid linker or a non-nucleic acid linker. In certain embodiments a nucleic acid linker has a length of between about 2-100 nucleic acids, preferably about 2 to about 30 nucleic acids.

In various embodiments, the present invention provides a compound having the structure:
5' $(N)_x$—Z 3' (antisense strand)
3' Z'—$(N')_y$ 5' (sense strand)
wherein each N and N' is a ribonucleotide which may be modified or unmodified in its sugar residue; and each of $(N)_x$ and $(N')_y$ is an oligomer in which each consecutive N or N' is joined to the next N or N' by a covalent bond;
wherein each of x and y is an integer between 18 and 40;
wherein each of Z and Z' may be present or absent, but if present is 1-5 consecutive nucleotides covalently attached at the 3' terminus of the strand in which it is present;
and wherein the sequence of $(N')_y$ comprises a sense sequence having substantial identity to about 18 to about 40 consecutive ribonucleotides in an mRNA set forth is one of SEQ ID NOS:1-48. In preferred embodiments the sense sequence is selected from a sequence presented in any one of Table B (B1-B76; SEQ ID NOS:277 to 50970 and 50993-68654) or Tables C1, C2 and C3 (SEQ ID NOS: 97-276 and 50971-50992).

In some embodiments the compound comprises a phosphodiester bond.

In various embodiments the compound comprises ribonucleotides wherein x=y and wherein x is an integer selected from the group consisting of 18, 19, 20, 21, 22 and 23. In certain embodiments x=y=19 or x=y=23.

In some embodiments the compound is blunt ended, for example wherein Z and Z' are both absent. In an alternative embodiment, the compound comprises at least one 3' overhang, wherein at least one of Z or Z' is present. Z and Z' can be independently comprise one or more covalently linked modified or non-modified nucleotides, as described infra, for example inverted dT or dA; dT, LNA (locked nucleic acids), mirror nucleotide and the like.

In some embodiments each of Z and Z' are independently selected from dT and dTdT.

In some embodiments the compound comprises one or more ribonucleotides unmodified in their sugar residues. In other embodiments the compound comprises at least one ribonucleotide modified in the sugar residue. In some embodiments the compound comprises a modification at the 2' position of the sugar residue. Modifications in the 2' position of the sugar residue include amino, fluoro, alkoxy and alkyl moieties. In certain preferred embodiments the alkoxy modification is a methoxy moiety at the 2' position of the sugar residue (2'-O-methyl: 2'-O-Me; 2'-O—$CH_3$), In some embodiments the compound comprises modified alternating ribonucleotides in one or both of the antisense and the sense strands. In certain embodiments the compound comprises modified alternating ribonucleotides in the antisense and the sense strands. In some preferred embodiments the middle ribonucleotide of the antisense strand is not modified; e.g. ribonucleotide in position 10 in a 19-mer strand.

In various embodiments the compound comprises an antisense sequence present in Table B SEQ ID NOS:277 to 50970 and 50993-68654). In other embodiments the present invention provides a mammalian expression vector comprising an antisense sequence present in Table B (SEQ ID NOS:277 to 50970 and 50993-68654). Certain presently preferred compounds are listed in Tables C1, C2 and C3, and their sequences are set forth in SEQ ID NOS: 97-276 and SEQ ID NOS 50971-50992.

In certain embodiments the present invention provides a compound having the structure
5' (N)x 3' antisense strand
3' (N')y 5' sense strand
wherein each of x and y=19 and $(N)_x$ and $(N')_y$ are fully complementary;
wherein alternating ribonucleotides in (N)x and (N')y are modified to result in a 2'-O-methyl modification in the sugar residue of the ribonucleotides;
wherein each N at the 5' and 3' termini of $(N)_x$ are modified;
wherein each N' at the 5' and 3' termini of $(N')_y$ are unmodified:
wherein each of $(N)_x$ and $(N')_y$ is selected from the group of oligomers set forth in Table B (B1-B25 and 876; SEQ ID NOS:277-15114 and 68647-68654).

Certain presently preferred compounds are listed in Tables C1 and C3, and their sequences are set forth in SEQ ID NOS: 97-266 and SEQ ID NOS 50971-50992.

$(N)_x$ and $(N')_y$ may be phosphorylated or non-phosphorylated at the 3' and 5' termini.

In certain embodiments of the invention, alternating ribonucleotides are modified in the 2' position of the sugar residue in both the antisense and the sense strands of the compound. In particular the exemplified siRNA has been modified such that a 2'-O-methyl (Me) group was present on the first, third, fifth, seventh, ninth, eleventh, thirteenth, fifteenth, seventeenth and nineteenth nucleotide of the antisense strand, whereby the very same modification, i.e. a 2'-O-Me group, was present at the second, fourth, sixth, eighth, tenth, twelfth, fourteenth, sixteenth and eighteenth nucleotide of the sense strand. Additionally, it is to be noted that these particular siRNA compounds are also blunt ended.

In certain embodiments the present invention provides a compound having the structure
5' (N)x 3' antisense strand
3' (N')y 5' sense strand
wherein each of x and y=23 and $(N)_x$ and $(N')_y$ are fully complementary
wherein alternating ribonucleotides in $(N)_x$ and $(N')_y$ are modified to result in a 2'-O-methyl modification in the sugar residue of the ribonucleotides;
wherein each N at the 5' and 3' termini of $(N)_x$ are modified;
wherein each N' at the 5' and 3' termini of $(N')_y$ are unmodified;
wherein each of $(N)_x$ and $(N')_y$ is selected from the group of oligomers set forth in Table B (B51-B75; SEQ ID NOS: 30939-68646).

$(N)_x$ and $(N')_y$ may be phosphorylated or non-phosphorylated at the 3' and 5' termini. In certain embodiments of the invention, alternating ribonucleotides are modified in both the antisense and the sense strands of the compound. In particular the exemplified siRNA has been modified such that a 2'-O-methyl (2'-OMe) group was present on the first, third, fifth, seventh, ninth, eleventh, thirteenth, fifteenth, seventeenth, nineteenth, twenty-first and twenty-third nucleotide of the antisense strand $(N)_x$, and whereby the very same modification, i.e. a 2'-OMe group, was present at the second, fourth, sixth, eighth, tenth, twelfth, fourteenth, sixteenth, eighteenth, twentieth and twenty-second nucleotide of the sense strand $(N')_y$. Additionally, it is to be noted that these particular siRNA compounds are also blunt ended.

In certain embodiments of the compounds of the invention having alternating ribonucleotides modified in one or both of the antisense and the sense strands of the compound; for 19-mers and 23-mers the ribonucleotides at the 5' and 3' termini of the antisense strand are modified in their sugar residues, and the ribonucleotides at the 5' and 3' termini of the sense strand are unmodified in their sugar residues. For 21-mers the ribonucleotides at the 5' and 3' termini of the sense strand are modified in their sugar residues, and the ribonucleotides at the 5' and 3' termini of the antisense strand are unmodified in their sugar residues. As mentioned above, it is preferred that the middle nucleotide of the antisense strand is unmodified.

Additionally, the invention provides siRNA comprising a nucleic acid sequence set forth in Table B (B1-B76; SEQ ID NOS:277-50970 and 50993-68654) wherein 1, 2, or 3 of the nucleotides in one strand or both strands are substituted thereby providing at least one base pair mismatch. The substituted nucleotides in each strand are preferably in the terminal region of one strand or both strands.

In currently preferred embodiments the ribonucleic acid sequences of the siRNA are SEQ ID NOS:97-276 and SEQ ID NOS: 50971-50992 of Tables C1, C2 and C3. In certain currently preferred embodiments the ribonucleic acid sequences of the siRNA are set forth in SEQ ID NOS:99-100; SEQ ID NOS:133-134; SEQ ID NOS:137-138; SEQ ID NOS:211-212; SEQ ID NOS:213-214 as shown in Table C1.

According to one preferred embodiment of the invention, the antisense and the sense strands of the siRNA are phosphorylated only at the 3'-terminus and not at the 5'-terminus. According to another preferred embodiment of the invention, the antisense and the sense strands are non-phosphorylated. According to yet another preferred embodiment of the invention, the 5' most ribonucleotide in the sense strand is modified to abolish any possibility of in vivo 5'-phosphorylation.

The invention further provides a vector capable of expressing any of the aforementioned oligoribonucleotides in unmodified form in a cell after which appropriate modification may be made. In preferred embodiment the cell is a mammalian cell, preferably a human cell.

Pharmaceutical Compositions

While it may be possible for the compounds of the present invention to be administered as the raw chemical, it is preferable to present them as a pharmaceutical composition. Accordingly the present invention provides a pharmaceutical composition comprising one or more of the compounds of the invention; and a pharmaceutically acceptable carrier. This composition may comprise a mixture of two or more different siRNAs. In one embodiment, this composition may comprise a mixture of siRNA to RhoA and siRNA to one or more of the other pro-apoptotic genes of the invention. In a more particular embodiment, this composition may comprise a mixture of siRNA to RhoA and siRNA to Casp2. Without being bound by theory. RhoA is a small GTPase that when activated inhibits neurite outgrowth. Its inhibition is relevant for spinal cord injury and it can be combined for this indication with anti-apoptotic siRNAs of the invention. The latter will protect, and siRNA to RhoA will promote regeneration, and so a combined or even synergistic effect is produced.

The invention further provides a pharmaceutical composition comprising at least one compound of the invention covalently or non-covalently bound to one or more compounds of the invention in an amount effective to inhibit the pro-apoptotic genes of the present invention; and a pharmaceutically acceptable carrier. The compound may be processed intracellularly by endogenous cellular complexes to produce one or more oligoribonucleotides of the invention.

The invention further provides a pharmaceutical composition comprising a pharmaceutically acceptable carrier and one or more of the compounds of the invention in an amount effective to inhibit expression in a cell of a human pro-apoptotic gene of the present invention, the compound comprising a sequence which is substantially complementary to the sequence of $(N)_x$.

Substantially complementary refers to complementarity of greater than about 84%, to another sequence. For example in a duplex region consisting of 19 base pairs one mismatch results in 94.7% complementarity, two mismatches results in about 89.5% complementarity and 3 mismatches results in about 84.2% complementarity, rendering the duplex region substantially complementary. Accordingly substantially identical refers to identity of greater than about 84%, to another sequence.

Additionally, the invention provides a method of inhibiting the expression of the pro-apoptotic genes of the present invention by at least 20%, preferably 30%, even more preferably 40% or even 50% as compared to a control comprising contacting an mRNA transcript of the pro-apoptotic gene of the present invention with one or more of the compounds of the invention.

In one embodiment the oligoribonucleotide is inhibiting one or more of the pro-apoptotic genes of the present invention, whereby the inhibition is selected from the group comprising inhibition of gene function, inhibition of polypeptide and inhibition of mRNA expression.

In one embodiment the compound is inhibiting a pro-apoptotic polypeptide, whereby the inhibition is selected from the group comprising inhibition of function (which may be examined by an enzymatic assay or a binding assay with a known interactor of the native gene/polypeptide, inter alia), inhibition of protein (which may be examined by Western blotting, ELISA or immuno-precipitation, inter alia) and inhibition of mRNA expression (which may be examined by Northern blotting. quantitative RT-PCR, in-situ hybridisation or microarray hybridisation, inter alia).

In additional embodiments the invention provides a method of treating a subject suffering from a disease accompanied by an elevated level of the pro-apoptotic genes of the present invention, the method comprising administering to the subject a compound of the invention in a therapeutically effective dose thereby treating the subject.

More particularly, the invention provides an oligoribonucleotide wherein one strand comprises consecutive nucleotides having, from 5' to 3', the sequence set forth in any one of SEQ ID NOS:277-50970 and 50993-68654, shown also in Table B, or a homolog thereof wherein in up to two of the ribonucleotides in each terminal region is altered.

Additionally, further nucleic acids according to the present invention comprise at least 14 contiguous nucleotides of any one of the polynucleotides in Table B (SEQ TD NOS:

277-50970 and 50993-68654) and more preferably 14 contiguous nucleotide base pairs at any end of the double-stranded structure comprised of the first strand and second strand as described above.

It will be understood by one skilled in the art that given the potential length of the nucleic acid according to the present invention and particularly of the individual strands forming such nucleic acid according to the present invention, some shifts relative to the coding sequence of the pro-apoptotic genes of the present invention to each side is possible, whereby such shifts can be up to 1, 2, 3, 4, 5 and 6 nucleotides in both directions, and whereby the thus generated double-stranded nucleic acid molecules shall also be within the present invention.

Delivery

The siRNA molecules of the present invention may be delivered to the target tissue by direct application of the naked molecules prepared with a carrier or a diluent.

The term "naked siRNA" refers to siRNA molecules that are free from any delivery vehicle that acts to assist, promote or facilitate entry into the cell, including viral sequences, viral particles, liposome formulations, lipofectin or precipitating agents and the like. For example, siRNA in PBS is "naked siRNA".

However, in some embodiments the siRNA molecules of the invention are delivered in liposome formulations and lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al., FEBS Let. 2003, 539:111-114; Xia et al., Nat. Biotech. 2002, 20:1006-1010; Reich et al., Mol. Vision 2003, 9: 210-216; Sorensen et al., J. Mol. Biol. 2003, 327: 761-766; Lewis et al, Nat. Gen. 2002, 32: 107-108 and Simeoni et al., NAR 2003, 31, 11: 2717-2724). siRNA has recently been successfully used for inhibition of gene expression in primates (see for example, Tolentino et al., Retina 24(4):660).

The pharmaceutically acceptable carriers, solvents, diluents, excipients, adjuvants and vehicles as well as implant carriers generally refer to inert, non-toxic solid or liquid fillers, diluents or encapsulating material not reacting with the active ingredients of the invention and they include liposomes and microspheres. Examples of delivery systems useful in the present invention include U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art. In one specific embodiment of this invention topical and transdermal formulations may be selected. The siRNAs or pharmaceutical compositions of the present invention are administered and dosed in accordance with good medical practice, taking into account the clinical condition of the individual subject, the disease to be treated, the site and method of administration, scheduling of administration, patient age, sex, body weight and other factors known to medical practitioners.

The "therapeutically effective dose" for purposes herein is thus determined by such considerations as are known in the art. The dose must be effective to achieve improvement including but not limited to improved survival rate or more rapid recovery, or improvement or elimination of symptoms and other indicators as are selected as appropriate measures by those skilled in the art.

In general, the active dose of compound for humans is in the range of from 1 ng/kg to about 20-100 mg/kg body weight per day, preferably about 0.01 mg to about 2-10 mg/kg body weight per day, in a regimen of one dose per day or twice or three or more times per day for a period of 1-4 weeks or longer. The compounds of the present invention can be administered by any of the conventional routes of administration. It should be noted that the compound can be administered as the compound or as pharmaceutically acceptable salt and can be administered alone or as an active ingredient in combination with pharmaceutically acceptable carriers, solvents, diluents, excipients, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. Liquid forms may be prepared for injection, the term including subcutaneous, transdermal, intravenous, intramuscular, intrathecal, and other parental routes of administration. The liquid compositions include aqueous solutions, with and without organic co-solvents, aqueous or oil suspensions, emulsions with edible oils, as well as similar pharmaceutical vehicles. In a particular embodiment, the administration comprises intravenous administration. In another embodiment the administration comprises topical or local administration. In addition, in certain embodiments the compositions for use in the novel treatments of the present invention may be formed as aerosols, for example for intranasal administration. In certain embodiments, oral compositions (such as tablets, suspensions, solutions) may be effective for local delivery to the oral cavity such as oral composition suitable for mouthwash for the treatment of oral mucositis.

Methods of Treatment

In another aspect, the present invention relates to a method for the treatment of a subject in need of treatment for a disease or disorder associated with the abnormal expression of the proapoptotic genes of Table A, comprising administering to the subject an amount of an inhibitor which reduces or inhibits expression of these genes.

In, preferred embodiments the subject being treated is a warm-blooded animal and, in particular, mammals including human.

The methods of the invention comprise administering to the subject one or more inhibitory compounds which down-regulate expression of the proapoptotic genes of Table A; and in particular siRNA in a therapeutically effective dose so as to thereby treat the subject.

In various embodiments the inhibitor is selected from the group consisting of siRNA. shRNA, an aptamer, an antisense molecule, miRNA, a ribozyme, and an antibody. In the presently preferred embodiments the inhibitor is siRNA.

The term "treatment" refers to both therapeutic treatment and prophylactic or preventative measures, wherein the object is to prevent or slow down (lessen) pro-apoptotic-related disorder as listed above. Those in need of treatment include those already experiencing the disease or condition, those prone to having the disease or condition, and those in which the disease or condition is to be prevented. The compounds of the invention may be administered before, during or subsequent to the onset of the disease or condition or symptoms associated therewith. In cases where treatment is for the purpose of prevention, then the present invention relates to a method for delaying the onset of or averting the development of the disease or disorder.

The present invention relates to the use of compounds which down-regulate the expression of the pro-apoptotic genes of the invention particularly to novel small interfering RNAs (siRNAs), in the treatment of the following diseases or conditions in which inhibition of the expression of the pro-apoptotic genes is beneficial: hearing loss, acute renal failure (ARF), glaucoma, acute respiratory distress syndrome (ARDS) and other acute lung and respiratory injuries, ischemia-reperfusion injury following lung transplantation, organ transplantation including lung, liver, heart, bone marrow, pancreas, cornea and kidney transplantation, spinal cord injury, pressure sores, age-related macular degeneration (AMD), dry eye syndrome, oral mucositis and chronic obstructive pulmonary disease (COPD). Other indications include chemical-induced nephrotoxicity and chemical-induced neurotoxicity, for example toxicity induced by cisplatin and cisplatin-like compounds, by aminoglycosides, by loop diuretics, and by hydroquinone and their analogs.

Methods, molecules and compositions which inhibit the pro-apoptotic genes of the invention are discussed herein at length, and any of said molecules and/or compositions may be beneficially employed in the treatment of a subject suffering from any of said conditions. Preferred oligomer sequences useful in the preparation of siRNA directed to selected pro-apoptotic genes are set forth in SEQ ID NOS: 277-50970 and 50993.68654, listed in Table B.

The method of the invention includes administering a therapeutically effective amount of one or more compounds which down-regulate expression of the pro-apoptotic genes. particularly the novel siRNAs of the present invention, small molecule inhibitors of the pro-apoptotic genes as described herein or antibodies to the pro-apoptotic proteins.

In some preferred embodiments, the methods of the invention are applied to various conditions of hearing loss. Without being bound by theory, the hearing loss may be due to apoptotic inner ear hair cell damage or loss, wherein the damage or loss is caused by infection, mechanical injury, loud sound, aging (presbycusis), or chemical-induced ototoxicity. Ototoxins include therapeutic drugs including antineoplastic agents, salicylates. quinines, and aminoglycoside antibiotics, contaminants in foods or medicinals, and environmental or industrial pollutants. Typically, treatment is performed to prevent or reduce ototoxicity, especially resulting from or expected to result from administration of therapeutic drugs. Preferably a therapeutically effective composition is given immediately after the exposure to prevent or reduce the ototoxic effect. More preferably, treatment is provided prophylactically, either by administration of the composition prior to or concomitantly with the ototoxic pharmaceutical or the exposure to the ototoxin.

By "ototoxin" in the context of the present invention is meant a substance that through its chemical action injures, impairs or inhibits the activity of the sound receptors component of the nervous system related to hearing, which in turn impairs hearing (and/or balance). In the context of the present invention, ototoxicity includes a deleterious effect on the inner ear hair cells. Ototoxic agents that cause hearing impairments include, but are not limited to, antineoplastic agents such as vincristine, vinblastine, cisplatin and cisplatin-like compounds, taxol and taxol-like compounds, dideoxy-compounds, e.g., dideoxyinosine; alcohol; metals; industrial toxins involved in occupational or environmental exposure; contaminants of food or medicinals; and overdoses of vitamins or therapeutic drugs, e.g., antibiotics such as penicillin or chloramphenicol, and megadoses of vitamins A, D, or B6, salicylates, quinines, loop diuretics, and phosphodiesterase type 5 (PDE5) inhibitors such as sildenafil citrate (Viagra®).

By "exposure to an ototoxic agent" is meant that the ototoxic agent is made available to, or comes into contact with, a mammal. Exposure to an ototoxic agent can occur by direct administration, e.g., by ingestion or administration of a food, medicinal, or therapeutic agent, e.g., a chemotherapeutic agent, by accidental contamination, or by environmental exposure. e.g., aerial or aqueous exposure.

Hearing may be due to end-organ lesions involving inner ear hair cells, e.g., acoustic trauma, viral endolymphatic labyrinthitis. Meniere's disease. Hearing impairments include tinnitus, which is a perception of sound in the absence of an acoustic stimulus, and may be intermittent or continuous, wherein there is diagnosed a sensorineural loss. Hearing loss may be due to bacterial or viral infection, such as in herpes zoster oticus, purulent labyrinthitis arising from acute otitis media, purulent meningitis, chronic otitis media, sudden deafness including that of viral origin, e.g., viral endolymphatic labyrinthitis caused by viruses including mumps, measles, influenza, chicken pox, mononucleosis and adenovinises. The hearing loss can be congenital, such as that caused by rubella, anoxia during birth, bleeding into the inner ear due to trauma during delivery, ototoxic drugs administered to the mother, erythroblastosis fetalis, and hereditary conditions including Waardenburg's syndrome and Hurler's syndrome.

The hearing loss can be noise-induced, generally due to a noise greater than 85 decibels (db) that damages the inner ear. In a particular aspect of the invention, the hearing loss is caused by an ototoxic drug that effects the auditory portion of the inner ear, particularly inner ear hair cells. Incorporated herein by reference are chapters 196, 197, 198 and 199 of The Merck Manual of Diagnosis and Therapy, 14th Edition. (1982). Merck Sharp & Dome Research Laboratories, N.J. and corresponding chapters in the most recent 16th edition, including Chapters 207 and 210) relating to description and diagnosis of hearing and balance impairments.

It is the object of the present invention to provide a method and compositions for treating a mammal, to prevent, reduce, or treat a hearing impairment, disorder or imbalance, preferably an ototoxin-induced hearing condition, by administering to a mammal in need of such treatment a composition of the invention. One embodiment of the invention is a method for treating a hearing disorder or impairment wherein the ototoxicity results from administration of a therapeutically effective amount of an ototoxic pharmaceutical drug. Typical ototoxic drugs are chemotherapeutic agents, e.g. antineoplastic agents, and antibiotics. Other possible candidates include loop-diuretics, quinines or a quinine-like compound, and salicylate or salicylate-like compounds.

The methods and compositions of the present invention are especially effective when the ototoxic compound is an antibiotic, preferably an aminoglycoside antibiotic. Ototoxic aminoglycoside antibiotics include but are not limited to neomycin, paromomycin, ribostamycin, lividomycin, kanamycin, amikacin, tobramycin, viomycin, gentamicin, sisomicin, netilmicin, streptomycin, dibekacin, fortimicin, and dihydrostreptomycin, or combinations thereof. Particular antibiotics include neomycin B, kanamycin A, kanamycin B, gentamicin C1, gentamicin C1a, and gentamicin C2.

The methods and compositions of the present invention are also effective when the ototoxic compound is a antineoplastic agent such as vincristine, vinblastine, cisplatin and cisplatin-like compounds and taxol and taxol-like compounds.

The methods and compositions of the present invention are also effective in the treatment of acoustic trauma or mechanical trauma, preferably acoustic or mechanical trauma that leads to inner ear hair cell loss. Acoustic trauma to be treated in the present invention may be caused by a single exposure to an extremely loud sound, or following long-term exposure to everyday loud sounds above 85 decibels. Mechanical inner ear trauma to be treated in the present invention is for example the inner ear trauma following an operation of electronic device insertion in the inner ear. The compositions of the present invention prevent or minimize the damage to inner ear hair cells associated with the operation.

In some embodiments the composition of the invention is co-administered with an ototoxin. For example, an improved method is provided for treatment of infection of a mammal by administration of an aminoglycoside antibiotic, the improvement comprising administering a therapeutically effective amount of one or more compounds (particularly novel siRNAs) which down-regulate expression of the pro-apoptotic genes, to the subject in need of such treatment to reduce or prevent ototoxin-induced hearing impairment associated with the antibiotic. The compounds which down-regulate expression of the pro-apoptotic genes particularly novel siRNAs are preferably administered locally within the inner ear.

In yet another embodiment an improved method for treatment of cancer in a mammal by administration of a chemotherapeutic compound is provided, wherein the improvement comprises administering a therapeutically effective amount of a composition of the invention to the subject in need of such treatment to reduce or prevent ototoxin-induced hearing impairment associated with the chemotherapeutic drug. The compounds which reduce or prevent the ototoxin-induced hearing impairment, e.g. the novel siRNAs inter alia are preferably administered locally within the inner ear.

In another embodiment the methods of treatment are applied to treatment of hearing loss resulting from the administration of a chemotherapeutic agent in order to treat its ototoxic side-effect. Ototoxic chemotherapeutic agents amenable to the methods of the invention include, but are not limited to an antineoplastic agent, including cisplatin or cisplatin-like compounds, taxol or taxol-like compounds, and other chemotherapeutic agents believed to cause ototoxin-induced hearing impairments, e.g., vincristine, an antineoplastic drug used to treat hematological malignancies and sarcomas. Cisplatin-like compounds include carboplatin (Paraplatin®), tetraplatin, oxaliplatin, aroplatin and transplatin inter alia.

In another embodiment the methods of the invention are applied to hearing impairments resulting from the administration of quinine and its synthetic substitutes, typically used in the treatment of malaria, to treat its ototoxic side-effect.

In another embodiment the methods of the invention are applied to hearing impairments resulting from administration of a diuretic to treat its ototoxic side-effect. Diuretics, particularly "loop" diuretics, i.e. those that act primarily in the Loop of Henle, are candidate ototoxins. Illustrative examples, not limiting to the invention method, include furosemide, ethacrylic acid, and mercurials. Diuretics are typically used to prevent or eliminate edema. Diuretics are also used in nonedematous states for example hypertension, hypercalcemia, idiopathic hypercalciuria, and nephrogenic diabetes insipidus.

In another preferred embodiment, the compounds of the invention are used for treating acute renal failure, in particular acute renal failure due to ischemia in post surgical patients, and acute renal failure due to chemotherapy treatment such as cisplatin administration or sepsis-associated acute renal failure. A preferred use of the compounds of the invention is for the prevention of acute renal failure in high-risk patients undergoing major cardiac surgery or vascular surgery. The patients at high-risk of developing acute renal failure can be identified using various scoring methods such as the Cleveland Clinic algorithm or that developed by US Academic Hospitals (QMMI) and by Veterans' Administration (CICSS). Other preferred uses of the compounds of the invention are for the prevention of ischemic acute renal failure in kidney transplant patients or for the prevention of toxic acute renal failure in patients receiving chemotherapy.

In another preferred embodiment, the compounds of the invention are used for treating glaucoma. Main types of glaucoma are primary open angle glaucoma (POAG), angle closure glaucoma, normal tension glaucoma and pediatric glaucoma. These are marked by an increase of intraocular pressure (IOP), or pressure inside the eye. When optic nerve damage has occurred despite a normal IOP, this is called normal tension glaucoma. Secondary glaucoma refers to any case in which another disease causes or contributes to increased eye pressure, resulting in optic nerve damage and vision loss.

In another preferred embodiment, the compounds of the invention are used for treating or preventing the damage caused by nephrotoxins such as diuretics, β-blockers, vasodilator agents. ACE inhibitors, cyclosporin, aminoglycoside antibiotics (e.g. gentamicin), amphotericin B, cisplatin, radiocontrast media, immunoglobulins, mannitol, NSAIDs (e.g. aspirin, ibuprofen, diclofenac), cyclophosphamide, methotrexate, aciclovir, polyethylene glycol, β-lactam antibiotics, vancomycin, rifampicin, sulphonamides, ciprofloxacin, ranitidine, cimetidine, furosemide, thiazides, phenytoin, penicillamine, lithium salts, fluoride, demeclocycline, foscarnet, aristolochic acid.

In another preferred embodiment, the compounds of the invention are used for treating or preventing the damage caused by spinal-cord injury especially spinal cord trauma caused by motor vehicle accidents, falls, sports injuries, industrial accidents. gunshot wounds, spinal cord trauma caused by spine weakening (such as from rheumatoid arthritis or osteoporosis) or if the spinal canal protecting the spinal cord has become too narrow (spinal stenosis) due to the normal aging process, direct damage that occur when the spinal cord is pulled, pressed sideways, or compressed, damage to the spinal-cord following bleeding, fluid accumulation. and swelling inside the spinal cord or outside the spinal cord (but within the spinal canal). The compounds of the invention are also used for treating or preventing the damage caused by spinal-cord injury due to disease such as polio or spina bifida.

In other embodiments the compounds and methods of the invention are useful for treating or preventing the incidence or severity of acute lung injury, in particular conditions which result from ischemic/reperfusion injury or oxidative stress. For example, acute respiratory distress syndrome (ARDS) due to coronavirus infection or endotoxins, severe acute respiratory syndrome (SARS), ischemia reperfusion injury associated with lung transplantation and other acute lung injuries.

In other embodiments the compounds and methods of the invention are useful for treating or preventing damage following organ transplantation including lung, liver, heart, bone pancreas, intestine, skin, blood vessels, heart valve, bone and kidney transplantation.

The term "organ transplant" is meant to encompass transplant of any one or more of the following organs including, inter alia, lung, kidney, heart, skin, vein, bone, cartilage, liver transplantation. Although a xenotransplant can be contemplated in certain situations, an allotransplant is usually preferable. An autograft can be considered for bone marrow, skin, bone, cartilage and or blood vessel transplantation.

The siRNA compounds of the present invention are particularly useful in treating a subject experiencing the adverse effects of organ transplant, including ameliorating, treating or preventing perfusion injury.

For organ transplantation, either the donor or the recipient or both may be treated with a compound or composition of the present invention. Accordingly, the present invention relates to a method of treating an organ donor or an organ recipient comprising the step of administering to the organ donor or organ recipient a therapeutically effective amount of a compound according to the present invention.

The invention further relates to a method for preserving an organ comprising contacting the organ with an effective amount of compound of the present invention. Also provided is a method for reducing or preventing injury (in particular reperfusion injury) of an organ during surgery and/or following removal of the organ from a subject comprising placing the organ in an organ preserving solution wherein the solution comprises a compound according to the present invention.

In other embodiments the compounds and methods of the invention are useful for treating or preventing the incidence or severity of other diseases and conditions in a patient. These diseases and conditions include stroke and stroke-like situations (e.g. cerebral, renal, cardiac failure), neuronal cell death, brain injuries with or without reperfusion issues, chronic degenerative diseases e.g. neurodegenerative disease including Alzheimer's disease, Huntington's disease, Parkinson's disease, multiple sclerosis, amyotrophic lateral sclerosis, spinobulbar atrophy, prion disease, and apoptosis resulting from traumatic brain injury (TBI).

The compounds and methods of the invention are directed to providing neuroprotection, or to provide cerebroprotection, or to prevent and/or treat cytotoxic T cell and natural killer cell-mediated apoptosis associated with autoimmune disease and transplant rejection, to prevent cell death of cardiac cells including heart failure, cardiomyopathy, viral infection or bacterial infection of heart, myocardial ischemia, myocardial infarct, and myocardial ischemia, coronary artery by-pass graft, to prevent and/or treat mitochondrial drug toxicity e.g. as a result of chemotherapy or HIV therapy, to prevent cell death during viral infection or bacterial infection, or to prevent and/or treat inflammation or inflammatory diseases, inflammatory bowel disease, sepsis and septic shock, or to prevent cell death from follicle to ovocyte stages, from ovocyte to mature egg stages and sperm (for example, methods of freezing and transplanting ovarian tissue, artificial fertilization), or to preserve fertility in mammals after chemotherapy, in particular human mammals, or to prevent and/or treat. macular degeneration, or to prevent and/or treat acute hepatitis, chronic active hepatitis, hepatitis-B, and hepatitis-C, or to prevent hair loss, (e.g. hair loss due-to male-pattern baldness, or hair loss due to radiation, chemotherapy or emotional stress), or to treat or ameliorate skin damage whereby the skin damage may be due to exposure to high levels of radiation, heat, chemicals, sun, or to burns and autoimmune diseases), or to prevent cell death of bone marrow cells in myelodysplastic syndromes (MDS), to treat pancreatitis, to treat rheumatoid arthritis, psoriasis, glomerulonephritis, atherosclerosis, and graft versus host disease (GVHD), or to treat retinal pericyte apoptosis, retinal damages resulting from ischemia, diabetic retinopathy, or to treat any disease states associated with an increase of apoptotic cell death.

The methods comprising administering to the subject a composition comprising one or more inhibitors (such as siRNA) which inhibit at least one gene of the present invention in a therapeutically effective dose, thereby treating the subject, in one preferred embodiment, siRNA compounds directed to two pro-apoptotic genes are combined in order to obtain a synergistic therapeutic effect. In one specific example, siRNA compounds directed to RhoA (whose mRNA sequence is set forth as SEQ ID NO:46) are combined with siRNA compounds directed to any other pro-apoptotic gene of Table A, preferably with siRNA compounds directed to Casp2 (whose mRNA sequence is set forth as SEQ ID NOS:10-1).

The present invention also provides for a process of preparing a pharmaceutical composition, which comprises:
  providing one or more double stranded compound of the invention; and
  admixing said compound with a pharmaceutically acceptable carrier.

The present invention also provides for a process of preparing a pharmaceutical composition, which comprises admixing one or more compounds of the present invention with a pharmaceutically acceptable carrier.

In a preferred embodiment, the compound used in the preparation of a pharmaceutical composition is admixed with a carrier in a pharmaceutically effective dose. In a particular embodiment the compound of the present invention is conjugated to a steroid or to a lipid or to another suitable molecule e.g. to cholesterol.

Modifications

Modifications or analogs of nucleotides can be introduced to improve the therapeutic properties of the nucleotides, Improved properties include increased nuclease resistance and/or increased ability to permeate cell membranes.

Accordingly, the present invention also includes all analogs of, or modifications to, a oligonucleotide of the invention that does not substantially affect the function of the polynucleotide or oligonucleotide. In a preferred embodiment such modification is related to the base moiety of the nucleotide, to the sugar moiety of the nucleotide and/or to the phosphate moiety of the nucleotide.

In one embodiment the modification is a modification of the phosphate moiety, whereby the modified phosphate moiety is selected from the group comprising phosphothioate.

The compounds of the present invention can be synthesized by any of the methods that are well-known in the art for synthesis of ribonucleic (or deoxyribonucleic) oligonucleotides. Such synthesis is, among others, described in Beaucage and Iyer, Tetrahedron 1992; 48:2223-2311; Beaucage and Iyer, Tetrahedron 1993; 49: 6123-6194 and Caruthers, et. al., Methods Enzymol. 1987; 154: 287-313; the synthesis of thioates is, among others, described in Eckstein, Annu. Rev. Biochem. 1985; 54: 367-402, the synthesis of RNA molecules is described in Sproat, in Humana Press 2005 edited by Herdewijn P.; Kap. 2: 17-31 and respective downstream processes are, among others, described in Pingoud et, al., in IRL Press 1989 edited by Oliver R. W. A.; Kap. 7: 183-208.

Other synthetic procedures are known in the art e.g., the procedures as described in Usman et al., 1987. J. Am. Chem. Soc., 109, 7845; Scaringe et al., 1990. NAR., 18, 5433; Wincott et al., 1995, NAR. 23, 2677-2684; and Wincott et al., 1997. Methods Mol. Bio., 74, 59, and these procedures may make use of common nucleic acid protecting and coupling groups, such as dimethoxytrityl at the 5'-end, and phosphoramidites at the 3'-end. The modified (e.g. 2'-O-methylated) nucleotides and unmodified nucleotides are incorporated as desired.

The oligonucleotides of the present invention can be synthesized separately and joined together post-synthetically, for example, by ligation (Moore et al., 1992. Science 256, 9923; Draper et al., International Patent Publication No. WO 93/23569; Shabarova et a., 1991, NAR 19, 4247; Bellon et al., 1997, Nucleosides & Nucleotides, 16, 951; Bellon et al., 1997, Bioconjugate Chem. 8, 204), or by hybridization following synthesis and/or deprotection.

It is noted that a commercially available machine (available, inter alia, from Applied Biosystems) can be used; the oligonucleotides are prepared according to the sequences disclosed herein, Overlapping pairs of chemically synthesized fragments can be ligated using methods well known in the art (e.g., see U.S. Pat. No. 6,121,426). The strands are synthesized separately and then are annealed to each other in the tube. Then, the double-stranded siRNAs are separated from the single-stranded oligonucleotides that were not annealed (e.g. because of the excess of one of them) by HPLC. In relation to the siRNAs or siRNA fragments of the present invention, two or more such sequences can be synthesized and linked together for use in the present invention.

The compounds of the invention can also be synthesized via tandem synthesis methodology. as described for example in US Patent Publication No. US 2004/0019001 (McSwiggen), wherein both siRNA strands are synthesized as a single contiguous oligonucleotide fragment or strand separated by a cleavable linker which is subsequently cleaved to provide separate siRNA fragments or strands that hybridize and permit purification of the siRNA duplex. The linker can be a polynucleotide linker or a non-nucleotide linker.

The present invention further provides for a pharmaceutical composition comprising two or more siRNA molecules for the treatment of any of the diseases and conditions mentioned herein, whereby said two molecules may be physically mixed together in the pharmaceutical composition in amounts which generate equal or otherwise beneficial activity, or may be covalently or non-covalently bound, or joined together by a nucleic acid linker of a length ranging from 2-100, preferably 2-50 or 2-30 nucleotides. In one embodiment, the siRNA molecules are comprised of a double-stranded nucleic acid structure as described herein. wherein the two siRNA sequences are selected from the nucleic acids set forth in Table B.

Thus, the siRNA molecules may be covalently or non-covalently bound or joined by a linker to form a tandem siRNA compound. Such tandem siRNA compounds comprising two siRNA sequences are typically of 38-150 nucleotides in length, more preferably 38 or 40-60 nucleotides in length, and longer accordingly if more than two siRNA sequences are included in the tandem molecule. A longer tandem compound comprised of two or more longer sequences which encode siRNA produced via internal cellular processing, e.g., long dsRNAs, is also envisaged, as is a tandem molecule encoding two or more shRNAs. Such tandem molecules are also considered to be a part of the present invention. A tandem compound comprising two or more siRNAs sequences of the invention is envisaged. In a particular embodiment, the tandem comprises RhoA siRNA covalently linked to one or more of the other siRNAs of the invention. In a more particular embodiment, the tandem compound may comprise a sequence comprising siRNA to RhoA and a sequence comprising siRNA to Casp2. Without being bound by theory RhoA is a small GTPase that when activated inhibits neurite outgrowth and its inhibition is relevant for spinal cord injury. Thus a tandem compound for this indication can comprise RhoA siRNA sequence and one or more siRNA sequences to anti-apoptotic siRNAs of the invention. The latter will protect, and siRNA to RhoA will promote regeneration, and so a combined or even synergistic effect is produced.

siRNA molecules that target the pro-apoptotic genes of the invention may be the main active component in a pharmaceutical composition, or may be one active component of a pharmaceutical composition containing two or more siRNAs (or molecules which encode or endogenously produce two or more siRNAs, be it a mixture of molecules or one or more tandem molecules which encode two or more siRNAs), said pharmaceutical composition further being comprised of one or more additional siRNA molecule which targets one or more additional gene. Simultaneous inhibition of said additional. gene(s) will likely have an additive or synergistic effect for treatment of the diseases disclosed herein.

Additionally, the pro-apoptotic siRNA disclosed herein or any nucleic acid molecule comprising or encoding such siRNA can be linked or bound (covalently or non-covalently) to antibodies (including aptamer molecules) against cell surface internalizable molecules expressed on the target cells, in order to achieve enhanced targeting for treatment of the diseases disclosed herein. For example, anti-Fas antibody (preferably a neutralizing antibody) may be combined (covalently or non-covalently) with any pro-apoptotic siRNA. In another example, an aptamer which can act like a ligand/antibody may be combined (covalently or non-covalently) with any pro-apoptotic siRNA.

The compounds of the present invention can be delivered either directly or with viral or non-viral vectors. When delivered directly the sequences are generally rendered nuclease resistant. Alternatively the sequences can be incorporated into expression cassettes or constructs such that the sequence is expressed in the cell as discussed herein below. Generally the construct contains the proper regulatory sequence or promoter to allow the sequence to be expressed in the targeted cell. Vectors optionally used for delivery of the compounds of the present invention are commercially available, and may be modified for the purpose of delivery of the compounds of the present invention by methods known to one of skill in the art.

It is also envisaged that a long oligonucleotide (typically 25-500 nucleotides in length) comprising one or more stem and loop structures, where stem regions comprise the sequences of the oligonucleotides of the invention, may be delivered in a carrier, preferably a pharmaceutically acceptable carrier, and may be processed intracellularly by endogenous cellular complexes (e.g. by DROSHA and DICER as described above) to produce one or more smaller double stranded oligonucleotides (siRNAs) which are oligonucleotides of the invention. This oligonucleotide can be termed a tandem shRNA construct. It is envisaged that this long oligonucleotide is a single stranded oligonucleotide comprising one or more stem and loop structures, wherein each stem region comprises a sense and corresponding antisense siRNA sequence of the pro-apoptotic genes of the invention. In particular, it is envisaged that this oligonucleotide comprises sense and antisense siRNA sequences as depicted in Table B, set forth in SEQ ID NOS:277-50970 and 50993-68654.

All analogues of, or modifications to, a nucleotide/oligonucleotide may be employed with the present invention, provided that said analogue or modification does not substantially affect the function of the nucleotide/oligonucleotide. The nucleotides can be selected from naturally occurring or synthetic modified bases. Naturally occurring bases include adenine, guanine, cytosine, thymine and uracil, Modified bases of nucleotides include inosine, xanthine, hypoxanthine, 2-aminoadenine, 6-methyl, 2-propyl and other alkyl adenines, 5-halo uracil, 5-halo cytosine, 6-aza cytosine and 6-aza thymine, psuedo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thioalkyl guanines. 8-hydroxyl guanine and other substituted guanines, other aza and deaza adenines, other aza and deaza guanines, 5-trifluoromethyl uracil and 5-trifluoro cytosine. In some embodiments one or more nucleotides in an oligomer is substituted with inosine.

In addition, analogues of polynucleotides can be prepared wherein the structure of one or more nucleotide is fundamentally altered and better suited as therapeutic or experimental reagents. An example of a nucleotide analogue is a peptide nucleic acid (PNA) wherein the deoxyribose (or ribose) phosphate backbone in DNA (or RNA is replaced with a polyamide backbone which is similar to that found in peptides. PNA analogues have been shown to be resistant to enzymatic degradation and to have extended stability in vivo and in vitro. Other modifications that can be made to oligonucleotides include polymer backbones, cyclic backbones, acyclic backbones, thiophosphate-D-ribose backbones, triester backbones. thioate backbones, 2'-5' bridged backbone, artificial nucleic acids, morpholino nucleic acids, locked nucleic acid (LNA), glycol nucleic acid (GNA), threose nucleic acid (TNA), arabinoside, and mirror nucleoside (for example, beta-L-deoxynucleoside instead of beta-D-deoxynucleoside). Examples of siRNA compounds comprising LNA nucleotides are disclosed in Elmen et al., (NAR 2005, 33(1):439-447).

The compounds of the present invention can be synthesized using one or more inverted nucleotides, for example inverted thymidine or inverted adenine (see, for example, Takei, et al., 2002, JBC 277(26):23800-06).

A "mirror" nucleotide is a nucleotide with reversed chirality to the naturally occurring or commonly employed nucleotide, i.e., a mirror image (L-nucleotide) of the naturally occurring (D-nucleotide). The nucleotide can be a ribonucleotide or a deoxyribonucleotide and my further comprise at least one sugar, base and or backbone modification. U.S. Pat. No. 6,602,858 discloses nucleic acid catalysts comprising at least one L-nucleotide substitution.

Although the inhibitors of the present invention are preferably siRNA molecules, other inhibitors contemplated to be used in the methods of the invention to inhibit a pro-apoptotic gene and to treat the diseases and conditions described herein are inter alia antibodies, preferably neutralizing antibodies or fragments thereof, including single chain antibodies, antisense oligonucleotides, antisense DNA or RNA molecules, ribozymes, proteins, polypeptides and peptides including peptidomimetics and dominant negatives, and also expression vectors expressing all the above.

Additional inhibitors may be small chemical molecules, which generally have a molecular weight of less than 2000 daltons, more preferably less than 1000 daltons, even more preferably less than 500 daltons. These inhibitors may act as follows: small molecules may affect expression and/or activity; antibodies may affect activity; all kinds of antisense may affect the pro-apoptotic gene expression: and dominant negative polypeptides and peptidomimetics may affect activity: expression vectors may be used inter alia for delivery of antisense or dominant-negative polypeptides or antibodies.

Antibodies

The term "antibody" refers to IgG, IgM, IgD, IgA, and IgE antibody, inter alia. The definition includes polyclonal antibodies or monoclonal antibodies. This term refers to whole antibodies or fragments of antibodies comprising an antigen-binding domain, e.g. antibodies without the Fc portion, single chain antibodies, miniantibodies, fragments consisting of essentially only the variable, antigen-binding domain of the antibody, etc. The term "antibody" may also refer to antibodies against polynucleotide sequences obtained by cDNA vaccination. The term also encompasses antibody fragments which retain the ability to selectively bind with their antigen or receptor and are exemplified as follows, inter alia:

(1) Fab, the fragment which contains a monovalent antigen-binding fragment of an antibody molecule which can be produced by digestion of whole antibody with the enzyme papain to yield a light chain and a portion of the heavy chain;

(2) $(Fab')_2$, the fragment of the antibody that can be obtained by treating whole antibody with the enzyme pepsin without subsequent reduction; $F(ab'_2)$ is a dimer of two Fab fragments held together by two disulfide bonds;

(3) Fv, defined as a genetically engineered fragment containing the variable region of the light chain and the variable region of the heavy chain expressed as two chains; and (4) Single chain antibody (SCA), defined as a genetically engineered molecule containing the variable region of the light chain and the variable region of the heavy chain linked by a suitable polypeptide linker as a genetically fused single chain molecule.

The genes of the present invention that are preferably inhibited using specific antibodies for the treatment of a desired disease are reticulon 4 receptor (RTN4R) and annexin A2 (ANXA2).

Antisense Molecules

By the term "antisense" (AS) or "antisense fragment" is meant a polynucleotide fragment (comprising either deoxyribonucleotides, ribonucleotides or a mixture of both) having inhibitory antisense activity, said activity causing a decrease in the expression of the endogenous genomic copy of the corresponding gene. An AS polynucleotide is a polynucleotide which comprises consecutive nucleotides having a sequence of sufficient length and homology to a sequence present within the sequence of the target gene to permit hybridization of the AS to the gene. Many reviews have covered the main aspects of antisense (AS) technology and its enormous therapeutic potential (Aboul-Fadl. Curr Med Chem. 2005.12(19):2193-214; Crooke, Curt Mol Med. 2004, 4(5):465-87; Crooke, Annu Rev Med. 2004; 55:61-95; Vacek et al., Cell Mol Life Sci. 2003, 60(5):825-33; Cho-Chung, Arch Pharm Res. 2003, 26(3):183-91. There are further reviews on the chemical (Crooke, 1995; Uhlmann et al. 1990). cellular (Wagner, 1994. Nature. 24; 372(6504):

333-5) and therapeutic (Hanania, et al, 1995; Scanlon, et al., 1995; Gewirtz, 1993) aspects of this technology. Antisense intervention in the expression of specific genes can be achieved by the use of synthetic AS oligonucleotide sequences (see for example, Zhang et al., Curr Cancer Drug Targets. 2005 5(1):43-9.)

AS oligonucleotide sequences may be short sequences of DNA, typically 15-30 mer but may be as small as 7 mer (Wagner et al, 1996 Nat Biotechnol, 14(7):840-4), designed to complement a target mRNA of interest and form an RNA:AS duplex. This duplex formation can prevent processing, splicing, transport or translation of the relevant mRNA. Moreover, certain AS nucleotide sequences can elicit cellular RNase H activity when hybridized with their target mRNA, resulting in mRNA degradation (Calabretta et al, 1996 Semin Oncol. 23(1):78-87). In that case, RNase H will cleave the RNA component of the duplex and can potentially release the AS to further hybridize with additional molecules of the target RNA. An additional mode of action results from the interaction of AS with genomic DNA to form a triple helix which can be transcriptionally inactive.

The sequence target segment for the antisense oligonucleotide is selected such that the sequence exhibits suitable energy related characteristics important for oligonucleotide duplex formation with their complementary templates, and shows a low potential for self-dimerization or self-complementation (Anazodo et al., 1996 BBRC. 229(1):305-9). For example, the computer program OLIGO (Primer Analysis Software, Version 3.4). can be used to determine antisense sequence melting temperature, free energy properties, and to estimate potential self-dimer formation and self-complimentary properties. The program allows the determination of a qualitative estimation of these two parameters (potential self-dimer formation and self-complimentary) and provides an indication of "no potential" or "some potential" or "essentially complete potential". Using this program target segments are generally selected that have estimates of no potential in these parameters. However, segments can be used that have "some potential" in one of the categories. A balance of the parameters is used in the selection as is known in the art. Further, the oligonucleotides are also selected as needed so that analogue substitution do not substantially affect function.

Phosphorothioate antisense oligonucleotides do not normally show significant toxicity at concentrations that are effective and exhibit sufficient pharmacodynamic half-lives in animals (Agarwal et al., 1996) and are nuclease resistant. Antisense induced loss-of-function phenotypes related with cellular development were shown for a variety of different genes including integrin (Galileo et al., Neuron. 1992 9(6): 1117.31.) and for the N-myc protein (Rosolen et a., 1990 Prog Clin Biol Res. 366:29-36). Antisense oligonucleotide inhibition of basic fibroblast growth factor (bFGF). having mitogenic and angiogenic properties. suppressed 80% of growth in glioma cells (Morrison, IBC 1991 266(2):728-34) in a saturable and specific manner. Being hydrophobic, antisense oligonucleotides interact well with phospholipid membranes (Akhter et al., NAR., 1991, 19:5551-5559). Following their interaction with the cellular plasma membrane, they are actively (or passively) transported into living cells (Loke et al., PNAS 1989, 86(10):3474-8), in a saturable mechanism predicted to involve specific receptors (Yakubov et al., PNAS, 1989 86(17):6454-58).

Ribozymes

A "ribozyme" is an RNA molecule that possesses RNA catalytic ability (see Cech Biochem Soc Trans. 2002 November; 30(Pt 6):1162-6. for review) and cleaves a specific site in a target RNA. In accordance with the present invention, ribozymes which cleave mRNA may be utilized as inhibitors. This may be necessary in cases where antisense therapy is limited by stoichiometric considerations (Sarver et al., 1990, Gene Regulation and Aids, pp. 305-325). Ribozymes can then be used that will target the a gene associated with a bone marrow disease. The number of RNA molecules that are cleaved by a ribozyme is greater than the number predicted by stochiochemistry (Hampel and Tritz, Biochem. 1989, 28(12):4929-33; Uhlenbeck, Nature. 1987 328(6131):596-600).

Ribozymes catalyze the phosphodiester bond cleavage of RNA, Several ribozyme structural families have been identified including Group I introns, RNase P, the hepatitis delta virus ribozyme, hammerhead ribozymes and the hairpin ribozyme originally derived from the negative strand of the tobacco ringspot virus satellite RNA (sTRSV) (Sullivan, 1994; U.S. Pat. No. 5,225,347). The latter two families are derived from viroids and virusoids, in which the ribozyme is believed to separate monomers from oligomers created during rolling circle replication (Symons, 1989 and 1992). Hammerhead and hairpin ribozyme motifs are most commonly adapted for trans-cleavage of mRNAs for gene therapy (Sullivan, 1994). In general the ribozyme has a length of from about 30-100 nucleotides. Delivery of ribozymes is similar to that of AS fragments and/or siRNA molecules.

Screening of Inactivation Compounds for Pro-Apoptotic Genes:

Some of the compounds and compositions of the present invention may be used in a screening assay for identifying and isolating compounds that modulate the activity of a pro-apoptotic gene, in particular compounds that modulate a disorder accompanied by an elevated level of the pro-apoptotic genes of the invention. The compounds to be screened comprise inter alia substances such as small chemical molecules and antisense oligonucleotides.

The inhibitory activity of the compounds of the present invention on pro-apoptotic genes or binding of the compounds of the present invention to pro-apoptotic genes may be used to determine the interaction of an additional compound with the pro-apoptotic polypeptide, e.g., if the additional compound competes with the oligonucleotides of the present invention for inhibition of a pro-apoptotic gene, or if the additional compound rescues said inhibition. The inhibition or activation can be tested by various means, such as, inter alia, assaying for the product of the activity of the pro-apoptotic polypeptide or displacement of binding compound from the pro-apoptotic polypeptide in radioactive or fluorescent competition assays.

The present invention is illustrated in detail below with reference to examples, but is not to be construed as being limited thereto.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

EXAMPLES

General Methods in Molecular Biology

Standard molecular biology techniques known in the art and not specifically described were generally followed as in Sambrook et al., Molecular Cloning: A Laboratory Manual, Cold Spring Harbor Laboratory Press, New York (1989), and as in Ausubel et al., Current Protocols in Molecular Biology, John Wiley and Sons, Baltimore, Md. (1989) and as in Perbal. A Practical Guide to Molecular Cloning, John Wiley & Sons, New York (1988), and as in Watson et al., Recombinant DNA. Scientific American Books. New York and in Birren et al (eds) Genome Analysis: A Laboratory Manual Series. Vols. 1-4 Cold Spring Harbor Laboratory Press, New York (1998) and methodology as set forth in U.S. Pat. No. 4,666,828; 4,683,202; 4,801,531; 5,192,659 and 5,272,057 and incorporated herein by reference. Polymerase chain reaction (PCR) was carried out generally as in PCR Protocols: A Guide To Methods And Applications, Academic Press, San Diego. Calif. (1990). In situ (In cell) PCR in combination with Flow Cytometry can be used for detection of cells containing specific DNA and mRNA sequences (Testoni et al., 1996. Blood 87:3822.) Methods of performing RT-PCR are also well known in the art.

Example 1

In Vitro Testing of the siRNA Compounds for Pro-Apoptotic Genes

1. General

About 1.5-2×10⁵ test cells (HeLa cells or 293T cells for siRNA targeting the human gene and NRK52 cells or NMUMG cells for siRNA targeting the rat/mouse gene) were seeded per well in 6 wells plate (70-80% confluent).

After 24 h cells were transfected with siRNA oligomers using Lipofectamine™ 2000 reagent (Invitrogene) at final concentration of 500 pM, 5 nM, 20 nM or 40 nM. The cells were incubated at 37° C. in a C02 incubator for 726.

As positive control for cells transfection PTEN-Cy3 labeled siRNA oligos were used. As negative control for siRNA activity GFP siRNA oligos were used.

About 72 h after transfection cells were harvested and RNA was extracted from cells. Transfection efficiency was tested by fluorescent microscopy.

The siRNAs used in the in vitro experiments described in Example 1 were 19-mers or 23-mers, having alternating ribonucleotides modified in both the antisense and the sense strands of the compound. For 19-mers, the modification was such that a 2'-O-methyl (Me) group was present on the first, third, fifth, seventh, ninth, eleventh, thirteenth, fifteenth, seventeenth and nineteenth nucleotide of the antisense strand, whereby the very same modification, i.e. a 2'-O-Me group, was present at the second, fourth, sixth, eighth, tenth, twelfth, fourteenth, sixteenth and eighteenth nucleotide of the sense strand. These particular siRNA compounds were also blunt ended and were non-phosphorylated at the termini; however, comparative experiments have shown that siRNAs phosphorylated at the 3'-termini have similar activity.

Results:

The percent of inhibition of gene expression using specific siRNAs was determined using qPCR analysis of target gene in cells expressing the endogenous gene. The data in Tables C1, C2 and C3 below demonstrate the percent of residual expression of the target gene in cells following treatment with specific siRNA molecules (Tables C1 and C3: 19-mer siRNA compounds: Table C2; 23-mer siRNA compounds). In general, the siRNAs having specific sequences that were selected for in vitro testing were specific for both human and the rat/rabbit genes. Similar results of reduced expression of specific genes are obtained with other siRNAs, the sequences of which are listed in Table B.

TABLE C1

Percent of knockdown of the expression of the target human gene in cells using 19-mer siRNA molecules.

| Target gene | Cell line* | siRNA tested | Sequence | % of control** |
|---|---|---|---|---|
| TP53BP2 | 293T | TP53BP2_1 SEQ ID NOS: 97-98 | Sense: GAGGGUGAAAUUCAACCC Antisense: GGGUUGAAUUUCACCCUC | 118, 75 |
| TP53BP2 | 293T | TP53BP2_2 SEQ ID NOS: 99-100 | Sense: CACCCAGAGAACAUUUAUU Antisense: AAUAAAUGUUCUCUGGGUG | 44, 26 |
| TP53BP2 | 293T | TP53BP2_3 SEQ ID NOS: 101-102 | Sense: GGGUGAAAUUCAACCCCCU Antisense: AGGGGGUUGAAUUUCACCC | 134, 87 |
| TP53BP2 | 293T | TP53BP2_4 SEQ ID No. 103-104 | Sense: AGGGUGAAAUUCAACCCCC Antisense: GGGGGUUGAAUUUCACCCU | 123, 115 |
| TP53BP2 | 293T | TP53BP2_5 SEQ ID NOS: 105-106 | Sense: AGGGAGUGUUUGAAUAAGC Antisense: GCUUAUUCAAACACUCCCU | 89, 30 |
| TP53BP2 | 293T | TP53BP2_6 SEQ IDNOS: 107-108 | Sense; ACCCAGAGAACAUUUAUUC Antisense: GAAUAAAUGUUCUCUGGGU | 93 |

TABLE C1-continued

Percent of knockdown of the expression of the target human gene in cells using 19-mer siRNA molecules.

| Target gene | Cell line* | siRNA tested | Sequence | % of control** |
|---|---|---|---|---|
| TP53BP2 | 293T | TP53BP2_8 SEQ ID NOS: 109-110 | Sense: CGCUGAGGGAGAAAGAGAA Antisense: UUCUCUUUCUCCCUCAGCG | 67 |
| LRDD | PC-3 | LRDD_1 SEQ ID NOS: 111-112 | Sense: CGCACCUGAAGAAUGUGAA Antisense: UUCACAUUCUUCAGGUGCG | 25 |
| LRDD | PC-3 | LRDD_2 SEQ ID NOS: 113-114 | Sense: GUCUUCUACACGCACCUGA Antisense: UCAGGUGCGAGUAGAAGAC | 38 |
| LRDD | PC-3 | LRDD_3 SEQ IS Nos. 115-116 | Sense: GACUGUUCCUGACCUCAGA Antisense: UCUGAGGUCAGGAACAGUC | 12, 38, 18 |
| LRDD | PC-3 | LRDD_5 SEQ ID NOS: 117-118 | Sense: ACCUCAGAUUUGGACAGCU Antisnse: AGCUGUCCAAAUCUGAGGU | 34, 47, 21 |
| CYBA | MDA-MB-4 | CYBA_15 SEQ ID NOS: 119-120 | Sense: UGGGGACAGAAGUACAUGA Antisense: UCAUGUACUUCUGUCCCCA | 5, 3 |
| CYBA | MDA-MB-4 | CYBA_16 SEQ ID NOS: 121-122 | Sense: GGGCCCUUUACCAGGAAUU Antisense: AAUUCCUGGUAAAGGGCCC | 28, 20 |
| CYBA | MDA-MB-4 | CYBA_17 SEQ ID NOS: 123-124 | Sense: CCCUUUACCAGGAAUUACU Antisense: AGUAAUUCCUGGUAAAGGG | 5, 2 |
| ATF3 | 293T | ATF3_2 SEQ ID NOS: 125-126 | Sense: GAAGGAACAUUGCAGAGCU Antisense: AGCUCUGCAAUGUUCCUUC | 107, 72 |
| ATF3 | 293T | ATF3_3 SEQ ID NOS: 127-128 | Sense: ACAGAUAAAAGAAGGAACA Antisense: UGUUCCUUCUUUUAUCUGU | 109, 80 |
| ATF3 | 293T | ATF3_4 SEQ ID NOS: 129-130 | Sense: AUCCUAGUAUUCCUAACCU Antisense: AGGUUAGGAAUACUAGGAU | 79, 60 |
| ATF3 | 293T | ATF3_5 SEQ ID NOS: 131-132 | Sense: AUCCCAGUAUUCCUAGCCU Antisense: AGGCUAGGAAUACUGGGAU | 93, 90 |
| CASP2 | HeLa- | CASP2_1 SEQ ID NOS: 133-134 | Sense: GCACUCCUCAAUUUUAUCA Antisense: UGAUAAAAUUCAGGAGUGC | 12, 8 |
| CASP2 | HeLa- | CASP2_2 SEQ ID NOS: 135-136 | Sense: CGAGAGGAAAUGCAAGAGA Antisense: UCUCUUGCAUUUCCUGUGC | 25, 38 |

TABLE C1-continued

Percent of knockdown of the expression of the target human gene in cells using 19-mer siRNA molecules.

| Target gene | Cell line* | siRNA tested | Sequence | % of control** |
|---|---|---|---|---|
| CASP2 | HeLa- | CASP2_3 SEQ ID NOS: 137-138 | Sense: GGGCUUGUGAUAUGCACGU Antisense: ACGUGCAUAUCACAAGCCC | 22, 39 |
| CASP2 | HeLa- | CASP2_4 SEQ ID NOS: 139-140 | Sense: GCCAGAAUGUGGAACUCCU Antisense: AGGAGUUCCACAUUCUGGC | 11, 18 |
| NOX3 | 293 | NOX_4 SEQ ID NOS: 141-142 | Sense: UCCUGGAACUUCACAUGAA Antisense: UUCAUGUGAAGUUCCAGGA | 21, 32 |
| NOX3 | 293 | NOX_5 SEQ ID NOS: 143-144 | Sense: GGUGUUCAUUUCUAUUACA Antisense: UGUAAUAGAAAUGAACACC | 28 |
| NOX3 | 293 | NOX_6 SEQ ID NOS: 145-146 | Sense: ACACACACCAUGUUUUCAU Antisense: AUGAAAACAUGGUGUGUGU | 41 |
| NOX3 | 293 | NOX_7 SEQ ID NOS: 147-148 | Sense: GGUACACACACCAUGUUUU Antisense: AAAACAUGGUGUGUGUACC | 26, 36 |
| NOX3 | 293 | NOX_8 SEQ ID NOS: 149-150 | Sense: CACUUUCUGAGUUAUCAUA Antisense: UAUGAUAACUCAGAAAGUG | 31 |
| NOX3 | 293 | NOX_9 SEQ ID NOS: 151-152 | Sense: CUGAAAUCUAUAUGGUACA Antisense: UGUACCAUAUAGAUUUCAG | 34 |
| NOX3 | 293 | NOX_10 SEQ ID NOS: 153-154 | Sense: CUGGCGAUUUCAACAAGAA Antisense: UUCUUGUUGAAAUCGCCAG | 49 |
| NOX3 | 293 | NOX_11 SEQ ID NOS: 155-156 | Sense: UCUGGCGAUUUCAACAAGA Antisense: UGUUGUUGAAAUCGCCAGA | 39 |
| HRK | MDA-MB-468 | HRK_1 SEQ ID NOS: 157-158 | Sense: CCCCAAUGCUAUUUACAUA Antisense: UAUGUAAAUAGCAUUGGGG | 15, 20 |
| HRK | MDA-MB-468 | HRK_2 SEQ ID NOS: 159-160 | Sense: AUGCUAUUUACAUACAGCU Antisense: AGCUGUAUGUAAAUAGCAU | 22, 68 |
| C1QBP | HeLa- | C1QBP_1 SEQ ID NOS: 161-158 | Sense: CCCCAAUGCUAUUUACAUA Antisense: UAUGUAAAUAGCAUUGGGG | 60 |
| C1QBP | HeLa- | C1QBP_2 SEQ ID NOS: 163-164 | Sense: AUGCUAUUUACAUACAGCU Antisense: AGCUGUAUGUAAAUAGCAU | 70 |
| C1QBP | HeLa- | C1QBP_3 SEQ ID NOS: 165-166 | Sense: GAGCCUGAACUGACAUCAA Antisense: UUGAUGUCAGUUCAGGCUC | 6, 4 |

TABLE C1-continued

Percent of knockdown of the expression of the target
human gene in cells using 19-mer siRNA molecules.

| Target gene | Cell line* | siRNA tested | Sequence | % of control** |
|---|---|---|---|---|
| BNIP3 | 293T | BNIP3_1 SEQ ID NOS: 167-168 | Sense: GAGACAUGGAAAAAAUACU Antisense: AGUAUUUUUUCCAUGUCUC | 58 |
| BNIP3 | 293T | BNIP3_2 SEQ ID NOS: 169-170 | Sense: GACAUGGAAAAAAUACUGC Antisense: GCAGUAUUUUUUCCAUGUC | 96, 73 |
| BNIP3 | 293T | BNIP3_3 SEQ ID NOS: 171-172 | Sense: ACCCUCAGCAUGAGGAACA Antisense: UGUUCCUCAUGCUGAGGGU | 116 |
| BNIP3 | 293T | BNIP3_4 SEQ ID NOS: 173-174 | Sense: GAAAAACUCAGAUUGGAUA Antisense: UAUCCAAUCUGAGUUUUUC | 89, 90 |
| BNIP3 | 293T | BNIP3_11 SEQ ID NOS: | Sense: CUGCAUUGGUGAAUUUAAU Antisense: AUUAAAUUCACCAAUGCAG | 69 |
| BNIP3 | 293T | BNIP3_12 SEQ ID NOS: | Sense: CAGGUUGUCUACUAAAGAA Antisense: UUCUUUAGUAGACAACCUG | 56 |
| BNIP3 | 293T | BNIP3_13 SEQ ID NOS: | Sense: GCCUUAUAUAUCACACUAU Antisense: AUAGUGUGAUAUAUAAGGC | 76 |
| BNIP3 | 293T | BNIP3_15 SEQ ID NOS: | Sense: GGAAUUAAGUCUCCGAUUA Antisense: UAAUCGGAGACUUAAUUCC | 56 |
| BNIP3 | 293T | BNIP3_22 SEQ ID NOS: | Sense: AGGUUGUCUACUAAAGAAA Antisense: UUUCUUUAGUAGACAACCU | 78 |
| BNIP3 | 293T | BNIP3_23 SEQ ID NOS: | Sense: GAGAAAAACAGCUCACAGU Antisense ACUGUGAGCUGUUUUUCUC | 92 |
| BNIP3 | 293T | BNIP3_24 SEQ ID NOS: | Sense: CCAAGAUAGAGCUACAAAC Antisense GUUUGUAGCUCUAUCUUGG | 59 |
| BNIP3 | 293T | BNIP3_25 SEQ ID NOS: 189-190 | Sense: CACUCUGCAUUGGUGAAUU Antisense AAUUCACCAAUGCAGAGUG | 67 |
| BNIP3 | 293T | BNIP3_26 SEQ ID NOS: 191-192 | Sense: CCUUAAUUCAGCUGAAGUA Antisense UACUUCAGCUGAAUUAAGG | 80 |
| BNIP3 | 293T | BNIP3_27 SEQ ID NOS: 193-194 | Sense: GUUCAACUUUUGUGUGCUU Antisense AAGCACACAAAAGUUGAAC | 82 |
| BNIP3 | 293T | BNIP3_28 SEQ ID NOS: 195-196 | Sense: UCCUUUGUGUUCAACUUUU Antisense AAAAGUUGAACACAAAGGA | 42 |

TABLE C1-continued

Percent of knockdown of the expression of the target human gene in cells using 19-mer siRNA molecules.

| Target gene | Cell line* | siRNA tested | Sequence | % of control** |
|---|---|---|---|---|
| MAPK8 | 293T | MAPK8_1 SEQ ID NOS: 197-198 | Sense: ACCACAGAAAUCCCUAGAA Antisense: UUCUAGGGAUUUCUGUGGU | 40, 51 |
| MAPK8 | 293T | MAPK8_2 SEQ ID NOS: 199-200 | Sense: GCCGACCAUUUCAGAAUCA Antisense: UGAUUCUGAAAUGGUCGGC | 60 |
| MAPK8 | 293T | MAPK8_3 SEQ ID NOS: 201-202 | Sense: GGACUUACGUUCAAAACAG Antisense: CUGUUUUCAACGUAAGUCC | 70 |
| MAPK8 | 293T | MAPK8_4 SEQ ID NOS: 203-204 | Sense: UGGAUGCAAAUCUUUGCCA Antisense: UGGCAAAGAUUUGCAUCCA | 100 |
| MAPK14 | A431 | MAPK14_1 SEQ ID NOS: 205-206 | Sense: ACCACAGAAAUCCCUAGAA Antisense: AUGAUGGACUGAAAUGGUC | + in Western blot |
| MAPK14 | A431 | MAPK14_2 SEQ ID NOS: 207-208 | Sense: GAGGUCUAAAGUAUAUACA Antisense: UGUAUAUACUUUAGACCUC | ++ in Western blot |
| MAPK14 | A431 | MAPK14_3 SEQ ID NOS: 209-210 | Sense: GUGCUGCUUUUGACACAAA Antisense: UUUGUGUCAAAAGCAGCAC | − in Western blot |
| RAC1 | 293T | RAC1_1 SEQ ID NOS: 211-212 | Sense: UUGGUGCUGUAAAAUACCU Antisense: AGGUAUUUUACAGCACCAA | 27, 21, 41 |
| RAC1 | 293T | RAC1_2 SEQ ID NOS: 213-214 | Sense: GAGUCCUGCAUCAUUUGAA Antisense: UUCAAAUGAUGCAGGACUC | 32, 17, 27 |
| RAC1 | 293T | RAC1_3 SEQ ID NOS: 215-216 | Sense: GAUGUGUUCUUAAUUUGCU Antisense: AGCAAAUUAAGAACACAUC | 23, 19, 29 |
| BMP2 | Hela | BMP2_5 SEQ ID NOS: 217-218 | Sense: GUCAAGCCAAACACAAACA Antisense: UGUUUGUGUUUGGCUUGAC | 58 (in 10 nM) 15 (in 10 nM) |
| SPP1 | HEPG2 | SPP1_1 SEQ ID NOS: 219-220 | Sense: GUCCAGCAAUUAAUAAAAC Antisense: GUUUUAUUAAUUGCUGGAC | 87 |
| SPP1 | HEPG2 | SPP1_2 SEQ ID NOS: 221-222 | Sense: GUGCCAUACCAGUUAAACA Antisense: UGUUUAACUGGUAUGGCAC | 19, 28 |
| SPP1 | HEPG2 | SPP1_3 SEQ ID NOS: 223-224 | Sense: GCAAAAUGAAAGAGAACAU Antisense: AUGUUCUCUUUCAUUUUGC | 51, 39 |
| SPP1 | HEPG2 | SPP1_5 SEQ ID NOS: 225-226 | Sense: GCAUUUCUCAUGAAUUAGA Antisense: UCUAAUUCAUGAGAAAUGC | 26 |

TABLE C1-continued

Percent of knockdown of the expression of the target human gene in cells using 19-mer siRNA molecules.

| Target gene | Cell line* | siRNA tested | Sequence | % of control** |
|---|---|---|---|---|
| SPP1 | HEPG2 | SPP1_6 SEQ ID NOS: 227-228 | Sense: CCGCAUUUCUCAUGAAUUA Antisense: UAAUUCAUGAGAAAUGCGG | 26 |
| RHOA | 293T-human | RHOA_1 SEQ ID NOS: 229-230 | Sense: GUACCAGUUAAUUUUUCCA Antisense: UGGAAAAAUUAACUGGUAC | 47, 20 |
| RHOA | 293T-human | RHOA_2 SEQ ID NOS: 231-232 | Sense: UAGAAAACAUCCCAGAAAA Antisense: UUUUCUGGGAUGUUUUCUA | 34, 14 |
| RHOA | 293T-human | RHOA_3 SEQ ID NOS: 233-234 | Sense: ACCAGUUAAUUUUUCCAAC Antisense: GUUGGAAAAAUUAACUGGU | 49, 26 |
| RHOA | 293T-human | RHOA_ SEQ ID NOS: 235-236 | Sense: GCCACUUAAUGUAUGUUAC Antisense: GUAACAUACAUUAAGUGGC | 29, 20 |
| RHOA | 293T-human | RHOA_5 SEQ ID NOS: 237-238 | Sense: GGGCAGUUUUUUGAAAAUG Antisense: CAUUUUCAAAAAACAGCCC | 78 |
| RHOA | 293T-human | RHOA_6 SEQ ID NOS: 239-240 | Sense: GGCUAAGUAAAUAGGAAUU Antisense: AAUUCCUAUUUACUUAGCC | 34 |
| RHOA | 293T-human | RHOA_7 SEQ ID NOS: 241-242 | Sense: CCUGUGGAAAGACAUGCUU Antisense: AAGCAUGUCUUUCCACAGG | 25 |
| RHOA | 293T-human | RHOA_8 SEQ ID NOS: 243-244 | Sense: GUGCUCUUUUCUCCUCACU Antisense: AGUGAGGAGAAAAGAGCAC | 35 |
| RHOA | 293T-human | RHOA_9 SEQ ID NOS: 245-246 | Sense: GGGCUAAGUAAAUAGGAAU Antisense: AUUCCUAUUUACUUAGCCC | 23 |
| RHOA | 293T-human | RHOA_10 SEQ ID NOS: 247-248 | Sense: GUGGGCAGUUUUUUGAAAA Antisense: UUUUCAAAAAACUGCCCAC | 61 |
| RHOA | 293T-human | RHOA_11 SEQ ID NOS: 249-250 | Sense: GGUGCCUUGUCUUGUGAAA Antisense: UUUCACAAGACAAGGCACC | 33 |
| RHOA | 293T-human | RHOA_12 SEQ ID NOS: 251-252 | Sense: CCCAAGUUCAUGCAGCUGU Antisense: ACAGCUGCAUGAAGUUGGG | 79 |
| RHOA | 293T-human | RHOA_13 SEQ ID NOS: 253-254 | Sense: GGCACUCAGUCUCUCUUCU Antisense: AGAAGAGAGACUGAGUGCC | 36 |
| RHOA | 293T-human | RHOA_14 SEQ ID NOS: 255-256 | Sense: CACUUUGGAAGAUGGCAUA Antisense: UAUGCCAUCUUCCAAAGUG | 41 |

TABLE C1-continued

Percent of knockdown of the expression of the target human gene in cells using 19-mer siRNA molecules.

| Target gene | Cell line* | siRNA tested | Sequence | % of control** |
|---|---|---|---|---|
| Duox1 | exogenous expression | Duox1_1 SEQ ID NOS: 257-258 | Sense: GAGAGAAGUUCCAACGCAG Antisense: CUGCGUUGGAACUUCUCUC | 60 |
| Duox1 | exogenous expression | Duox1_2 SEQ ID NOS: 259-260 | Sense: CGAGAGAAGUUCCAACGCA Antisense: UGCGUUGGAACUUCUCUCG | 72 |
| Duox1 | exogenous expression | Duox1_3 SEQ ID NOS: 261-262 | Sense: ACCGAGAGAAGUUCCAACG Antisense: CGUUGGAACUUCUCUCGGU | 85 |
| Duox1 | exogenous expression | Duox1_4 SEQ ID NOS: 263-264 | Sense: AGAUCCCCAAGGAGUAUGA Antisense: UCAUACUCCUUGGGGAUCU | 84 |
| Duox1 | exogenous expression | Duox1_6 SEQ ID NOS: 265-266 | Sense: UUGCCUCCAUCCUCAAAGA Antisense: UCUUUGAGGAUGGAGGCAA | 80 |

*cell line used in assay,
**% of control in separate tests using 20 nM concentration of siRNA molecules.
All sequences are presented in a 5'-3' orientation.

TABLE C2

Percent of knockdown of the expression of the target human gene in cells using 23 mer siRNA molecules.

| Target gene | Cell line used for analysis | siRNA tested | Sequence | % of control** |
|---|---|---|---|---|
| CASP2 | HeLa- | CASP2_1-1 SEQ ID No. 267-268 | Sense: CCUUGCACUCCUGAAUUUUAUCA Antisense: UGAUAAAAUUCAGGAGUGCAAGG | 16 |
| CASP2 | HeLa- | CASP2_1-2 SEQ ID No. 269-270 | Sense: CUUGCACUCCUCAAUUUUAUCAA Antisense: UUGAUAAAAUUCAGGAGUGCAAG | 23 |
| CASP2 | HeLa- | CASP2_1-3 SEQ ID No. 271-272 | Sense: UUGCACUCCUGAAUUUUAUCAAA Antisense: UUUGAUAAAAUUCAGGAGUGCAA | 7 |
| CASP2 | HeLa- | CASP2_1-4 SEQ ID No. 273-274 | Sense: UGCACUCCUGAAUUUUAUCAAAC Antisense: GUUUGAUAAAAUUCAGGAGUGCA | 30 |
| CASP2 | HeLa- | CASP2_1-5 SEQ ID No. 275-276 | Sense: GCACUCCUGAAUUUUAUCAAACA Antisense: UGUUUGAUAAAAUUCAGGAGUGC | 10 |

*cell line used in assay,
**% of control in separate tests using 20 nM concentration of siRNA molecules.
All sequences are presented in a 5'-3' orientation.

TABLE C3

Percent of knockdown of the expression of the target human gene in cells using 19-mer siRNAs molecules.

| Target gene | Cell line* | siRNA tested | Sequence | % of control** |
|---|---|---|---|---|
| P2RX7 | Nalm6 | P2RX7_6 SEQ ID NOS: 50971-50972 | Sense: CCGAGAAACAGGCGAUAAU Antisense: AUUAUCGCCUGUUUCUCGG | 78 |
| P2RX7 | Nalm6 | P2RX7_7 SEQ ID NOS: 50973-50974 | Sense: CCAGACGCCAUUUAAAAGU Antisense: ACUUUUAAAUGGCGUCUGG | 73 |
| P2RX7 | Nalm6 | P2RX7_8 SEQ ID NOS: 50975-50976 | Sense: GUGGCUCUGAUUGCUUUAU Antisense: AUAAAGCAAUCAGAGCCAC | 75 |
| P2RX7 | Nalm6 | P2RX7_9 SEQ ID NOS: 50977-50978 | Sense: CCAAAGGGAAAUAUGCUUU Antisense: AAAGCAUAUUUCCCUUUGG | 60 (in 5 nM) |
| P2RX7 | Nalm6 | P2RX7_10 SEQ ID NOS: 50979-50980 | Sense: CACAACUACACCACGAGAA Antisense: UUCUCGUGGUGUAGUUGUG | 87 |
| TRPM2 | Nalm6 | TRPM2_5 SEQ ID NOS: 50981-50982 | Sense: GACAAUGCCUGGAUCGAGA Antisense: UCUCGAUCCAGGCAUUGUC | 85 |
| TRPM2 | Nalm6 | TRPM2_6 SEQ ID NOS: 50983-50984 | Sense: CCAAGAACUUCAACAUGAA Antisense: UUCAUGUUGAAGUUCUUGG | 46 |
| PARG | Nalm6 | PARG_2 SEQ ID NOS: 50985-50986 | Sense: GACAGAGUCUUGAAGAUUU Antisense: AAAUCUUCAAGACUCUGUC | 59 |
| PARG | Nalm6 | PARG_3 SEQ ID NOS: 50987-50988 | Sense: GUGGCAUAUUCUAAGAAAU Antisense: AUUUCUUAGAAUAUGCCAC | 60 |
| PARG | Nalm6 | PARG_5 SEQ ID NOS: 50989-50990 | Sense: CCCAGACAUUAACUUCAAU Antisense: AUUGAAGUUAAUGUCUGGG | 68 |
| CD38 | Nalm6 | CD38_5 SEQ ID NOS: 50991-50992 | Sense: GGGUGCAUUUAUUUCAAAA Antisense: UUUUGAAAUAAAUGCACCC | 0 (in 20 nM) 23 (in 5 nM) |

*cell line used in assay,
**% of control in separate tests using 20 nM concentration of siRNA molecules (except if indicated otherwise).
All sequences are presented in a 5'-3' orientation.

Example 2

Model Systems of Acute Renal Failure (ARF)

ARF is a clinical syndrome characterized by rapid deterioration of renal function that occurs within days. Without being bound by theory the acute kidney injury may be the result of renal ischemia-reperfusion injury such as renal ischemia-repercussion injury in patients undergoing major surgery such as major cardiac surgery. The principal feature of ARF is an abrupt decline in glomerular filtration rate (GFR), resulting in the retention of nitrogenous wastes (urea, creatinine). Recent studies, support that apoptosis in renal tissues is prominent in most human cases of ARF. The principal site of apoptotic cell death is the distal nephron. During the initial phase of ischemic injury, loss of integrity of the actin cytoskeleton leads to flattening of the epithelium, with loss of the brush border, loss of focal cell contacts, and subsequent disengagement of the cell from the underlying substratum.

Testing an active siRNA compound was performed using an animal model for ischemia-reperfusion-induced ARF.

Protection, Against Ischemia-Reperfusion Injury Induced ARF Using Specific Rac1, TP53BP2 and Casp2 siRNA Compounds Ischemia-reperfusion injury was induced in rats following 45 minutes bilateral kidney arterial clamp and subsequent release of the clamp to allow 24 hours of reperfusion. A dose of 12 mg/kg of the following siRNA compounds was injected into the jugular vein of individual experimental animals 30 minutes prior to and 4 hours following the clamp. ARF progression was monitored by measurement of serum creatinine levels before (baseline) and 24 hrs post surgery.

```
Rac1_2:
Sense sequence:     GAGUCCUGCAU-
                    CAUUUGAA, SEQ ID NO: 213;

Antisense           UUCAAAUGAUGCAGGA-
sequence:           CUC, SEQ ID NO: 214.

TP53BP2_2:
Sense               CACCCAGAGAACAUUUAUU, SEQ ID NO: 99;
sequence:

Antisense           AAUAAAUGUUCU-
sequence:           CUGGGUG, SEQ ID NO: 100.

Casp2_4:
Sense               GCCAGAAUGUGGAA-
sequence:           CUCCU, SEQ ID NO: 139;

Antisense           AGGAGUUCCA-
sequence:           CAUUCUGGU, SEQ ID NO: 140.
```

At the end of the experiment, the rats were perfused via an indwelling femoral line with warm PBS followed by 4% paraformaldehyde. The left kidneys were surgically removed and stored in 4% paraformaldehyde for subsequent histological analysis. Acute renal failure is frequently defined as an acute increase of the serum creatinine level from baseline. An increase of at least 0.5 mg per dL or 44.2 µmol per L of serum creatinine is considered as an indication for acute renal failure. Serum creatinine was measured at time zero before the surgery and at 24 hours post ARF surgery. Tables D1-D3 below demonstrate the results obtained in the ARF model in rats. As revealed from the results, RAC1, TP53BP2 and Casp2 siRNA compounds reduced creatinine levels following ischemia-reperfusion induced ARF in an experimental rat model.

Table D1: Treatment with Rac1_2 siRNA (SEQ ID NOS: 213-214)

Values represent creatinine levels [in mg/dL] prior to (Baseline) and 24 hours following ischemia-reperfusion induced ARF in placebo group (PBS), and in RAC1_2 siRNA treated rats 30 min prior to the ischemic injury (−30') and in RAC1_2 siRNA treated rats 4 hours post ischemic injury (+4 h).

TABLE D1

| Animal | creatinine levels Baseline | creatinine levels with PBS 24 h post ischemic injury | creatinine levels with RAC1_2 siRNA (−30') | creatinine levels with RAC1_2 siRNA (+4 h) |
| --- | --- | --- | --- | --- |
| 1 | 0.2 | 2.4 | 1.4 | 1.3 |
| 2 | 0.3 | 2.7 | 1.2 | 1.2 |
| 3 | 0.3 | 2.7 | 1.7 | 1.1 |
| 4 | 0.3 | 2.2 | 1.8 | 1.5 |
| 5 | 0.3 | 2.4 | 1.8 | 1.5 |
| 6 | 0.3 | 2.5 | 2.0 | 1.6 |
| Mean | 0.3 | 2.5 | 1.7 | 1.4 |

Table D2: Treatment with TP53BP2_2 siRNA (SEQ ID NOS:99-100). Values represent creatinine levels 24 hours following ischemia-reperfusion induced ARF in placebo group (PBS), in non-relevant GFP siRNA treated rats 4 hours post ischemic injury (GFP siRNA (+4 h)), in TP53BP2_2 siRNA treated rats 30 min prior to the ischemic injury (TPS3BP2_2 siRNA (−30')) and in TP53BP2_2 siRNA treated rats 4 hours post ischemic injury (TP53BP2_2 siRNA (+4 h)).

TABLE D2

| Animal | creatinine levels with PBS 24 h post ischemic injury | creatinine levels with GFP siRNA (+4 h) | creatinine levels with TP53BP2_2 siRNA (−30') | creatinine levels with TP53BP2_2 siRNA (+4 h) |
| --- | --- | --- | --- | --- |
| 1 | 3.5 | 3.10 | 2.20 | 1.80 |
| 2 | 4.10 | 2.80 | 2.20 | 1.90 |
| 3 | 4.20 | 3.20 | 2.50 | 1.1 |
| 4 | 3.30 | | 2.30 | 1.40 |
| 5 | | | 2.40 | |
| 6 | | | 2.20 | |
| Mean | 3.78 | 3.03 | 2.30 | 1.55 |
| STD | 0.44 | 0.21 | 0.13 | 0.37 |

Table D3: Treatment with Casp2_4 siRNA (SEQ ID NO:139-140). Values represent creatinine levels prior to (baseline) and 24 hours following ischemia-reperfusion induced ARF in placebo group (PBS), in Casp2_4 siRNA treated rats 30 min prior to the ischemic injury (−30') and in Casp2_4 siRNA treated rats 4 hours post ischemic injury (+4 h).

TABLE D3

| Animal | creatinine levels baseline | creatinine levels with PBS 24 h post ischemic injury | creatinine levels with Casp2_4 siRNA (−30') | creatinine levels with Casp2_4 siRNA (+4 h) |
| --- | --- | --- | --- | --- |
| 1 | 0.30 | 2.40 | 1.10 | 1.30 |
| 2 | 0.30 | 3.80 | 1.00 | 0.90 |
| 3 | 0.10 | 2.70 | 1.70 | 1.40 |
| 4 | 0.20 | 2.40 | 1.90 | 1.00 |
| 5 | 0.10 | 3.40 | 0.90 | 1.30 |
| 6 | 0.20 | 2.40 | 1.20 | 1.10 |
| Mean | 0.20 | 2.85 | 1.30 | 1.17 |
| STD | 0.09 | 0.61 | 0.40 | 0.20 |

Similar results are obtained following administration of other siRNA compounds from Table B, in particular siRNAs directed to particular genes TP538P2, LRDD. CYBA, ATF3, CASP2, HRK, CIQBP, BNIP3, MAPK8, MAPK14, RAC1, GSK3B, P2RX7, TRPM2, PARG, CD38, STEAP4, BMP2, CX43, TYROBP, CTGF, and SPP1.

Example 3

Model Systems of Pressure Sores or Pressure Ulcers

Pressure sores or pressure ulcers including diabetic ulcers, are areas of damaged skin and tissue that develop when sustained pressure (usually from a bed or wheelchair) cuts off circulation to vulnerable parts of the body, especially the skin on the buttocks, hips and heels. The lack of adequate blood flow leads to ischemic necrosis and ulceration of the affected tissue. Pressure sores occur most often in patients with diminished or absent sensation or who are debilitated, emaciated, paralyzed, or long bedridden. Tissues over the sacrum, ischia, greater trochanters, external malleoli, and heels are especially susceptible; other sites may be involved depending on the patient's situation.

Testing the active inhibitors of the invention (such as siRNA compounds) for treating pressure sore, ulcers and similar wounds is performed in the mouse model described in Reid et al., (J Surgical Research. 116:172-180, 2004).

An additional rabbit model (described by Mustoe et al. (JCI, 1991, 87(2):694-703; Ahn and Mustoe. Ann Pl Surg, 1991, 24(1): 17-23) is used for testing the siRNA compounds of the invention, siRNA according to Table B and specifically compounds directed to genes CIQBP, RAC1, GSK3B, P2RX7, TRPM2, PARG, CD38, STEAP4, BMP2, CX43, or TYROBP are tested in animal models where it is shown that these siRNA compounds treat and prevent pressure sores and ulcers.

Example 4

Model Systems of Chronic Obstructive Pulmonary Disease (COPD)

Chronic obstructive pulmonary disease (COPD) is characterized mainly by emphysema, a permanent destruction of peripheral air spaces distal to terminal bronchioles. Emphysema is also characterized by accumulation of inflammatory cells such as macrophages and neutrophils in bronchioles and alveolar structures. Emphysema and chronic bronchitis may occur as part of COPD or independently.

Testing the active inhibitors of the invention (such as siRNA) for treating COPD/emphysema/chronic bronchitis is performed in animal models such as those disclosed as follows:

Starcher and Williams, 1989. Lab. Animals, 23:234-240; Peng, et al., 2004.; Am J Respir Crit Care Med. 169:1245-1251; Jeyaseelan et al., 2004. Infect. Immunol. 72: 7247-56. Additional models are described in PCT Patent Publication WO 2006/023544 assigned to the assignee of the present application, which is hereby incorporated by reference into this application.

siRNA according to Table B, and in particular to siRNA to genes CIQBP, BNIP3, GSK3B, P2RX7, TRPM2, PARG, CD38, STEAP4, BMP2, CX43, TYROBP, CTGF, and DUOX1 are tested in these animal models, which show that these siRNA compounds may treat and/or prevent emphysema, chronic bronchitis and COPD.

Example 5

Model Systems of Spinal Cord Injury

Spinal cord injury, or myelopathy, is a disturbance of the spinal cord that results in loss of sensation and/or mobility. The two common types of spinal cord injury are due to trauma and disease. Traumatic injury can be due to automobile accidents, falls, gunshot, diving accidents inter alia, and diseases which can affect the spinal cord include polio, spina bifida, tumors and Friedreich's ataxia.

Uptake of siRNA Molecules into Neurons Following Injection into Injured Spinal-Cord:

The uptake of Cy3 labeled siRNA (delivered by injection into the injured cord) in different types of cells was examined following spinal cord contusion in 18 rats and in uninjured rats (9 rats). Sagittal cryosections were produced and immunostaining using four different groups of antibodies was performed in order to determine whether uptake has occurred in neurons, astroglia, oligodendroglia and/or macrophages/microglia. Markers for neurons were NeuN, or GAP43; markers for astroglia and potential neural stem cells were GFAP, nestin or vimentin; markers for oligodendroglia were NG2 or APC; markers for macrophages/microglia were ED1 or Iba-1 (Hasegawa et al., 2005. Exp Neurol 193 394-410).

Six rats were injected with two different doses of Cy3 labeled siRNA (1 µg/µl, 10 Jµg/µl) and were left for 1 and 3 days before sacrifice. Histological analyses indicate that many long filamentous profiles have taken up the labeled siRNA as well as other processes and cell bodies. Immunostaining with antibodies to MAP2 has identified uptake of label into dendrites and into cell bodies of neurons including motorneurons. Staining with other antibodies specific to astrocytes or macrophages revealed lower uptake of Cy3 labeled siRNA as compared to neurons. These results indicate that siRNA molecules injected to the injured spinal cord reach the cell body and dendrites of neurons including motorneurons.

Protection Against Spinal-Cord Injury Using Specific RhoA siRNA Compounds:

The Spinal-Cord Injury Animal Model:

Six adult female Sprague-Dawley rats were anesthetized with 40 mg/kg of pentobarbital and the spinal thoracic T9-10 was exposed by laminectomy. Contusive injury was produced by dropping a 10 gm rod onto the exposed spinal cord from a height of 12.5 mm using MASCIS (Multicenter Animal Spinal Cord Injury Study) impactor (as described In Basso et al., Journal of Neurotrauma Vol 12 (1), p 1-21 1995 and in Basso et al., Journal of Neurotrauma Vol 13 (7), p 343-59 1996). Prior to injury, three point injections of RhoA_4 siRNA (Sense sequence: GCCACUUAAUGUAU-GUUAC, SEQ ID NO:235; Antisense sequence: GUAACAUACAUUAAGUGGC, SEQ ID NO:236) at the concentration of 1 µg/µl were performed at the injury epicenter 2 mm rostral and caudal to the epicenter (total dose of 30 µg). GFP siRNA was injected in additional five rats as a control. Each injection was conducted slowly during a period of 10 min into dorsal column (~1 mm depth) of T10 using a Hamilton syringe. Following injections, muscles and skin were closed separately. Cefazolin (25 mg/kg) was administered for 7 days after surgery. The behavioral assessment of the recovery following the spinal cord contusion was preformed using an open field locomotor test as described by Basso et al (the BBB locomotor rating scale).

Table D4 below demonstrates the results obtained in the open field locomotor test following spinal-cord injury in rats. As summarized in Table D4 below, RhoA siRNA compounds protect against spinal-cord injury in an experimental rat model as revealed by significantly higher BBB locomotor score up to 6 weeks post injury in the RhoA siRNA treated mts.

Table D4: Treatment with RhoA_4 siRNA (SEQ ID NOS:235-236). Values represent mean BBB locomotor score following spinal-cord injury in placebo group (GFP siRNA) and in RhoA_4 siRNA treated group.

TABLE D4

| Animal | BBB score in day 2 post spinal cord injury | BBB score 1 week post spinal cord injury | BBB score 2 weeks post spinal cord injury | BBB score 3 weeks post spinal cord injury | BBB score 4 weeks post spinal cord injury | BBB score 5 weeks post spinal cord injury | BBB score 6 weeks post spinal cord injury |
|---|---|---|---|---|---|---|---|
| RhoA | 1 | 9 | 11 | | | | |
| RhoA | 2 | 9 | 13 | | | | |
| RhoA | 0.5 | 8 | 10 | 10.5 | 10.5 | 12 | 13 |
| RhoA | 4 | 9 | 12 | 18 | 12 | 16 | 18 |
| RhoA | 4 | 11 | 13 | 14 | 18 | 18 | 14 |
| RhoA | 4 | 8.5 | 12 | 13 | 12 | 12 | 16 |
| Mean | 2.583 | 9.083 | 11.833 | 13.875 | 13.125 | 14.5 | 15.25 |
| | | ($p = 0.042$) | ($p = 0.0006$) | ($p = 0.0301$) | | ($p = 0.0302$) | ($p = 0.0140$) |
| STD | 1.625 | 1.021 | 1.169 | 3.119 | 3.326 | 3 | 2.217 |
| GFP | 2 | 7 | 9 | 9 | 9.5 | 10 | 11 |
| GFP | 0 | 7 | 9 | 9.5 | 10 | 11 | 12 |
| GFP | 3 | 7 | 9.5 | 11 | 11 | 11 | 12 |
| GFP | 0.5 | 7 | 9 | 11 | 12 | 12 | 13 |
| GFP | 0.5 | 8 | 9 | 9 | 9 | 9 | 10.5 |
| Mean | 1.2 | 7.2 | 9.1 | 9.9 | 10.3 | 10.6 | 11.7 |
| STD | 1.255 | 0.447 | 0.224 | 1.025 | 1.204 | 1.14 | 0.975 | siRNA compounds according to Table B and in particular siRNA directed to genes LRDD, CYBA, ATF3, CASP2, HRK, CIQBP, BNIP3, MAPK8, MAPK14, RAC1, GSK3B, P2RX7, TRPM2, PARG, CD38, STEAP4, BMP2, CX43, TYROBP, CTGF, and RHOA are tested in this animal model, which show that these siRNA compounds promote functional recovery following spinal cord injury and thus may be used to treat spinal cord injury.

Example 6

Model Systems of Glaucoma

Testing the active inhibitors of the invention (such as siRNA) for treating or preventing glaucoma is done in the animal model for example as described by Pease et al., J. Glaucoma, 2006, 15(6):512-9 (Manometric calibration and comparison of TonoLab and TonoPen tonometers in rats with experimental glaucoma and in normal mice).

siRNA according to Table B in particular to genes TP53BP2, LRDD, CYBA, ATF3, CASP2, HRK, BNIP3, MAPK8, MAPK14, RAC1, and RHOA are tested in this animal model which show that these siRNA compounds treat and/or prevent glaucoma.

Example 7

Model Systems of Ischemia/Reperfusion Injury Following Lung Transplantation in Rats Testing the active inhibitors of the invention (such as siRNA) for treating or preventing ischemia/reperfusion injury or hypoxic injury following lung transplantation is done in one or more of the experimental animal models, for example as described by Mizobuchi et al., (2004. J. Heart Lung Transplant, 23:889-93); Huang, et al., (1995. J. Heart Lung Transplant. 14: S49); Matsumura, et alt. (1995. Transplantation 59: 1509-1517); Wilkes, et al., (1999. Transplantation 67:890-896); Naka, et al., (1996, Circulation Research, 79: 773-783).

siRNA according to Table B and in particular to TP53BP2, LRDD. CYBA, CASP2, BNIP3, RAC1, and DUOX1 are tested in these animal models, which show that these siRNA compounds treat and/or prevent ischemia-reperfusion injury following lung transplantation and thus may be used in conjunction with transplant surgery.

Example 8

Model Systems of Acute Respiratory Distress Syndrome

Testing the active inhibitors of the invention (such as siRNA) for treating acute respiratory distress syndrome is done in the animal model as described by Chen, et al (J Biomed Sci. 2003; 10(6 Pt 1):588-92), siRNA compounds according to Table B in particular to genes CYBA, HRK. BNIP3, MAPK8, MAPK14. RAC1. GSK3B. P2RX7, TRPM2, PARG, SPP1. and DUOX1 are tested in this animal model which shows that these siRNAs treat and/or prevent acute respiratory distress syndrome and thus may be used to treat this condition.

Example 9

Model Systems of Hearing Loss Conditions (i) Distribution of Cy3-PTEN siRNA in the cochlea following local application to the round window of the ear:

A solution of 1 μg/100 μl of Cy3-PTEN siRNA (total of 0.3-0.4 μg) PBS was applied to the round window of chinchillas. The Cy3-labelled cells within the treated cochlea were analyzed 24-48 hours post siRNA round window application after sacrifice of the chinchillas. The pattern of labeling within the cochlea was similar following 24 h and 48 h and includes labeling in the basal turn of cochlea, in the middle turn of cochlea and in the apical turn of cochlea. Application of Cy3-PTEN siRNA onto scala tympani revealed labelling mainly in the basal turn of the cochlea and the middle turn of the cochlea. The Cy3 signal was persistence to up to 15 days after the application of the Cy3-PTEN siRNA. These results indicated for the first time that local application of siRNA molecules within the round window led to significant penetration of the siRNA molecules to the basal, middle and apical turns of the cochlea. The siRNA compounds of the invention are tested in this animal model which shows that there is significant penetration of these siRNA compounds to the basal, middle and apical turns of the cochlea, and that these compounds may be used in the treatment of hearing loss.

(ii) Chinchilla model of carboplatin-induced or cisplatin-induced cochlea hair cell death Chinchillas are pre-treated by direct administration of specific siRNA in saline to the left ear of each animal. Saline is given to the right ear of each animal as placebo, Two days following the administration of the specific siRNA compounds of the invention, the animals are treated with carboplatin (75 mg/kg ip) or cisplatin (intraperitoneal infusion of 13 mg/kg over 30 minutes). After sacrifice of the chinchillas (two weeks post carboplatin treatment) the % of dead cells of inner hair cells (IHC) and outer hair cells (OHC) is calculated in the left ear (siRNA treated) and in the right ear (saline treated). It is calculated that the % of dead cells of inner hair cells (IHC) and outer hair cells (OHC) is lower in the left ear (siRNA treated) than in the right ear (saline treated).

(iii) Chinchilla model of acoustic-induced cochlea hair cell death:

The activity of specific siRNA in an acoustic trauma model is studied in chinchilla. The animals are exposed to an octave band of noise centered at 4 kHz for 2.5 h at 105 dB. The left ear of the noise-exposed chinchillas is pre-treated (48 h before the acoustic trauma) with 30 μg of siRNA in ~10 μL of saline; the right ear is pre-treated with vehicle (saline). The compound action potential (CAP) is a convenient and reliable electrophysiological method for measuring the neural activity transmitted from the cochlea. The CAP is recorded by placing an electrode near the base of the cochlea in order to detect the local field potential that is generated when a sound stimulus, such as click or tone burst, is abruptly turned on. The functional status of each ear is assessed 2.5 weeks after the acoustic trauma. Specifically, the mean threshold of the compound action potential recorded from the round window is determined 2.5 weeks after the acoustic trauma in order to determine if the thresholds in the siRNA-treated ear are lower (better) than the untreated (saline) ear. In addition, the amount of inner and outer hair cell loss is determined in the siRNA-treated and the control car.

siRNA molecules according to Table B in particular to genes TP53BP2, LRDD, CYBA. ATF3, CASP2, NOX3, HRK, CIQBP, BNIP3, MAPK8, MAPK14, RAC1, GSK3B, P2RX7, TRPM2, PARG, CD38, STEAP4, BMP2, CX43, TYROBP, and CTGF are tested in this animal model which shows that the thresholds in the siRNA-treated ear are lower (better) than in the untreated (saline) ear. In addition, the amount of inner and outer hair cell loss is lower in the siRNA-treated ear than in the control ear, Example 10

Animal Models of Osteoarthritis (OA)

Collagen induced arthritis (CIA): CIA in mice is described in Trentham et al. (1977. J. Exp. Med. 146: 857-868). Adjuvant-induced arthritis (AA):AA is described in Kong et al., (1999. Nature, 402:304-308). A menisectomy model is described in Han et al., (1999, Nagoya J Med Sci 62(3-4):115-26).

The effect of different siRNA inhibitors, such as siRNA to SSP1, on different parameters related to OA such as chondrocyte proliferation, terminal differentiation and development of arthritis, is evaluated using one or more of the above models, in addition to in vitro models known in the art, siRNA compounds according to Table B, in particular to SSP1, are tested in these animal models which show that these siRNAs treat and/or prevent OA and thus may be used to treat this condition.

The siRNAs used in the in vivo experiments described herein were all 19-mers, having alternating ribonucleotides modified in both the antisense and the sense strands of the compound. The modification was such that a 2'-O-methyl (Me) group was present on the first, third, fifth, seventh, ninth, eleventh, thirteenth. fifteenth, seventeenth and nineteenth nucleotide of the antisense strand, whereby the very same modification, i.e. a 2'-O-Me group, was present at the second, fourth, sixth, eighth, tenth, twelfth, fourteenth, sixteenth and eighteenth nucleotide of the sense strand. These particular siRNA compounds were also blunt ended and were non-phosphorylated at the termini; however, comparative experiments have shown that siRNAs phosphorylated at the 3'-termini have similar activity.

Example 11

Generation of Sequences for Active siRNA Compounds to Pro-Apoptotic Genes and Production of the siRNAs Using proprietary algorithms and the known sequence of the pro-apoptotic genes, the sequences of many potential siRNAs were generated, in addition to the algorithm, some of the 23-mer oligomer sequences were generated by 5' and/or 3' extension of the 19-mer sequences. The sequences that have been generated using this method are fully complementary to the corresponding mRNA sequence.

Table B (SEQ ID NOS:277-50970 and 50993-68654) shows siRNAs for the following pro-apoptotic genes: TP53BP2, LRDD, CYBA, ATF3, CASP2, NOX3, HRK, CIQBP, BNIP3, MAPK8, MAPK14, RAC1, GSK3B, P2RX7, TRPM2, PARG, CD38, STEAP4, BMP2, CX43, TYROBP, CTGF, SPP1, RHOA, and DUOX1 For each gene there is a separate list of 19-mer, 21-mer and 23-mer siRNA sequences, which are prioritized based on their score in the proprietary algorithm as the best sequences for targeting the human gene expression.

The following abbreviations are used in the Table B herein: "other spec or Sp." refers to cross species identity; chn: chinchilla; chp: chimpanzee, chk: chicken; guinea-pig: GP; mnk: monkey; ms: mouse; rt: rat; sp: sheep: rb: rabbit; ORF: open reading frame. 19-mers. 21-mers and 23-mers refer to oligomers of 19, 21 and 23 ribonucleic acids in length.

Lengthy table referenced here

US09446062-20160920-T00001

Please refer to the end of the specification for access instructions.

Lengthy table referenced here

US09446062-20160920-T00002

Please refer to the end of the specification for access instructions.

Lengthy table referenced here
US09446062-20160920-T00003

Please refer to the end of the specification for access instructions.

Lengthy table referenced here
US09446062-20160920-T00004

Please refer to the end of the specification for access instructions.

Lengthy table referenced here
US09446062-20160920-T00005

Please refer to the end of the specification for access instructions.

Lengthy table referenced here
US09446062-20160920-T00006

Please refer to the end of the specification for access instructions.

Lengthy table referenced here
US09446062-20160920-T00007

Please refer to the end of the specification for access instructions.

Lengthy table referenced here
US09446062-20160920-T00008

Please refer to the end of the specification for access instructions.

Lengthy table referenced here
US09446062-20160920-T00009

Please refer to the end of the specification for access instructions.

Lengthy table referenced here
US09446062-20160920-T00010

Please refer to the end of the specification for access instructions.

Lengthy table referenced here
US09446062-20160920-T00011

Please refer to the end of the specification for access instructions.

Lengthy table referenced here
US09446062-20160920-T00012

Please refer to the end of the specification for access instructions.

Lengthy table referenced here
US09446062-20160920-T00013

Please refer to the end of the specification for access instructions.

Lengthy table referenced here
US09446062-20160920-T00014

Please refer to the end of the specification for access instructions.

Lengthy table referenced here
US09446062-20160920-T00015

Please refer to the end of the specification for access instructions.

Lengthy table referenced here
US09446062-20160920-T00016

Please refer to the end of the specification for access instructions.

Lengthy table referenced here
US09446062-20160920-T00017

Please refer to the end of the specification for access instructions.

Lengthy table referenced here
US09446062-20160920-T00018

Please refer to the end of the specification for access instructions.

Lengthy table referenced here
US09446062-20160920-T00019

Please refer to the end of the specification for access instructions.

Lengthy table referenced here
US09446062-20160920-T00020

Please refer to the end of the specification for access instructions.

Lengthy table referenced here
US09446062-20160920-T00021
Please refer to the end of the specification for access instructions.

Lengthy table referenced here
US09446062-20160920-T00022
Please refer to the end of the specification for access instructions.

Lengthy table referenced here
US09446062-20160920-T00023
Please refer to the end of the specification for access instructions.

Lengthy table referenced here
US09446062-20160920-T00024
Please refer to the end of the specification for access instructions.

Lengthy table referenced here
US09446062-20160920-T00025
Please refer to the end of the specification for access instructions.

Lengthy table referenced here
US09446062-20160920-T00026
Please refer to the end of the specification for access instructions.

Lengthy table referenced here
US09446062-20160920-T00027
Please refer to the end of the specification for access instructions.

Lengthy table referenced here
US09446062-20160920-T00028
Please refer to the end of the specification for access instructions.

Lengthy table referenced here
US09446062-20160920-T00029
Please refer to the end of the specification for access instructions.

Lengthy table referenced here
US09446062-20160920-T00030
Please refer to the end of the specification for access instructions.

Lengthy table referenced here
US09446062-20160920-T00031
Please refer to the end of the specification for access instructions.

Lengthy table referenced here
US09446062-20160920-T00032
Please refer to the end of the specification for access instructions.

Lengthy table referenced here
US09446062-20160920-T00033
Please refer to the end of the specification for access instructions.

Lengthy table referenced here
US09446062-20160920-T00034
Please refer to the end of the specification for access instructions.

Lengthy table referenced here
US09446062-20160920-T00035
Please refer to the end of the specification for access instructions.

Lengthy table referenced here
US09446062-20160920-T00036
Please refer to the end of the specification for access instructions.

Lengthy table referenced here
US09446062-20160920-T00037
Please refer to the end of the specification for access instructions.

Lengthy table referenced here
US09446062-20160920-T00038
Please refer to the end of the specification for access instructions.

Lengthy table referenced here
US09446062-20160920-T00039
Please refer to the end of the specification for access instructions.

Lengthy table referenced here
US09446062-20160920-T00040
Please refer to the end of the specification for access instructions.

Lengthy table referenced here
US09446062-20160920-T00041
Please refer to the end of the specification for access instructions.

Lengthy table referenced here
US09446062-20160920-T00042
Please refer to the end of the specification for access instructions.

Lengthy table referenced here
US09446062-20160920-T00043
Please refer to the end of the specification for access instructions.

Lengthy table referenced here
US09446062-20160920-T00044
Please refer to the end of the specification for access instructions.

Lengthy table referenced here
US09446062-20160920-T00045
Please refer to the end of the specification for access instructions.

Lengthy table referenced here
US09446062-20160920-T00046
Please refer to the end of the specification for access instructions.

Lengthy table referenced here
US09446062-20160920-T00047
Please refer to the end of the specification for access instructions.

Lengthy table referenced here
US09446062-20160920-T00048
Please refer to the end of the specification for access instructions.

Lengthy table referenced here
US09446062-20160920-T00049
Please refer to the end of the specification for access instructions.

Lengthy table referenced here
US09446062-20160920-T00050
Please refer to the end of the specification for access instructions.

Lengthy table referenced here
US09446062-20160920-T00051
Please refer to the end of the specification for access instructions.

Lengthy table referenced here
US09446062-20160920-T00052
Please refer to the end of the specification for access instructions.

Lengthy table referenced here
US09446062-20160920-T00053
Please refer to the end of the specification for access instructions.

Lengthy table referenced here
US09446062-20160920-T00054
Please refer to the end of the specification for access instructions.

Lengthy table referenced here
US09446062-20160920-T00055
Please refer to the end of the specification for access instructions.

Lengthy table referenced here
US09446062-20160920-T00056
Please refer to the end of the specification for access instructions.

Lengthy table referenced here
US09446062-20160920-T00057
Please refer to the end of the specification for access instructions.

Lengthy table referenced here
US09446062-20160920-T00058
Please refer to the end of the specification for access instructions.

Lengthy table referenced here
US09446062-20160920-T00059
Please refer to the end of the specification for access instructions.

Lengthy table referenced here
US09446062-20160920-T00060
Please refer to the end of the specification for access instructions.

Lengthy table referenced here
US09446062-20160920-T00061
Please refer to the end of the specification for access instructions.

Lengthy table referenced here
US09446062-20160920-T00062
Please refer to the end of the specification for access instructions.

Lengthy table referenced here
US09446062-20160920-T00063
Please refer to the end of the specification for access instructions.

Lengthy table referenced here
US09446062-20160920-T00064
Please refer to the end of the specification for access instructions.

Lengthy table referenced here
US09446062-20160920-T00065
Please refer to the end of the specification for access instructions.

Lengthy table referenced here
US09446062-20160920-T00066
Please refer to the end of the specification for access instructions.

Lengthy table referenced here
US09446062-20160920-T00067
Please refer to the end of the specification for access instructions.

Lengthy table referenced here
US09446062-20160920-T00068
Please refer to the end of the specification for access instructions.

Lengthy table referenced here
US09446062-20160920-T00069
Please refer to the end of the specification for access instructions.

Lengthy table referenced here
US09446062-20160920-T00070
Please refer to the end of the specification for access instructions.

Lengthy table referenced here
US09446062-20160920-T00071
Please refer to the end of the specification for access instructions.

Lengthy table referenced here
US09446062-20160920-T00072
Please refer to the end of the specification for access instructions.

Lengthy table referenced here
US09446062-20160920-T00073
Please refer to the end of the specification for access instructions.

Lengthy table referenced here
US09446062-20160920-T00074
Please refer to the end of the specification for access instructions.

| Lengthy table referenced here | Lengthy table referenced here |
|---|---|
| US09446062-20160920-T00075 | US09446062-20160920-T00076 |
| Please refer to the end of the specification for access instructions. | Please refer to the end of the specification for access instructions. |

LENGTHY TABLES

The patent contains a lengthy table section. A copy of the table is available in electronic form from the USPTO web site (http://seqdata.uspto.gov/?pageRequest=docDetail&DocID=US09446062B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09446062B2). An electronic copy of the "Sequence Listing" will also be available from the USPTO upon request and payment of the fee set forth in 37 CFR 1.19(b)(3).

The invention claimed is:

1. A method of treating ischemia-reperfusion injury, the method comprising administering to a patient in need thereof a therapeutically effective dose of a double-stranded ribonucleic acid (RNA) compound comprising the structure:

```
                                      (SEQ ID NO: 140)
5'    AGGAGUUCCACAUUCUGGC-Z 3' (antisense strand)

(SEQ ID NO: 139)
3' Z'-UCCUCAAGGUGUAAGACCG 5' (sense strand);
``` wherein each A, C, G, and U is a ribonucleotide which may be modified or unmodified in its sugar residue and wherein each consecutive ribonucleotide is joined to the next ribonucleotide by a covalent bond; and wherein each of Z and Z' may be present or absent, but if present is 1 to 5 consecutive nucleotides covalently attached at the 3' terminus of the strand in which it is present;

or a pharmaceutically acceptable salt of the double-stranded RNA compound.

2. The method of claim 1, wherein the covalent bond joining each consecutive ribonucleotide is a phosphodiester bond.

3. The method of claim 1, wherein at least one ribonucleotide comprises a modification in a sugar residue of the at least one ribonucleotide.

4. The method of claim 3, wherein the modification comprises a modification at the 2' position, said modification preferably comprising the presence of an amino, a fluoro, an alkoxy, or an alkyl group.

5. The method of claim 4, wherein the modification comprises the presence of an alkoxy group which is a methoxy (2'-O-methyl) group.

6. The method of claim 1, wherein alternating ribonucleotides in the antisense strand, the sense strand, or both the sense and antisense strands are modified in sugar residues of said alternating ribonucleotides.

7. The method of claim 6, wherein each ribonucleotide at the 5' and 3' termini of the antisense strand is modified in a sugar residue of each said ribonucleotide of the antisense strand, and each ribonucleotide at the 5' and 3' termini of the sense strand is unmodified in a sugar residue of each said ribonucleotide of the sense strand.

8. The method of claim 1, wherein both the antisense strand and the sense strand are non-phosphorylated at both 3' termini and 5' termini of said antisense strand and said sense strand.

9. The method of claim 1, wherein both the antisense strand and the sense strand are phosphorylated at a 3' termini of said antisense strand and said sense strand.

10. The method of claim 1, wherein both Z and Z' are absent.

11. The method of claim 1, wherein one or both of Z and Z' are present.

12. The method of claim 1, wherein a 2'-O-methyl group is present on the first, third, fifth, seventh, ninth, eleventh, thirteenth, fifteenth, seventeenth, and nineteenth nucleotide of the antisense strand, and wherein a 2'-O-methyl group is present on the second, fourth, sixth, eighth, tenth, twelfth, fourteenth, sixteenth and eighteenth nucleotide of the sense strand.

13. The method of claim 1, wherein the double-stranded RNA compound is combined with a pharmaceutically acceptable carrier.

14. The method of claim 1, wherein the ischemia-reperfusion injury comprises acute renal failure.

* * * * *